US012403110B2

(12) United States Patent
Griscelli et al.

(10) Patent No.: US 12,403,110 B2
(45) Date of Patent: Sep. 2, 2025

(54) METHODS AND COMPOSITIONS FOR TREATING CANCERS

(71) Applicants: INSTITUT NATIONAL DE LA SANTÉ ET DE LA RECHERCHE MÉDICALE (INSERM), Paris (FR); ASSISTANCE PUBLIQUE—HÔPITAUX DE PARIS, Paris (FR); UNIVERSITÉ PARIS-SACLAY, Saint-Aubin (FR); UNIVERSITÉ PARIS CITÉ, Paris (FR)

(72) Inventors: Frank Griscelli, Villejuif (FR); Ali Turhan, Villejuif (FR); Annelise Bennaceur Griscelli, Villejuif (FR); Christophe Desterke, Villejuif (FR)

(73) Assignees: INSTITUT NATIONAL DE LA SANTÉ ET DE LA RECHERCHE MÉDICALE (INSERM), Paris (FR); ASSISTANCE PUBLIQUE-HÔPITAUX DE PARIS, Paris (FR); UNIVERSITÉ PARIS-SACLAY, Paris (FR); UNIVERSITÉ PARIS CITÉ, Paris (FR)

( * ) Notice: Subject to any disclaimer, the term of this patent is extended or adjusted under 35 U.S.C. 154(b) by 0 days.

(21) Appl. No.: 18/207,752

(22) Filed: Jun. 9, 2023

(65) Prior Publication Data
US 2023/0338494 A1 Oct. 26, 2023

Related U.S. Application Data

(62) Division of application No. 16/766,438, filed as application No. PCT/EP2018/082429 on Nov. 23, 2018, now Pat. No. 11,679,148.

(30) Foreign Application Priority Data

Nov. 24, 2017 (EP) ..................................... 17306635

(51) Int. Cl.
| | | |
|---|---|---|
| A61K 35/28 | (2015.01) | |
| A61K 31/19 | (2006.01) | |
| A61K 35/30 | (2015.01) | |
| A61K 35/34 | (2015.01) | |
| A61K 35/35 | (2015.01) | |
| A61K 35/545 | (2015.01) | |
| A61K 39/39 | (2006.01) | |
| A61K 40/00 | (2025.01) | |
| A61K 40/10 | (2025.01) | |
| A61K 40/42 | (2025.01) | |
| A61P 35/00 | (2006.01) | |
| A61K 39/00 | (2006.01) | |

(52) U.S. Cl.
CPC .............. *A61K 31/19* (2013.01); *A61K 39/39* (2013.01); *A61K 40/10* (2025.01); *A61K 40/4242* (2025.01); *A61P 35/00* (2018.01); *A61K 2039/515* (2013.01); *A61K 2239/31* (2023.05); *A61K 2239/38* (2023.05); *A61K 2239/54* (2023.05)

(58) Field of Classification Search
None
See application file for complete search history.

(56) References Cited

U.S. PATENT DOCUMENTS

| 5,637,483 | A | 6/1997 | Dranoff et al. |
|---|---|---|---|
| 2013/0136722 | A1 | 5/2013 | Mahmud |
| 2014/0193458 | A1 | 7/2014 | Bridle et al. |
| 2018/0296850 | A1 | 10/2018 | Wang |

FOREIGN PATENT DOCUMENTS

| EP | 2599860 A1 | 6/2013 |
|---|---|---|
| WO | 2012122629 A1 | 9/2012 |
| WO | 2016065330 A1 | 4/2016 |
| WO | 2016094948 A1 | 6/2016 |
| WO | 2017027757 A2 | 2/2017 |
| WO | 2017202949 A1 | 11/2017 |

OTHER PUBLICATIONS

Cheng et al. Self-Renewing Endodermal Progenitor Lines Generated from Human Pluripotent Stem Cells. Cell Stem Cell 10, 371-384, Apr. 6, 2012.*
Kondo et al. Histone Deacetylase Inhibitor Valproic Acid Promotes the Differentiation of Human Induced Pluripotent Stem Cells into Hepatocyte-Like Cells. PLoS One, 2014, 9(8): e104010.*
Hayashi et al. Effects of Ionizing Radiation on Proliferation and Differentiationof Mouse Induced Pluripotent Stem Cells. J. Radiat. Res., 53, 195-201 (2012).*
Li et al. Vaccination efficacy with marrow mesenchymal stem cell against cancer was enhanced under simulated microgravity. Biochemical and Biophysical Research Communications 485 (2017) 606-613.*
International Search Report and Written Opinion issued on May 6, 2019 for corresponding PCT Application No. PCT/EP2018/082429.
L. Shen et al., "Class I Histone Deacetylase Inhibitor Entinostat Suppresses Regulatory T Cells and Enhances Immunotherapies in Renal and Prostate Cancer Models," PLOS One, vol. 7, Issue 1, 2012, pp. 1-14.

(Continued)

*Primary Examiner* — Nianxiang Zou
(74) *Attorney, Agent, or Firm* — POLSINELLI PC

(57) ABSTRACT

The inventors provide a new therapeutic strategy to treat cancers expressing embryonic antigens. Accordingly, the present invention relates to a method of treating a subject suffering from a cancer comprising a step of administration simultaneously, separately or sequentially to said subject a therapeutically amount of i) a population of derived engineered fetal stem cells carrying cancer associated fetal neo-antigen and ii) a compound selected from a group which activates immune response, as a combined preparation.

15 Claims, 15 Drawing Sheets

(56) References Cited

OTHER PUBLICATIONS

Figure 1:
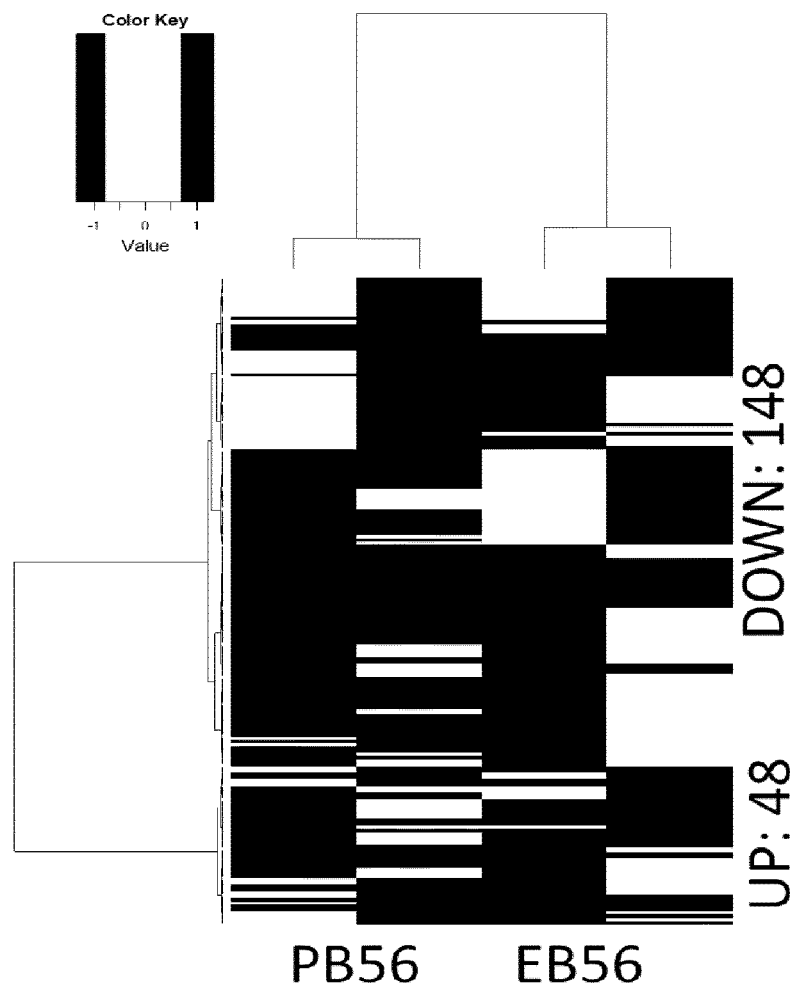

D. N. Lisiero et al., "The histone deacetylase inhibitor, LBH589, promotes the systemic cytokine and effector responses of adoptively transferred CD8+ T cells," Journal of Immuno Therapy of Cancer, vol. 2, No. 8, 2014, pp. 1-12.

M-D Lai et al., "An HDAC inhibitor enhances the antitumor activity of a CMV promoter-driven DNA vaccine," Cancer Gene Therapy, vol. 17, 2010, pp. 203-211.

D. L. Bartlett et al., "Oncolytic viruses as therapeutic cancer vaccines," Molecular Cancer, vol. 12, No. 103, 2013, pp. 1-16.

B. W. Bridle et al., "HDAC Inhibition Suppresses Primary Immune Responses, Enhances Secondary Immune Responses, and Abrogates Autoimmunity During Tumor Immunotherapy," Molecular Therapy, vol. 21, No. 4, 2013, pp. 887-894.

D. Wu et al., "Effect of targeted ovarian cancer immunotherapy using ovarian cancer stem cell vaccine," Journal of Ovarian Research, vol. 8, No. 1, 2015, pp. 1-10.

Q. Zheng et al., "A hepatic stem cell vaccine is superior to an embryonic stem cell vaccine in the prophylaxis and treatment of murine hepatocarcinoma," Oncology Reports, vol. 37, 2017, pp. 1716-1724.

A.S. Bear et al., "T Cells as Vehicles for Cancer VAccination," Journal of Biomedicine and Biotechnology, 2011, pp. 1-8.

S. A. Brodie et al., "Could valproic acid be an effective anticancer agent? The evidence so far," Expert Rev Anticancer Ther., vol. 14, No. 10, 2014, pp. 1097-1100.

B. G. Debeb et al., "Histone Deacetylase Inhibitors Stimulate Dedifferentiation of Human Breast Cancer Cells through WNT/B-catein Signaling," Stem Cells, vol. 30, No. 11, 2012, pp. 2366-2377.

W. Dong et al., "Antitumor Effect of Embryonic Stem Cells in a Non-Small Cell Lung Cancer Model: Antitumor Factors and Immune Responses," International journal of Medical Sciences, vol. 10, No. 10, 2013, pp. 1314-1320.

N. M. Lindor et al., "Concise Handbook of Familial Cancer Susceptibility Syndromes," Journal of the National Cancer Institute Monographs, No. 38, 2008, pp. 1-93.

C. J. M. Melief et al., "Therapeutic cancer vaccines," The Journal of Clinical Investigation, vol. 125, No. 9, 2015, pp. 3401-3412.

K. Rezvani et al., "Cancer Vaccines and T Cell Therapy," Biol Blood Marrow Transplant, vol. 19, 2013, pages: S97-S101.

S. J. Sharkis et al., "Pluripotent Stem Cell-Based Cancer Therapy: Promise and Challenges," Sci Transl Med., vol. 4, No. 127, 2012, pp. 1-8.

U. Golla et al., "PS7-14: Investigation of molecular mechanism of action of Valproic acid, an anticancer drug using budding yeast as a model organism," Article, 2015.

J. L. Vivian et al., "An allelic series of mutations in Smad2 and Smad4 identified in a genotype-based screen of N-ethyl-N-notrosourea-mutagenized mouse embryonic stem cells," PNAS, vol. 99, No. 24, 2002, pp. 15542-15547.

K. Takahashi et al., "Induction of Pluripotent Stem Cells from Mouse Embryonic and Adult Fibroblast Cultures by Defined Factors," Cell, vol. 126, 2006, pp. 663-676.

S. Yoshizaki et al., "Vaccination with human induced pluripotent stem cells creates an antigen-specific immune response against HIV-1 gp160," Original Research Article, vol. 2, Article 27, 2011, pp. 1-8.

Y. Zhang et al., "Antitumor activity of pluripotent cell-engineered vaccines and their potetial to treat lung cancer in relation to different levels of irradiation," OncoTargets and Therapy, Vil. 9, 2016, pp. 1425-1436.

S. Zheng et al., "Retake the Center Stage—New Development of Rat Genetics," Journal of Genetics and Genomics, vol. 39, 2012, pp. 261-268.

Dario O. Fauza, "Tissue Engineering and Transplantation in the Fetus," Transplantation of Engineering Cells and Tissues, Chapter 26, pp. 1-19.

Nigel G. Kooreman et al., "Autologous iPSC-based Vaccines Elicit Anti-Tumor Responses in Vivo," Cell Stem Cell. vol. 22, No. 4, 2018, pp. 501-513.e7.

Lee et al. Modeling Familial Cancer with Induced Pluripotent Stem Cells. Cell 161, 240-254, Apr. 9, 2015.

"Definition of fetal—NCI Dictionary of Cancer Terms—NCI" downloaded from Internet Aug. 2, 2022 (https://www.cancer.gov/publications/dictionaries/cancer-terms/def/fetal).

CXCR4 gene, downloaded Aug. 3, 2022 from internet: https://medlineplus.gov/genetics/gene/cxcr4/.

\* cited by examiner

| Verinostat | 1.5 µM |
| Entinestat | 1µM |
| Leviteracetam | 1µM |
| Valproic acid | 1mM |

METHODS AND COMPOSITIONS FOR TREATING CANCERS

CROSS-REFERENCE TO RELATED APPLICATIONS

This application claims priority to and is a divisional of U.S. patent application Ser. No. 16/766,438, filed on May 22, 2020, which is a national stage application (under 35 U.S.C. § 371) of PCT/EP2018/082429, filed Nov. 23, 2018, which claims benefit of European Application No. 17306635.8, filed Nov. 24, 2017, the entirety of which is herein incorporated by reference.

FIELD OF THE INVENTION

The present invention is in the field of oncology, and more specifically, the invention relates to an anticancer vaccine combined therapy.

More particularly, the invention relates to methods of producing a composition comprising fetal stem cells presenting multiple neo-antigens and thereof useful in preparing the cancer cell vaccines.

BACKGROUND OF THE INVENTION

Cancer stem cells (CSCs) represent a minor population of self-renewing cancer cells that are responsive of tumor persistence and recurrence since they are likely to be resistant to conventional treatments. Those CSCs have recently been evidenced in solid tumors from various origins including breast, colon head and neck carcinomas and represent a new therapeutic target. It has shown that those CSC express a large number of embryonic antigens which share the expression with human Embryonic Stem Cells (hESCs) or human Induced Pluripotent Stem Cells (hiPSCs). The expression of some of those embryonic antigens has also been found in differentiated cancer cells that are associated with tumorigenesis and/or tumor progression. Furthermore, cancers also express fetal antigens that are not expressed in pluripotent cells.

During the last decade, cancer treatment approaches have progressed from targeted therapies to immune intervention strategies with an unprecedented gain on survival as well as cancer related morbidity and mortality. However, despite the proved efficacy and clinical benefits of immune checkpoint inhibitors, there are a large number of partial responders and primary resistance tumors ("innate resistance") caused by immune-regulatory factors affecting tumor-specific immune responses and cancer-cell-autonomous cues. After initial response to PD-1/PD-L1 blockade, acquired resistance occurs in a high number of cancers in progression and relapse. The mechanism underlying acquired resistance to PD1/PDL-1 blockage is caused by evolution of neoantigen landscape with acquired somatic mutations (mutanome), an evolutive tumor immune micro-environment (TIME) with an epigenetic stability of exhausted T cells.

Cancer germline antigens represent proteins that are expressed during embryonic and fetal development and these epigenetically controlled antigens can be re-expressed in a variable proportion of many cancer. To date several human cancer vaccine trials have been set up in order to target embryonic antigens such as carcinoembryonic antigen (CEA), alpha fetoprotein or cancer/testes antigens (NY-ESO-1). Adoptive cell transfer with autologous lymphocytes genetically engineered to express a T cell antigen receptor (TCR) for the HLA*0201 epitope of cancer germline antigen NY-ESO-1, led to durable tumor regression in some patients with metastatic melanoma. Unfortunately, targeting one antigen alone was shown to be not efficient enough to generate strong antitumor immune responses to mediate tumor rejection because of rapid appearance of escape mutants and novel somatic neo-antigens and the general inefficiency of monovalent cancer vaccines.

Recent interest in the potential of stem cells in regenerative medicine has made well-defined undifferentiated ESC lines widely available as well as undifferentiated iPSCs that are phenotypically and functionally similar to ESCs.

Cancer harboring stemness signature present a genomic plasticity with a profound change of the chromatin landscapes secondary to intrinsic pathways and inducing factors from a strong immunosuppressive tumor micro-environment. Their ability to de-differentiate into immature progenitors confer to tumor clones the re-expression of genes from fetal development with a down-regulation of CMH Class I and up-regulation of co-inhibiting molecules expression.

Thus, there continues to be a need for new approaches to prevent and/or treat cancers having stem cells signature. Vaccination against stem cell mutant neo-epitopes could be used to potentiate the immune response of adoptively transferred T cells or cells activated through immunological checkpoint blockade.

This and other needs are addressed in whole or in part by the presently disclosed subject matter.

SUMMARY OF THE INVENTION

The present invention relates a method for treating a subject suffering from a cancer, comprising a step of administrating simultaneously, separately or sequentially to said subject a therapeutically amount of (i) a histone deacetylase inhibitor (HDACi) and (ii) a vaccine composition containing an immunogenic element. Preferably, the immunogenic element is a population of fetal cells that have been inactivated, the fetal cells advantageously being in the same cellular differentiation lineage than the cancer to be treated. The present invention is defined in particular by the claims.

In one embodiment, the invention relates to a combination of (i) a histone deacetylase inhibitor (HDACi) and (ii) a vaccine composition containing a population of inactivated fetal cells for use in the treatment of a cancer in a subject. In another embodiment, the vaccine consists of a population of inactivated fetal cells. In particular, cells of the population express one or more antigen(s) of interest also expressed by the cancer cells of the subject. In a specific embodiment, the population of inactivated fetal cells is an organoid or is derived from an organoid (i.e. has been obtained by disrupting the 3D structure of the organoid).

It is preferred when the fetal stem cells have been obtained by a process comprising the steps of a. Differentiation of a population of pluripotent cells towards the pathway pertaining to the specific cancer of the patient,
b. Expansion of the cells thus differentiated,
c. Optionally exposition of to a mutagenic agent during expansion, to induce mutagenesis of genes in cells of said population,
d. Verification that at least 70% of the cells of the population express fetal markers,
e. Optionally verification that the cells of the population express at least one tumor associated antigen (TAA) or neo-antigen that is present in the subject's cancer cells, f. Inactivation of the cells, in order for the cells to lose their ability to divide.

When mutagenesis is performed, it is preferred when the mutagenic agent is selected from the group consisting of chemical mutagenic agents and radiation mutagenic agent (X-Ray, UV radiation). In particular, the mutagenic agent is selected from the group consisting of ENU, reactive oxygen species, deaminating agents, polycyclic aromatic hydrocarbons, aromatic amines and sodium azide.

In preferred embodiments, the histone deacetylase inhibitor is selected from the group consisting of Valproic acid (VPA), Vorinostat, Panobinostat, Givinostat, Belinostat, Entinostat, Mocetinostat, Practinostat, Chidamide, Quisinostat and Abexinostat.

The invention also relates to a composition of inactivated cells comprising inactivated fetal stem cells obtained from iPS-derived fetal hematopoietic lineage, wherein cells in said population present a mutation rate of at least 0.1% after expansion, in at least one gene selected from the group consisting of: ARHGEF10L, TRIM66, NKAIN, ITGAGGT1, PDZD, MUC4, MUC2, NECAB3, MNT, GLTSCR1, COPZ2, ZFP36, MIB2, ABCC12, IGFN1, LRRK2, RIN3, GGT1, ANK2, HDAC7, MUC20, SDCCAG3, DNAI1, BTNL9, ABTB2, MC2R, DOCK4, FSD1L, CRP, PPP1R3A, SLC22A17, PITPNM1, A2M, CTDSP2, IFNA14, KIF5C, THNSL2, GTF3C3, NRXN1, MED26, FNBP1, TMCO3, ING1, ZNF292, RBL1, CD109, FOXRED2, PLIN2, ZNF85, SESN1, CENPE, BTBD7, STOM, ZNF317, TET1, LRBA, MED4, CDC27, BCR, HPRT1, NASP, and MSH2. These genes are commonly expressed in acute leukemia, in particular in acute myeloid leukemia.

The invention also relates to a composition of inactivated fetal cells comprising inactivated fetal stem cells in iPS-derived renal organoid, wherein cells in said population express at least one fetal antigen selected from the following group: TRAPPC4, MX1, ITSN1, DNAJC7, TAF15, TMEM88, CRYM, PRTG, TYRO3 C12ORF60, FJX1, ADM, FAM45A, ASS1, CA2, ZFHX4, CLVS1, NRG1, EZH2, SLC22A23, MSH5, FBN2, GTF2H2, LIX1, HESX1, FZD5, LRP2, RHOQ, NUAK2, ILF2, ACP6, RPL5, NMNAT1, ID1, U2AF2, KLHL14, CDH2, GREBIL, ARRDC4, THBS1, BMP4, LRIG3, SOX5, SF1, LGR4, MGEA5, BCORL1, STOM, GLIS3, ANXA1, KDM4C, SDC2, TMEM130, MAGI2, GLI3, HEY2, TPBG, ID4, MYLIP, ENC1, EGR1, CDH6, NPY1R, SEL1L3, LRAT, CLDN1, CEP97, BHLHE40, ARL5A, ARL4C, ZNF385B, LYPD1, B3GNT7, INSIG2, ARHGAP29, NOTCH2, and IFI16. These genes are commonly expressed in primary adult renal carcinoma associated or not with c-Met mutation.

The invention also relates to a composition of inactivated fetal cells comprising inactivated fetal stem cells in iPS-derived lung organoid, wherein cells in said population express at least one fetal antigen selected from the following group: AIM2, AQP4, AURKA, BMP5, CDCA7, CEP55, CYP4B1, DACH1, EMP2, EPB41L4A, GJB2, MAOA, MELK, MKI67, NEBL, NFIA, PHF19, RNF144B, and UHRF1. These genes are commonly expressed in adult lung carcinoma.

The invention also relates to a vaccine composition comprising:
  a. a population of inactivated fetal stem cells and
  b. an agent that stimulates immune response and/or MHC I expression.

In particular, the inactivated fetal stem cells contain mutagenized fetal stem cells. It can be used for treatment of a cancer in a subject, especially when the cancer has fetal stem cells signature.

Also part of the invention is a kit comprising a vaccine composition as disclosed herein and an information leaflet providing instructions for immunization.

The invention also relates to a combined preparation of i) a population of inactivated fetal stem cells and ii) a compound which activates MHC expression and/or immune response for use by simultaneous, separate or sequential administration for treating a cancer in a subject. This can be used when the cancer is selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, renal carcinoma, head and neck tumor, and all sub-type of solid tumor and hematopoietic malignancies.

Methods of treatment wherein a therapeutic amount of the composition (inactivated fetal cell population and adjuvant) is administered to the patient in need thereof are also disclosed and part of the invention.

In the present application, all genes are indicated with their names as known by the person skilled in the art. From such names, one can find the sequence of the genes and proteins, by using any search engine (including generalist search engines) or in databases specific for maintaining libraries of cancer genes, such as the COSMIC database (Catalogue Of Somatic Mutations In Cancer, developed by the Sanger Institute in the UK) or the Cancer Genome Atlas (TCGA, maintained by the NCBI in the US). These databases regroup various sequences coding for antigens expressed in cancer cells.

DETAILED DESCRIPTION OF THE INVENTION

The inventors have shown that use of an HDACi together with a population of fetal stem cells led to a synergy and an efficient response of the immune system against tumor cells. They have also shown that a variety of HDAC inhibitors (HDACis), including verinostat, entinestat, leviteracetam and valproic acid, were able to act in synergy with a population of fetal stem cells so as to raise an efficient immune response against tumor cells. The inventors have also shown that vaccination of an individual affected with a cancer, such as a pancreatic cancer, with a combination of (i) fetal stem cells, such as irradiated endodermal progenitor cells (EndoPCs) and (ii) an HDACi, such as valproic acid, led to a drastic inhibition of the tumors and of a significant improvement of survival rate.

Indeed, inventors hypothesized that fetal stem cells derived from engineered iPSC as a source of fetal neoantigens could be used as a vaccine to generate an immune response against a variety of fetal antigens that are shared by tumor cells, and that this response could be more specific than a response obtained with pluripotent cells. They further hypothesized that the vaccination of mice with fetal stem cells in combination with an HDACi (e.g. valproic acid) would bolster the immune system and were able to demonstrate that this induced efficient immune and anti-tumoral responses without evidence of side effects and autoimmune diseases.

DESCRIPTION OF PRIOR ART DOCUMENTS

WO 2012/122629 discloses the combination of HDACi with a viral oncolytic vaccine expressing an antigen selected from the group consisting of include a tumour antigen: AFP), carcinoembryonic antigen (CEA), CA 125, Her2, dopachrome tautomerase (DCT), GP100, MART1, MAGE protein, NY-ESO1, HPV E6 and HPV E7. HDACi is an immunomodulateor to increase a secondary immune response after a primary immune response induced by a virus antigen (either from the virus or expressed by the virus).

Bartlett et al (Molecular Cancer 2013, 12:103) disclose oncolytic viruses (OVs) as therapeutic cancer vaccines. OVs armed immune-stimulatory genes induce potent anti-tumor immunity in animal models and human patients, in particular with co-administration with a HDAC inhibitor which inhibits innate immunity transiently to promote infection and spread of OVs. The role of the HDAV inhibitor (HDACi) is thus to increase the immune response by allowing the vector to propagate more efficiently.

Bridle et al (Molecular Therapy vol. 21 no. 4, 887-894 April 2013) disclose that HDAC inhibition suppresses primary immune responses, enhances secondary immune responses, and abrogates autoimmunity during tumor immunotherapy. The results are however obtained in the context of oncolytic viruses (OVs) as therapeutics applicable to a variety of malignancies, and only show that the HDACi was able to impair primary immune responses directed at the oncolytic vaccine vector and enhance the consequent secondary response.

Wu et al (J Ovarian Res. 2015 Oct. 24; 8:68) uses an established ovarian cancer cell line enriched in stem cells as a vaccine against the given cancer, without using any adjuvant.

WO 2016/065330 discloses the use of a modified stem cell comprising a cytotoxic payload; (ii) a wild-type or genetically modified virus; (iii) a wild-type or genetically modified bacteria; or (iv) a combination of two or more thereof for treating a solid tumor or hematologic malignancy in a subject. The description provides a list of stem cells that can potentially be used, without any details as to the actual nature or characteristics of these cells. This document doesn't describe nor suggests adding HDACi in order to generate the immune response against the cancer.

WO 2017/027757 discloses the use of a smallpox vaccine for treating a cancer in a subject wherein a stem cell could be added to this vaccine. The description provides a list of stem cells that can potentially be used, without any details as to the actual nature or characteristics of these cells. This document doesn't describe nor suggests adding HDACi in order to generate the immune response against the cancer.

EP 2 599 860 discloses an induced cancer stem cell which is an induced pre-cancer stem cell or an induced malignant stem cell, wherein the induced cancer stem cell expresses the six genes POU5F1, NANOG, SOX2, ZFP42, LIN28, and TERT; and has an aberration which is either (a) a mutation in an endogenous tumor suppressor gene or (b) increased expression of an endogenous cancer-related gene. In view of the expressed genes, this cell is not a fetal cell. In particular, POU5F1 and NANOG are markers of non-differentiation and pluripotency.

Zheng et al (Oncol Rep. 2017 March; 37(3):1716-1724) compares the vaccination with either hepatic stem cells (HSCs) or embryonic stem cells (ESCs). The HSCs were isolated from the liver of an adult mouse and are thus not fetal cells. Furthermore, no other adjuvant, in particular HDACi, was used in this study.

WO 2017/202949 discloses the use of pluripotent cells with an HDACi for treating cancer. Pluripotent cells are different from fetal cells, and do not express some antigens that are expressed in fetal cells and in cancers.

In summary, none of the above documents disclose the specific combination of an population of inactivated fetal cells (potentially mutated) together with an adjuvant (in particular HDACi or stimulating MHC-I expression) as a therapeutic or prophylactic vaccine against cancer.

Fetal Cell Composition and Method of Uses

The invention uses a population of fetal cells as an immunogen, and also relates to such.

In the present context, a population of fetal cell corresponds to a population of cells that are maintained as a cell culture, but also encompass organoids, where the cells are starting to create an organ and where a 3D spatial organization of the cells can be observed.

It is reminded that differentiation is the process by which a more specialized cell is formed from a less specialized cell. It is a continuous process. Starting from a pluripotent cell (embryonic stem cell, or iPS), the cells will lose the pluripotency, and engage into one way of differentiation, where it will mature in a fully differentiated specialized cell. For some organs, multiple cells will create organoids, during the differentiation process.

Inducing and directing the differentiation of pluripotent cells is known to the person of skill in the art. One can cite Wu et al (Cell. 2016 Jun. 16; 165(7):1572-1585), Fatehullah et al (Nat Cell Biol. 2016 March; 18(3):246-54) or Sasaki and Clevers (Curr Opin Genet Dev. 2018 Sep. 24; 52:117-122) that describe development or organoids from pluripotent cells. There are multiple other articles that describe and teach methods and conditions to have pluripotent cells differentiate in various tissues of interest.

Definition of a Fetal Cells Population

A fetal cell is a cell that has lost its pluripotency as it has started to engage in a differentiation pathway (endoderm, mesoderm, ectoderm).

It is possible to determine whether a population of cells is a population of fetal cells as the cells shall express fetal markers (see below) and not express pluripotency markers.

A population, according to the present invention, contains a large number of cells (at least $0.5 \times 10^6$ cells, more preferably at least $1 \times 10^6$ cells, more preferably at least $2 \times 10^6$ cells or $5 \times 10^6$ cells or more than $5 \times 10^6$.

In order to determine whether a population of cells is a population of fetal cells, one must:
  (a) Determine that the cells of the population essentially don't express pluripotency genes (or markers),
  (b) Determine the presence of fetal genes (or markers) expressed by cells of the population.

In a specific embodiment, the cells of the fetal cell population are such that there is
  (a) no cells or less than 10% of cells express genes typically expressed in undifferentiated pluripotent self-renewing cells (Embryonic Stem cells or induced Pluripotent Stem cells). this is preferably determined by flow cytometry and more specifically by FACS (Fluorescence-activated cell sorting)
  and
  (b) at least 70%, more preferably more than 75%, more preferably more than 80% of cells in the population express progenitor/fetal markers, regardless of whether the population is in the form of committed differentiated progenitors derived from three germline layers or of 3D-organoid tissues.

It is also preferred when less than 10% of cells express adult tissue markers. The adult tissue markers are markers (proteins or genes) that are expressed in adult cells.

The percentages mentioned above relate to the percentage of cells in the population that express the given markers. As an illustration, low expression (<10%) of master genes typically expressed in undifferentiated pluripotent self-renewing cells indicates that less than 10% of the cells of the population express the genes that are looked at, as further explained below.

It is reminded that the markers that are expressed vary during the differentiation process. Consequently, some markers associated with the fetal nature of the cells are expressed early in the differentiation process (i.e. quickly after loss of the pluripotency) whereas some markers are expressed late in the process (i.e. before the maturation in adult cells). Lack of expression of these fetal markers indicates that the cells have lost their fetal characteristics, and likely acquired a phenotype indicating that they have matured into differentiated adult cells.

In order to determine that (a) pluripotency genes aren't express by the cells of the population, it is possible to use gene expression and/or immunocytochemistry evaluation. The aim is to show absence or low expression of master genes typically expressed in undifferentiated pluripotent self-renewing cells (embryonic stem cells and Induced Pluripotent Stem cells).

In particular, one can:
a) use a population of iPS cells as a positive control for the markers of pluripotency, and
b) compare the expression level of a set of pluripotency genes in the target population and in the iPS cells population.

It is considered that the cells of the target population don't express pluripotency genes when the expression levels of the pluripotency genes is below 10%, more preferably below 5% of the expression level of these genes in the iPS cells population, or when less than 10%, more preferably less than 5% of the cells express the gene. Any quantitative method such as RT PCR or flow cytometry, or immune-histo-marking can be used. It is preferred to use FACS (Fluorescence-activated cell sorting) of cells. With this method, less than 10% of the cells of the population shall express these pluripotency genes.

There are multiple markers expressed by a pluripotent cell. In fact, when the cell loses its pluripotency character, it will also lose expression of these markers, as the expression of these pluripotency markers is correlated. Consequently, although multiple genes expressed by pluripotent cells (pluripotency genes) are known in the art, it is not necessary to study a large number of such.

In more details, it is preferred to study the expression of at least one pluripotency gene selected from the group consisting of NANOG, POU5F1 (Oct4), SSEA4, Tra-1-81, and Tra-1-60.

In one embodiment a combination of one intracellular (e.g., OCT4 or Nanog) and one extracellular (e.g., SSEA-4 or Tra-1-60 or Tra-1-81) could be used in order to improve the accuracy of the measure.

However, it is also possible when three of these genes, four or even five genes are looked at.

Determining the percentage of cells expressing these markers in the population is easily performed by the FACS method, with antibodies available in the art. It is even possible to perform this analysis in a multiplex experiment.

When multiple genes are studied, the percentage of cells considered as pluripotent in the population is determined by taking the mean of the percentages of cells harboring each marker.

As an illustration, if the percentage of cells of the given population expressing the gene (1) is 6%, and the percentage of cells of the given population expressing the gene (2) is 5%, it is considered that the population contains 5.5% of pluripotent cells (mean of 5% and 6%) and the given population will be considered as having passed condition (a) above.

In order to determine that the cells of the population express fetal genes and fulfill condition (b), it is necessary to detect genes (markers, proteins or antigens) that are express by the cells when they have entered in one of the differentiation pathway.

Neural Fetal Cells:
 Early neural ectoderm progenitors: TP63, MASH1, Notch1, Sox1, Sox2, Musashi 2, Musashi 1, Nestin, Pax6, MUC18, BMI1, Mash1, FABP7, Nucleostemin,
Hematopoietic Fetal Cells
 Hematopoietic mesoderm progenitors: Brachyury (T), MIXL1, cryptic, GATA1, LMO2, ACE, SCL(Tal1), HoxA9, Fli1
Renal Fetal Cells:
 Kidney mesoderm progenitors: WT1, HOXD11, SIX2, SALL1, WT1, PAX2, OSR1, PAX8, LHX1, GATA3, HOXB7
Liver Fetal Cells:
 Liver endodermic progenitors: SOX17, HNF3B, HNF6, Fox-A2, HNF1B GATA4, AFP, LGR5
Pancreatic Fetal Cells:
 Pancreatic endodermic progenitors SOX17, Fox-A2, CXCR4, GATA4, HNF1B, HNF4A, PDX1, HNF6, PROX1, Ngn3, NeuroD1, PAX6, SYP, SOX9, NKX2-2, NKX6-1, P48, LGR5, HB9
Intestinal Fetal Cells
 Intestinal endodermic progenitors: CDX2, TCF-2, SOX 9, NMYC, ID2, SOX2, PAX8, Nkx2.1, LGR5
Lung Fetal Cells
 Lung endodermic progenitors: CXCR4, SOX17, FOXA2, NKX2.1, PAX9, TBX1, SOX2 SOX9, ID2, Foxj1, Scgb1a1, Foxj1
Thyroid Fetal Cells
 Thyroid endodermic progenitors: CXCR4, SOX17, FOXA2, Pax8, HHEX, Nkx2-1
Other Fetal Cells
 Myoblast progenitors: Pax7, Pax3, Myf5
 Chondrocyte progenitors: Osteonectin, Sox9.
 Osteoblast progenitors: Runx2, ALP, Osx, Osteopontin, Osteocalcin.

The genes mentioned above are all known in the art and are specific for each differentiation pathway and for each tissue organoid. These fetal genes in early or late progenitors are not expressed in adult fully differentiated cells. as indicated, their sequence can be found in widley available public databases.

Consequently, these markers are markers of early ontogenetic development and reflect the fact that the cells harboring these markers are not fully adult mature cells. They are still progenitor cells from the fetal developmental phase, meaning that they can still produce various types of mature cells.

In the context of the invention, in order to obtain a fetal cells population, the person skilled in the art shall induce differentiation of pluripotent cells (such as Embryonic Stem cells or iPS cells) within one of the differentiation pathway, according to methods known in the art.

Loss of pluripotency will be verified by checking the loss of expression, in at least 90% of the cells, of the markers as indicated above.

Depending on the differentiation pathway selected by the person of skill in the art, it is possible to check presence of the specific fetal markers indicated above, in the cell population.

To do this, the person skilled in the art will use FACS analysis to measure the percentage of cells expressing the fetal markers of the given pathway, and will calculate the percentage by verifying that at least 70% of the cells express at least one of these markers. Using multiplex FACS analysis also makes it possible to identify the number of cells that express more than one marker. In other words, this means that the percentage of cells that don't express any of these markers is not more than 30%. This is also easily determined by FACS analysis.

It is also possible to determine whether the cell population is a fetal one, even without prior knowledge of the differentiation pathway of the cells.

To check whether a cell population is a fetal cell population according to the invention, one shall first look whether the cells express one or more of the pluripotency markers mentioned above (and the percentage of cells expressing said markers in the population). If less than 10% of the cells express the markers as mentioned above, the person of skill in the art can then look at the expression of fetal markers by the cells of the population.

The morphology/histology of the cells may provide information as to the cell lineage commitment to the person of skill in the art, thus making it possible to select a few markers for a first check. However, it is also possible to verify the fetal nature stage of the cells without pre-knowledge of the cell lineage commitment.

To do so, RNA from the cells of the population can be extracted, reverse transcribed, optionally amplified, and applied to any DNA chip or array that contains probes for fetal markers as mentioned above. One can use, in particular, a Low Density Array (LDA). This makes it possible, not only to determine the presence of fetal markers, but also to qualify these markers, i.e. to determine the differentiation pathway of the cells of the population (depending on the probes that are "turned on" by the RNA from the cell population).

Once the differentiation pathway is known, FACS analysis with the specific markers of this specific cell lineage differentiation pathway can be performed to quantify the percentage of cells expressing these markers in the population.

Use of a Fetal Cells Population

It has been long suggested that fetal antigens may be expressed in tumor cells (Ting et al, Proc Natl Acad Sci USA. 1972 July; 69(7): 1664-1668).

The inventors have now demonstrated that it is possible to use a population of fetal cells as disclosed herein for the prophylactic or therapeutic treatment of cancer in a subject. The inventors hypothesize that the onset and development of cancer may be due or promoted by mutations in the subject cells that induce de-differentiation and make them regress in the differentiation pathway to reach a new "fetal-like" character, and leads to proliferation of such. Consequently, such cells express fetal markers, which are not expressed in mature and fully differentiated adult cells. Furthermore, since these cells divide at a high rate, this induces mutations, that create mutated antigens, also called neo-antigens. It is actually to be noted that the fetal antigens or neo-antigens of tumor cells are generally shared between cancers, at least between cancers of organs originating from the same differentiation pathway (ectoderm, endoderm or mesoderm).

From the ectoderm pathway, the organs are epidermis skin cells, neurons, glial cells, neural crest; pigment cells.

From the mesoderm pathway, the organs are cardiac muscle, skeletal muscle cells, kidney (tubules), red blood cells, smooth muscle (in gut).

From the endoderm pathway, one can cite lung cells (in particular alveolar), thyroid cells, pancreatic cells, hepatic cells.

Finally, the microenvironment of cancer cells is generally favorable to the immune system as it will inhibit the action of T lymphocytes.

Administration of inactivated cells of these fetal cells population, preferably with a HDACi or with a compound increasing expression of MHC-I molecules, will make it possible to induce a immune response against the fetal antigen(s) present on the cells of the population in the subject (preferably a human being, but which can be another mammal, such as a dog, a cat, a cow or a horse), and hence against the tumor cells, thereby leading to regression of the cancer. It is valid for both solid tumors and tumors of the blood.

Indeed, cancer cells can express antigens (markers) such as the ones expressed by the cells of the fetal population herein disclosed and characterized.

Consequently, the population of fetal cells (fetal population) can be used to prime the immune system of a patient, in order for it to be able to adequately and efficiently fight the cancer.

The inventors noticed the presence of a synergistic effect when using both the HDACi (or an agent that increases MHC-I expression) and the population of inactivated fetal cells, which is believed to be due to one or more of:
  i) increase of MHC Class I expression on fetal cells and tumor cells to activate/boost the immune response (better presentation of fetal and neo-antigens)
  ii) increase of fetal antigens/neo antigens in Cancer Stem Cells (CSCs) and tumor cells by demethylation to induce a specific immune response against these antigens/neo antigens
  iii) increase of chemokine expression to recruit CD4+ and/or CD8+, and/or CD8+PD1− T lymphocytes into the tumor which makes the tumor immune-reactive
  iv) reduction of regulatory T lymphocytes and myeloid-derived suppressor cells (MDSC) in the tumor micro environment which makes the tumor immune-reactive.

In view of the different pathway, the populations of fetal cells can be used for treatment of lung, pancreas, kidney, breast, blood, gastro-intestinal, thyroid, prostate, brain (in particular glioblastoma) stomach, liver, bone, ovary cancers. One shall choose a population of fetal cells engaged into the same cellular differentiation lineage than the cancer to be treated.

Using such fetal cells population make it possible to deliver at least 10, more generally at least 50, or at least 100, 500, or even 1000 fetal or neo-antigens that are expressed in a given cancer or that are common to different cancers.

The fetal cells can contain mutations that are predisposing to familial cancers that express fetal genes deregulated by this mutation (BRCA, cMET, RET, APC etc.) and that are shared in cancers of the lineage, for instance, a iPS cell obtained from a blood cell containing the c-Met mutation can be derived as a kidney organoid that contains the c-Met mutation present in kidney cancers.

Use of a mutagenic agent when preparing the fetal cell composition (see below) shall introduce mutations (such as missense or frameshift mutations) in the genes of the cells of the population, and thus expression of neo-antigens.

In particular, the inventors have shown that an iPS cell obtained from a cell of a chronic myeloid leukemia (CML), mutated with ENU and derived in hematopoietic fetal cells contains antigens that are present in acute myeloid leukemia (AML).

In order to treat a patient, one can
i) obtain an antigen specific signature of the subject's cancer, from a biopsy of such cancer,
ii) select a population of inactivated fetal cells that contain cells that express at least one of the antigen determined in step i),
iii) administer this population to the patient, together with an HDACi or an agent that increases MHC-I expression.

Step i) is performed by methods known in the art, using tools that are available in the art.

The signature is obtained, in particular, by
determining the genes expressed in the cancer cells (exome sequencing),
comparing the genes to a database of cancer specific genes (one can cite, in particular the COSMIC database (Catalogue Of Somatic Mutations In Cancer, developed by the Sanger Institute in the UK) or the Cancer Genome Atlas (TCGA, maintained by the NCBI in the US). These databases regroup various sequences coding for antigens expressed in cancer cells,
selecting the genes that are present in both the exome and the database as an antigen specific signature of the cancer.

Step ii) is performed by performing an exome of a fetal cell population and verifying that at least one of the genes of the antigen specific signature of the cancer is present in the exome obtained from the fetal cell population.

In another embodiment, one can
i) obtain an antigen specific signature of the subject's cancer, from a biopsy of such cancer,
ii) select a population of inactivated fetal cells that contain cells that commonly express at least one of the antigen determined in step i),
iii) administer an extract of this population to the patient, together with an HDACi or an agent that increases MHC-I expression.

In this embodiment, the extract is selected from total RNA, mRNA, DNA, protein extract, lysate, freeze-dried extract, lyophylisate or dessicate cells, exosomes, extracellular microvesicules, and apoptotic bodies.

In another embodiment, one can
i) obtain an antigen specific signature of the subject's cancer, from a biopsy of such cancer,
ii) select a population of inactivated fetal cells that contain cells that commonly express at least one of the antigen determined in step i),
iii) administer to the patient a population of T-cells or of antigen presenting cells that have been primed in vitro with the population of ii) or an extract of such population, in presence of an HDACi or an agent that increases MHC-I expression.

In a specific embodiment, said population has been obtained by:
a. Differentiation of a population of pluripotent cells towards the pathway pertaining to the specific cancer of the patient, wherein the pluripotent cells have optionally been expanded in presence of a mutagenic agent,
b. Expansion of the cells thus differentiated,
c. Optionally exposition of to a mutagenic agent during expansion, to induce mutagenesis of genes in cells of said population,
d. Verification that at least 70% of the cells of the population express fetal markers,
e. Optionally verification that the cells of the population express at least one cancer or neo-antigen that is present in the subject's cancer cells,
f. Inactivation of the cells, in order for the cells to lose their ability to divide.

Using a fetal cells population according to the invention is particularly interesting. Indeed, these cells contain a multitude of fetal antigens susceptible to be expressed by cancer cells.

The invention also relates to a method to develop and produce a population of cells intended to be used for the treatment of a cancer in a patient.

The method comprises the steps of
a) Optionally performing a biopsy of the cancer,
b) Analyzing the cells recovered from a cancer biopsy from the patient to identify fetal and cancer markers expressed by cancer cells,
c) Differentiation of a population of pluripotent cells through the pathway pertaining to the specific cancer of the patient (for instance, if the patient has a kidney cancer, differentiation on the kidney pathway will be induced),
d) Optionally introduction of mutations in the population of differentiated cells: such step is optional but preferably performed. It is intended to increase the diversity of the antigens expressed by the cells of the population, to improve the ability of the immune system, upon exposition to the cells, to control the cancer cells even in presence of mutations of the cells thereof. The rate of mutation can be controlled by checking the sequence of one or more genes of the cell population. It is possible to identify the presence of mutated sequences of a given gene within the population and quantify such as compared to the sequences of the gene in the population. For instance, a mutation rate of 0.1% for a given gene indicates that 0.10% of the sequences identified, for this gene, in the population, present a mutation,
e) Optionally verifying that the cells of the population express at least one cancer or neo-antigen that is present in the subject's cancer cells,
f) Inactivation of the cells, in order for the cells to lose their ability to divide. This is to avoid proliferation of the cells in vivo after all or part of the cell population is administered to the patient.

Once the cell population has been obtained, of all or part of it can be administered to an animal (preferably a mammal, more preferably a human being), preferably in presence of a HDACi or a compound stimulating expression of MHC-I. As indicated above, in all methods, one can administer the inactivated fetal cell population, or an extract thereof, or T-lymphocytes or antigen presenting cells primed with the population or an extract thereof.

In a specific embodiment, the pluripotent cells of step c) are iPS cells (Induced pluripotent stem cells) that have been developed from cells of the patient. This may reduce the risk of cross-immunity when the fetal cells are administered to the patient. Indeed, the non-fetal antigens shall not be recognized by the immune system, whereas the fetal antigens (present on the cells of the population and on cancer cells) shall be recognized.

Alternatively, the invention relates to a method for treating a patient, comprising the steps of
a) Optionally performing a biopsy of the cancer,
b) Analyzing the cells recovered from a cancer biopsy from the patient to identify fetal and cancer markers expressed by cancer cells,
c) Selecting a population of inactivated and optionally mutagenized fetal cells engaged in the differentiation pathway pertaining to the specific cancer of the patient,
d) Administering the cells to the patient, an HDACi or a compound that stimulates or increases MHC-I expression.

In a specific embodiment, the fetal cells are engaged in the lung differentiation pathway. They would thus express the markers as indicated above for lung. These cells are particularly adapted for the treatment of lung cancer.

In a specific embodiment, the fetal cells are engaged in the thyroid differentiation pathway. They would thus express the markers as indicated above for thyroid. These cells are particularly adapted for the treatment of thyroid cancer.

In a specific embodiment, the fetal cells are engaged in the kidney differentiation pathway. They would thus express the markers as indicated above for kidney. These cells are particularly adapted for the treatment of kidney cancer.

In a specific embodiment, the fetal cells are engaged in the hematopoietic differentiation pathway. They would thus express the markers as indicated above for hematopoietic cells. These cells are particularly adapted for the treatment of blood cancer (leukemia).

In a specific embodiment, the fetal cells are engaged in the liver differentiation pathway. They would thus express the markers as indicated above for liver. These cells are particularly adapted for the treatment of liver cancer.

In a specific embodiment, the fetal cells are engaged in the intestinal differentiation pathway. They would thus express the markers as indicated above for intestinal. These cells are particularly adapted for the treatment of gastro-intestinal cancer.

In a specific embodiment, the fetal cells are engaged in the pancreatic differentiation pathway. They would thus express the markers as indicated above for pancreas. These cells are particularly adapted for the treatment of pancreatic cancer.

In a specific embodiment, the fetal cells are engaged in the neural differentiation pathway. They would thus express the markers as indicated above for neurons or brain. These cells are particularly adapted for the treatment of brain cancer (in particular glioblastomas).

In a specific embodiment, the fetal cells are engaged in the bone differentiation pathway. They would thus express the markers as indicated above for osteoblast. These cells are particularly adapted for the treatment of bone cancer.

HDACi for Improving Immune Response

In a first aspect, the invention relates to a method for increasing efficacy, in a subject, of a vaccine composition, comprising the step of administering an HDACi to the subject together with the vaccine composition. In particular, the HDACi is added to the vaccine composition.

This invention also pertains to a combination of (i) a histone deacetylase inhibitor (HDACi) and (ii) a vaccine composition containing an immunogenic element for use in the treatment of a cancer in a subject. According to some embodiments, this invention pertains to a combination of (i) a histone deacetylase inhibitor (HDACi) and (ii) a vaccine composition containing an immunogenic element, by simultaneous, separate or sequential administration, for use in the treatment of a cancer in a subject.

This invention also concerns the use of a combination of (i) a histone deacetylase inhibitor (HDACi) and (ii) a vaccine composition containing an immunogenic element for preparing a pharmaceutical composition for treating a cancer in a subject. According to some embodiments, this invention concerns the use of a combination of (i) a histone deacetylase inhibitor (HDACi) and (ii) a vaccine composition containing an immunogenic element, for simultaneous, separate or sequential administration, for preparing a pharmaceutical composition for treating a cancer in a subject.

As used herein, the term "increased efficacy" refers to an increasing immunogenicity of the vaccine composition, increasing the immune response against the vaccine composition, or increasing the immune response generated by the vaccine composition. This can be compared to the immune response generated in the absence of HDACi.

The vaccine composition contains an immunogenic element intended to make the subject develop an immune response against one or more antigen(s) of interest. An antigen of interest are any antigen against which an immune response is desired, and include any peptide, protein either from the self (such as antigens from cancer cells) or exogenous such as bacterial, viral, or parasitic protein, other kind of antigens such as nucleic acids, sugars, lipopolysaccharides and the like.

The invention thus relates to the use of an HDACi as an adjuvant, in particular for increasing the immune response against a vaccine composition, as well as to HDACi for its use as an adjuvant, or for increasing the immune response against a vaccine composition. The invention also relates to the use of an HDACi for the manufacture of a vaccine composition containing one or more antigen(s) of interest, intended to have the subject develop an immune response against the antigen(s) of interest.

The method and use herein disclosed are particularly interesting when the vaccine composition is a cancer vaccine composition, i.e. contains antigen(s) of interest that are expressed by cancer cells. In particular, the method and use are very adapted for tumors with a particularly immunosuppressive tumor micro-environment (i.e. there are an expression of cytokines and of molecular signals, and recruitment of immune tolerant cells that the potency of immune cells against the cancer antigens is decreased). Without being bound by this theory, it is postulated that the presence of the HDACi will modify the tumor micro-environment and allow the immune cells to be potentiated to fight the cancer cells, probably by modifying expression of the genes that have an immunosuppressive effect in the cells that are present in, near or around the tumor.

The method herein described may also comprise the step of administering an HDACi for a few days after the administration of the vaccine composition. This continuous administration of an HDACi can be useful for maintaining the microenvironment modification for a time long enough for the immune cells to be able to "take over" the tumor. Generally, this further continuous administration of the HDACi will consist in a daily administration of an adequate dose of the HDACi, for at least three days following vaccine administration, and up to one month. It is, however preferred when the further HDACi administration is performed for at least one week, more preferably at least or about two weeks.

The vaccine composition contains an immunogenic element (also termed immunogenic compound herein) intended to make the subject develop an immune response against one or more antigen(s) of interest.

This immunogenic element may be an antigen (or multiple antigens). This antigen can be, as seen above, of any form, depending on the target cells (which is intended to include host cells, as well as bacterial cells, parasitic pathogens or viral particles). It can also be formulated with any adjuvant (immune-stimulant) known in the art such as alum or Freund's complete or incomplete adjuvants.

In another embodiment, the immunogenic compound is an extract from a cell composition, wherein cells of said composition express an antigen of interest. The cellular extract may be lysed cells that have been centrifuged to remove insoluble matter such as membrane fragments, vesicles, and nuclei, and thus consist mostly of cytosol. In another embodiment, the extract may have been made using specific techniques to deplete or enrich specific components (for example sonication can be used to break large membrane fragments into small particles that remain in the extract, or high speed centrifugation to remove the smallest insoluble components). The cell extract is obtained by any chemical or mechanical action, such as by pressure, distillation, evaporation and the like.

In another embodiment the immunogenic element is a cell composition, wherein cells of said composition express the antigen of interest. In a particular embodiment, the membrane of the cells is preserved (so that presentation of the antigen is made through the MHC-I pathway). In a particular embodiment, the cells are inactivated, as described below. In a particular embodiment, the cells are fetal stem cells, as described below, cancer stem cells, virus-infected cells or bacterial cells. In another embodiment, the immunogenic element is a cell composition comprising Antigen-Presenting-Cells (APCs) that have been primed in vitro by antigens of interest. This composition is an antigen-presenting cell vaccine, made of antigens and antigen-presenting cells (APCs). Antigen-presenting cells are cells that display antigen complexed with major histocompatibility complexes (MHCs) on their surfaces. One can cite dendritic cells (DC), which are preferred in the context of the invention, as they are able to present antigen to both helper and cytotoxic T cells, macrophages, or B cells. These APCs may be natural cells, or engineered cells. One can, in particular, cite Eggermont et al (Trends in Biotechnology, 2014, 32, 9, 456-465) which review advances in developing artificial antigen-presenting cells. Methods of developing anti-cancer vaccines, using APCs, have been widely proposed in the art and are known by the person skilled in the art.

In another embodiment, the immunogenic element does not actually contain an antigen, but consists in a composition of T cell lymphocytes that have been primed in vitro against the antigen of interest, for instance by exposure to Antigen-Presenting-Cells presenting the antigen of interest. Consequently, this composition is able to onset an immune response in vivo against the antigen of interest. This strategy can be called "adoptive transfer of T cells", and it is known that such adoptively transferred T cells persist for long periods of time in vivo and readily migrate between the lymphoid and vascular compartments (Bear et al, J Biomed Biotechnol. 2011; 2011:417403; Melief et al, J Clin Invest. 2015; 125(9):3401-3412).

In some embodiments, the HDACi is administered in combination with the vaccine composition containing the immunogenic element. Said administration may be simultaneous, separate or sequential, as disclosed below for the embodiment where the immunogenic element is a composition of fetal stem cells. It is to be noted that all descriptions below, that are disclosed for the composition of fetal stem cells are equally applicable to the vaccines comprising any immunogenic element as disclosed above.

The present specification emphasizes an HDAC inhibitor (in particular valproic acid), together with a composition of fetal stem cells, as such fetal stem cells express neo-antigens that are also found in very aggressive cancers, as reminded above. Consequently, whatever the immunogenic element, it is preferred when the antigen of interest is a neo-antigen that is expressed by cancer cells, as described above and also below.

In a particular embodiment, the immunogenic element is a cell composition, wherein the fetal cell composition has been obtained from pluripotent stem cells and inactivation of fetal cells, as further disclosed in details below.

As used herein, the term the "immunogenic element" refers to compounds which stimulate the immune system. In the context of the invention, the immunogenic element is selected from the group consisting of:
  a. an antigen of interest,
  b. a fetal stem cell composition,
  b. an extract from a cell composition, wherein cells of said composition express an antigen of interest,
  c. a cell composition, wherein cells of said composition express an antigen of interest,
  d. a cell composition comprising Antigen-Presenting-Cells that have been primed in vitro by antigens of interest, or
  e. T cell lymphocytes that have been primed in vitro against the antigen of interest by exposure to Antigen-Presenting-Cells presenting the antigen of interest.

In a particular embodiment, the immunogenic element is a cell composition, wherein cell composition has been obtained by in vitro differentiation of pluripotent stem cells (ESC and iPSC). More particularly, the immunogenic element is a population of fetal stem cells obtained from ESC and iPSC by differentiation.

The method according to the invention, wherein the treatment is a therapeutic treatment.

The method according to the invention, wherein the treatment is a prophylactic treatment.

Method of Treating a Subject Suffering from a Cancer with a Combined Preparation In a second aspect, the present invention relates a method of treating a subject suffering from a cancer comprising a step of administration simultaneously, separately or sequentially to said subject a therapeutically amount of i) a population fetal stem cells and ii) a compound selected from a group which activates MHC expression and/or immune response, as a combined preparation.

In a particular embodiment, the cells have been cultured so as to present neo-antigens through the MHC I pathway and, in particular, some cells of the population present are mutated. The compound used in combination with the fetal cells does not preserve pluripotency of the pluripotent stem cells. In a particular embodiment, the administration of the fetal cells is followed by administration of a compound which activates MHC expression and/or immune response (preferably the same than the one that has been initially administered in combination, but potentially another one) to enhance immune response.

As used herein, the terms "treating" or "treatment" refer to both prophylactic or preventive treatment as well as curative or disease modifying treatment, including treatment of subject at high predisposed risk of contracting cancer such as hereditary family cancer syndromes or suspected to have contracted a cancer as well as subject who are ill or have been diagnosed as suffering from a cancer or medical condition, and includes suppression of clinical relapse. The treatment may be administered to a subject having a cancer or who ultimately may acquire the cancer, in order to prevent, cure, delay the onset of, reduce the severity of, or ameliorate one or more symptoms of cancer or recurring cancer, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, (e.g., weekly, monthly, yearly, etc.) or intermittent therapy (e.g., interrupted treatment, intermittent treatment, treatment at relapse, or treatment upon achievement of a particular predetermined criteria (e.g., pain, disease manifestation, etc.).

As used herein, the term "administration simultaneously" refers to administration of 2 active ingredients by the same route and at the same time or at substantially the same time. The term "administration separately" refers to an administration of 2 active ingredients at the same time or at substantially the same time by different routes. The term "administration sequentially" refers to an administration of 2 active ingredients at different times, the administration route being identical or different.

As used herein, the term "subject" refers to any mammals, such as a rodent, a feline, a canine, and a non-human and human primate. Particularly, in the present invention, the subject is a human afflicted with or susceptible to be afflicted with cancers which having an expression of fetal-like stem cell antigens.

As used herein, the term "population" refers to a population of cells, wherein the majority (e.g., at least about 20%, preferably at least about 50%, more preferably at least about 70%, and even more preferably at least about 80%, and even more preferentially at least about 90%) of the total number of cells have the specified characteristics of the cells of interest (e.g. fetal stem cells markers).

As used herein, the term "a population of fetal stem cells" refers to a population of fetal cells which are transient progenitors appearing during the early stage of development. This kind of population can be reproduced in vitro by differentiation of allogeneic, xenogeneic or syngeneic pluripotent stem cells (ESC and iPSC). Fetal population cells are characterized by the loss of genes related to pluripotency with at least 20% of loss of the following genes NACC1, BLM, WDR33, DAZAP1, CDK1, CDC45, ZNF165, XRCC5, SMARCADI, AIMP2, CKS1B, NANOG, ZFP42, U2AF1, CCNB2, DCTPP1, TGIF1, SUPT3H, AURKB, GEMIN7, SRSF1, PNP, SIGLEC12, POU5F1, PSMA3, RMND5B, GDF9, STXBP2, BAG6, GMPS, PCNA, NME1, POP7, RCHY1, SMARCC1, HNRNPK, PTMA, NPM1, SNRPA, MYBBP1A, CDT1, HSPD1, TRIM28, PHF10, GRB7, HSPE1, DAXX, FAM136A, KPNA2, FUS, PNN, RFC3, HPRT1, PA2G4, SNRPE, RBPMS, PRMT5, PIAS2, BYSL, POLD2, LSM5, TDGF1, NOP56, EPPK1, TARBP2, MRE11A, CDC7, SRSF3, TNNI3, NUDT1, DIAPHI, PPID, CDA, GADD45A, MCM6, SNURF, CDC25C, TNFRSF8, STIP1, ACTA1, POLR1D, TUBA3C, RPA1, VAMP8, UNC119, COIL, BIK, PARP1, SP1, CHEK2, NLE1, RPA2, HDAC1, KPNB1, LSM7, TMSB4Y, HMGA1, POLR1C, LSM1, EXO1, MCM5, ITGB3BP, LSM6, UNG, PSMA6, CCNE1, SMNDC1, SET, FKBP3, TK1, CTBP2, POLQ, PLSCR1, GMNN, RND1, NUP153, PHGDH, SNRPB, HSPA14, HSPH1, TCOF1, ANP32A, PELP1, MBD2, HIST1H2BC, TMPO, SPAG5, DNMT3B, LCK, ARMC6, COPS6, MCM3, PPAP2C, LSM4, NME1-NME2, EWSR1, POLG2, BCL2, NFKBIB, SALL4, PXN, EXOSC8, HSPA2, HMGB1, RUVBL1, GOT2, PPM1B, ATIC, DHCR24, APEX1, RFC2, WDYHV1, NTHL1, EXOSC7, SNRPD1, DPPA2, MRPS12, FBL, POLD1, MCM10, EXOSC3, NOP58, TPX2, PAK3, HNRNPAB, ANXA2, BUB1B, SEPHS1, WDR77, LUC7L3, VASP, MCM4, PAKI, PMAIP1, PBX1, NOLC1, PCYT1B, NCL, ORC6, GPRIN2, ORC1, RAD51, HSPA8, ANXA3, NUP50, SNRPC, HAUS1, MATK, BIRC5, MYC, GEMIN6, PSIP1, DSCC1, STRBP, SMN1, EXOSC9, TOE1, GEMIN2, TRIP13, ORC2, MSH3, MNAT1, KIT, RFC5, FOXO4, AATF, RBM14, ZNF281, NPPB, RPA3, APOE, PFDN6, COPS3, CCND1, CXADR, MCM2, ANAPC1, SUMO1, SSB, HSP90AB1, TRAIP, PHC1, LRIF1, LSM3, SNRPN, RPP40, MSH2, FBP1, PFN1, OTX2, STX3, STXBP3, GTF2H2, ELAC2, TCERG1, ERCC5, PASK, ZNF593, PSME3, WRN, ARID3B, ERBB3, POP1, KAT7, PTPN6, SYNCRIP, SIRT1, SLC19A1, ARL4A, CEBPZ, MSH6, AURKA, BAK1, MTHFD1, HSPA9, MYBL2, POP5, RFC4, CHEK1, BCCIP, SOCS1, PHB, PMF1, MPP6, NOC2L, HDAC2, CENPE, RECQL4, CASP6, GNL3, SRSF2, BRIX1, MYB, RNMTL1, DHFR, FEN1, SNRPF, MUTYH, PRNP, MT1G, PSMD11, GAR1, DDX11, FUBP1, CDK7, WRAP73, CASP9, RASL11B, CHAF1A, CCNB1, CKS2, CCNA2, PPAN, WEE1, TP53, HMMR, TDP2, RAD9A or RAD54L. In particular, the fetal stem cells are also characterized by the absence of expression of lineage specific genes of adult differentiated cells.

In a particular embodiment, the population of fetal stem cells can be obtained by direct conversion of adult somatic cells by de-differentiation procedure or by trans-differentiation technology using small molecules and/or by the over expression of specific transcription factors. These calling induced fetal population cells are characterized by the acquisition of fetal genes and by the loss of lineage specific genes of adult cells. All fetal population cells are derived from the three germ layer, respectively the ectoderm, endoderm and mesoderm progenitors. These fetal genes are represented:

1) In endoderm progenitor cells, at least by SOX17, CXCR4, FOXA1, FOXA2, FOXA3, HHEX, GATA4, GATA6, HNF1B, HNF4A, TF, ALB, TBX3, AFP, TTR, CER1, MIXL1, LHX1, GSC, PAX9, NEPN, SHH, PYY, MNX1, KITL, CLDN4, CLDN8, GFPT2, KRT19, SORCS2, EPPK1, NEDD9, PLAT, VTN, PDX1, TMPRSS4, CLIC6, RIPK4, CLDN8, ST1A;
2) In ectoderm progenitor cells at least by PCGF4, PAX6, PAX7, CXCR4, SOX1, SOX2, SOX10, ITGB1, FABP7, NES, FUT4, PROM1, MELK, MSI1, MAP2, DCX, NCAM1, TUBB3, SLC1A3, CD44, S100B, VIM, GFAP, CNP, OLIG2, CA2, CSPG4, TAZ, MSX1, SPARC, ID2, NES, NKX2.2, NKX6-1, FOXP2, FOXD3, ZIC1; and 3) In mesoderm progenitor cells at least by Brackury (T), MIXL1, SNAI1, SNAI2, HLX, EOMES, MESP1, MESP2, TBX6, MEST, NKX2-5, KDR.

Typically, the fetal population cells express fetal developmental genes that are not expressed in adult stage. These fetal genes are linked to a committed fetal cellular lineage or differentiated tissue such as 3D organoid structure or embryoid body or spheroid or cell aggregates. These fetal cells may be: neural stem cells, neurons, hepatocyte-like cells, hepatoblast, nephron renal progenitor cells, pancreatic endodermic progenitors, cholangiocyte, hematopoietic progenitors, hemangiobast, mesenchymal stem cells, endothelial cells, cardiomyocytes, neural crest progenitors, mammary epithelial cells, intestinal or colon organoid, lung organoid, kidney organoid, brain organoid.

As used herein, the term "pluripotent" refers to cells with the ability to give rise to progeny that can undergo differentiation, under appropriate conditions, into all cell types derived from the three germ layers (endoderm, mesoderm, and ectoderm) with specific cell lineages characteristics. The term "pluripotent" includes normal embryonic stem cells (ESCs), or very small embryonic-like stem cells (VSELs) or engineered induced pluripotent stem cells (iPSCs), reprogrammed from all sources and cell origins of adult somatic cells (ASCs).

Pluripotent stem cells contribute to fetal development of tissues of a prenatal, postnatal or adult organism. Standard art-accepted tests are used to establish the pluripotency of a cell population such as the ability to form a teratoma in 8-12 week old SCID mice, and various pluripotent stem cell characteristics. More specifically, human pluripotent stem cells express at least some (at least three, more generally at least four or five), and optionally all, of the markers from the following non-limiting list: SSEA-3, SSEA-4, TRA-1-60, TRA-1-81, TRA-2-49/6E, Alkaline phosphatase (ALP), Sox2, E-cadherin, UTF-I, Oct4, Lin28, Rex1, Nanog, TERC, TERT.

Pluripotent stem cells traditionally arise from the blastocyst stage of embryonic development and have the ability to develop into all types of fetal and adult cells except perhaps for placenta. Embryonic pluripotent stem cells (ESC) generally can be isolated from a 50- to 150-cell, 4- to 5-day-old post-fertilization blastocyst. While ESCs are capable of indefinite ex vivo proliferation, they exist only transiently in vivo during embryogenesis. Various animal (including human) ESC lines, such as, for example, NIH approved cell line WAO9 human ESCs can be obtained commercially from WiCell Research Institute, Madison, Wis. Human ESC lines, such as Cecol-14, can be obtained commercially for example from Cecolfes, Bogota, Colombia. Of course, other embryonic stem cell lines may be used, if desired.

As used herein, the term "Embryonic stem cell" refers to pluripotent cells of humans (i.e., hESC). The hESC are isolated from a pre-blastocyst stage embryo. In another embodiment, the hES cells are prepared by dedifferentiation of at least partially differentiated cells (e.g., multipotent cells) and are totipotent in practice. Methods of preparing hESC are well known and taught, for example, in U.S. Pat. Nos. 5,843,780, 6,200,806, 7,029,913, 5,453,357, 5,690, 926, 6,642,048, 6,800,480, 5,166,065, 6,090,622, 6,562,619, 6,921,632, and 5,914,268, U.S. Published Application No. 2005/0176707, International Application No. WO2001085917. In the context of the invention, the human embryonic stem cell (hESC) are generated without embryo destruction according to the technology as described in Chung et al 2008.

In a particular embodiment, the fetal population cells according to the invention are obtained by in vitro methods such as by differentiation of pluripotent stem cells such as ESC and iPSC. As used herein, the term "induced pluripotent stem cell" refers to a pluripotent stem cell artificially derived from a non-pluripotent cell by a reprogramming procedure, using methods known in the art and initially disclosed by Yamanaka (in particular WO2012/060473, PCT/JP2006/324881, PCT/JP02/05350, U.S. Pat. Nos. 9,499,797, 9,637,732, 8,158,766, 8,129,187, 8,058,065, 8,278,104. In short, somatic cells are reprogrammed to induced pluripotent stem cells (iPSCs) by ectopic expression of defined factors such as Oct4, Sox2, Klf4 and c-My, or Oct4, Sox2, Lin28 and Nanog. In a particular embodiment, the induced pluripotent stem cells are derived from mammals in particular (but not limited to) rodents, pigs, cats, dogs, and non-human primates, and human.

iPSCs have been successfully generated from somatic normal cells of various origins (fibroblast, blood cells, keratinoctytes . . . ) and from various disease such as, somatic or hereditary cancer (leukemia, glioblastoma, melanoma, breast cancer, . . . ) and genetic diseases. Cellular reprograming can be performed by variable technologies (such as integrative lentivirus/retrovirus and non integrative vectors such as sendai of virus, episomal vectors, synthetic mRNA, Adenovirus, rAAV, recombinant proteins . . . ) with or without small chemical compounds. Small molecules can be used to enhance induction and quality of mouse and human iPSCs by acting as epigenetic modifiers (i.e. modifying expression of some genes).

As an illustration, one can cite BIX01294 (BIX, a G9a histone methyltransferase inhibitor), sodium butyrate (NaB, an histone deacetylase HDAC inhibitor) or S-adeno-sylhomocysteine (SAH, a DNA demethylation agent), 5-azacytidine (5-AZA, a DNA methyltransferase inhibitor), Valproic acid (VPA, another histone deacetylase inhibitors) also improves reprogramming and quality of normal iPSCs. Fully reprogramed bona-fide iPSC express similarly pluripotent genes than embryonic stem cells with self-renewal capacity and represent an unlimited stem cell (or stem cell like) resource. ESC and IPSC can be amplified iteratively during multiple and illimited passages allowing scalable stem cells resources. Pluripotency potential is actively maintained in permissive culture conditions, by preserving high level expression of pluripotency genes. These methods are known in the art. Specific culture conditions and methods allow to replicate a stable genome, but some exome mutations and epigenomic modifications have nevertheless been described (Gore A and al. Nature 2011).

As used herein, the term "somatic cell" refers to any cell of the body except germline cells (sperm and egg). As used herein, the term "allogeneic cells" refers cells from the same species but genetically distinct. As used herein, the term "syngeneic or autologous cells" refers to cells from the same species and the same genetic background. As used herein, the term "xenogeneic cells" refers to cells from different species and genetically distinct. In a particular embodiment, the stem cells can be derived from mammals but not limited to rodents, pigs, cats, dogs, and primates, including humans.

Method for Producing Fetal Stem Cell Composition:

In a third aspect, the invention relates to a method for producing a fetal cell composition, comprising the steps of:

i) Fetal stem cells in the presence of an agent that induces MHC-I presentation of antigens in said population after pluripotent stem cell differentiation, ii) Exposing the fetal stem cells to an inactivating agent that will inactivate the cells, iii) Recovering and conditioning the differentiated inactivated fetal stem cells.

In a specific embodiment the fetal stem cell envelope integrity is maintained in step ii). In another embodiment, the fetal stem cells are inactivated and a cell derived product is obtained, such as cell extracts. The cell composition produced according to the method above can be used for cancer treatment, according to the methods disclosed herein.

Preparing of Fetal Stem Cells:

Fetal stem cells or fetal organoids are obtained from pluripotent stem cells after inducing differentiation, by the classical methods (e.g. in defining culture conditions using small molecules, morphogenic and growth factors in 2D or 3D culture system). The fetal stem cells or organoids loss the pluripotency markers. Typically, the fetal stem cells or organoids are depleted at least 20% of the following genes which are characteristic of pluripotency: NACC1, BLM, WDR33, DAZAP1, CDK1, CDC45, ZNF165, XRCC5, SMARCADI, AIMP2, CKS1B, NANOG, ZFP42, U2AF1, CCNB2, DCTPP1, TGIF1, SUPT3H, AURKB, GEMIN7, SRSF1, PNP, SIGLEC12, POU5F1, PSMA3, RMND5B, GDF9, STXBP2, BAG6, GMPS, PCNA, NME1, POP7, RCHY1, SMARCC1, HNRNPK, PTMA, NPM1, SNRPA, MYBBP1A, CDT1, HSPD1, TRIM28, PHF10, GRB7, HSPE1, DAXX, FAM136A, KPNA2, FUS, PNN, RFC3, HPRT1, PA2G4, SNRPE, RBPMS, PRMT5, PIAS2, BYSL, POLD2, LSM5, TDGF1, NOP56, EPPK1, TARBP2, MRE11A, CDC7, SRSF3, TNNI3, NUDT1, DIAPHI, PPID, CDA, GADD45A, MCM6, SNURF, CDC25C, TNFRSF8, STIP1, ACTA1, POLR1D, TUBA3C, RPA1, VAMP8, UNC119, COIL, BIK, PARP1, SP1, CHEK2, NLE1, RPA2, HDAC1, KPNB1, LSM7, TMSB4Y, HMGA1, POLR1C, LSM1, EXO1, MCM5, ITGB3BP, LSM6, UNG, PSMA6, CCNE1, SMNDC1, SET, FKBP3, TK1, CTBP2, POLQ, PLSCR1, GMNN, RND1, NUP153, PHGDH, SNRPB, HSPA14, HSPH1, TCOF1, ANP32A, PELP1, MBD2, HIST1H2BC, TMPO, SPAG5, DNMT3B, LCK, ARMC6, COPS6, MCM3, PPAP2C, LSM4, NME1-NME2, EWSR1, POLG2, BCL2, NFKBIB, SALL4, PXN, EXOSC8, HSPA2, HMGB1, RUVBL1, GOT2, PPM1B, ATIC, DHCR24, APEX1, RFC2, WDYHV1, NTHL1, EXOSC7, SNRPD1, DPPA2, MRPS12, FBL, POLD1, MCM10, EXOSC3, NOP58, TPX2, PAK3, HNRNPAB, ANXA2, BUB1B, SEPHS1, WDR77, LUC7L3, VASP, MCM4, PAKI, PMAIP1, PBX1, NOLC1, PCYT1B, NCL, ORC6, GPRIN2, ORC1, RAD51, HSPA8, ANXA3, NUP50, SNRPC, HAUS1, MATK, BIRC5, MYC, GEMIN6, PSIP1, DSCC1, STRBP, SMN1, EXOSC9, TOE1, GEMIN2, TRIP13, ORC2, MSH3, MNAT1, KIT, RFC5, FOXO4, AATF, RBM14, ZNF281, NPPB, RPA3, APOE, PFDN6, COPS3, CCND1, CXADR, MCM2, ANAPC1, SUMO1, SSB, HSP90AB1, TRAIP, PHC1, LRIF1, LSM3, SNRPN, RPP40, MSH2, FBP1, PFN1, OTX2, STX3, STXBP3, GTF2H2, ELAC2, TCERG1, ERCC5, PASK, ZNF593, PSME3, WRN, ARID3B, ERBB3, POP1, KAT7, PTPN6, SYNCRIP, SIRT1, SLC19A1, ARL4A, CEBPZ, MSH6, AURKA, BAK1, MTHFD1, HSPA9, MYBL2, POP5, RFC4, CHEK1, BCCIP, SOCS1, PHB, PMF1, MPP6, NOC2L, HDAC2, CENPE, RECQL4, CASP6, GNL3, SRSF2, BRIX1, MYB, RNMTL1, DHFR, FEN1, SNRPF, MUTYH, PRNP, MT1G, PSMD11, GAR1, DDX11, FUBP1, CDK7, WRAP73, CASP9, RASL11B, CHAF1A, CCNB1, CKS2, CCNA2, PPAN, WEE1, TP53, HMMR, TDP2, RAD9A or RAD54L.

Agent for MHC I Antigen Presentation

Fetal stem cells or organoids as obtained from engineered iPSC or ESC cells are maintain after differentiation, in presence of an agent that will improve the presentation of antigens through the MHC I pathway. Such improved expression can be checked by comparing the number of MHC I molecules at the surface of the cells in the presence or in the absence of the agent.

Such agents are known in the art and one can cite, in particular histone deacetylase inhibitors (HDACis). Numerous products having this activity are known in the art, among these HDACis, one can cite, in particular valproate (VPA or valproic acid, CAS number 99-66-1). Other HDACis that can be used (as they have the same mode of action than VPA) are, in particular, vorinostat, romidepsin chidamide, panobinostat, belinostat, panobinostat, mocetinostat, abexinostat, entinostat, SB939, resminostat, givinostat or quisinostat.

These agents are present in the cell culture medium permissive for fetal stem cells and after pluripotent stem cell differentiation.

Inactivating the Fetal Cells

The fetal stem cells that are used in the present invention are inactivated. As used herein, the term "inactivated", and grammatical variants thereof, refers to a cell (e.g., a fetal cell) that is alive but has been rendered incapable of proliferation (i.e., mitotically inactivated). The skilled in the art may use techniques that are known in the art including, but not limited to exposure to chemical agents, irradiation and/or lyophilization. Fetal stem cells can be inactivated such that upon administration to a subject the fetal cells are incapable of dividing and thus cannot form a fetal tissue in the subject. It is understood that in the context of a plurality of cells, not every cell needs to be incapable of proliferation. Thus, as used herein the phrase "inactivated to an extent sufficient to prevent tissue formation in the subject" refers to a degree of inactivation in the population as a whole such that after administration to a subject, a fetal tissue does not form since the irradiated fetal stem cells did not divide anymore as confirmed by in vitro culture. It is to be noted that, even if a one or more cells in the plurality of cells are in fact capable of proliferation in the subject, it is postulated that the immune system of the host will destroy those cells before a fetal tissue could form. Such inability of proliferation and tissue formation may be confirmed by testing in mice having a functional and a non-functional immune system.

In some embodiments, the "inactivated" cell is a killed cell. In another embodiment, the inactivated cell is a whole cellular lysate, fetal stem cells or oganoid derived exosomes, enriched cancer stem neo-antigens, a whole purified cancer stem neo-antigens, DNA, mRNA and protein extracts, a whole cells suspension that has been lyophilized, a fraction of a cellular lysate such as a membrane fraction, a cytoplasmic fraction, or a combination thereof. Inactivated fetal stem cells remain capable of stimulating immune response when the vaccination of mice is carried out with fetal stem cells in combination with valproic acid or another HDACi. This vaccination is able to induce efficient immune and antitumoral responses against carcinoma without evidence of side effects and autoimmune diseases.

Typically, to inactivate the fetal stem cells, they can be exposed to lethal doses of radiation, (e.g., 5 to 100 Gy single fraction). The precise radiation dose delivered to the fetal cells and length of dose are not critical so long as the cells are rendered nonviable.

Recovering and Conditioning the Cells

The recovery step of the method includes one (or multiple) step(s) of washing the cell culture and resuspending the cells in any appropriate medium such as any clinical grade cell media. The conditioning of the cells may include freezing or lyophilizing the cells, in order to be able to store the cell composition before use.

Mutating the Fetal Stem Cells and Expressing Neo-Antigens

It is reminded that pluripotent cells are cells that are genetically very stable. Indeed, since they are present very early in the process of embryo development and they must multiply for embryo development, it is important that these cells are not too prone to mutations in order to have homogeneity in the embryo.

Consequently cells present in a population of pluripotent cells are generally very homogenous when considering their genetic content (i.e. more than 95% of the cells of the population present the same genetic background.

When preparing iPSCs, a selective advantage of some cells occur during multiple passages, which leads to the population of iPSCs clones that present particular mutations at late passages, but the sequence of the cell genomes are similar close to 100%.

However, after several passages, iPSC are as stable as hESC (Hussein S M and al, Nature 2011). Culture-induced (adaptive) mutations will be acquired with a very few genetic changes upon prolonged culture (Hussein S M and al, Bioessays, 2013).

It is however, favorable to be able to induce mutations in the pluripotent stem cells in order to increase the variability of embryonic neo-antigens on the treated cellular material. Derived fetal stem cells from mutated pluripotent stem cells are used to revealed tissue specific fetal neo-antigens that are found in mostly aggressive cancers. In this way it will increase the possibility for the immune system to generate T cells against fetal neo-antigens presented by these mutated fetal cells, able to fight cancer cells as well as those that would undergo later variation during growth of the tumor.

This would help to fight the cancer that results from accumulation of somatic genetic alterations resulting from DNA replication errors and/or environmental insults during proliferation and progression of cancer stem cells. These alterations include cancer driver mutations that initiate carcinogenesis and genome destabilizing mutations. This increased genome instability results in clonal evolution leading to the selection of more aggressive clones with increased drug resistance.

The cells can thus be exposed to a mutagenic agent, i.e. a physical or chemical agent that changes the genetic material, usually DNA, of an organism and thus increases the frequency of mutations above the natural background level.

The mutagen can be selected from the group consisting of physical mutagens and chemical mutagens.

Among physical mutagens, one can cite
  ionizing radiations such as X-rays, gamma rays and alpha particles which may cause DNA breakage and other damages. One can, in particular cite radiations from cobalt-60 and cesium-137. The level of irradiating rays shall be much lower the one that is used for cells inactivation and can be designed by the person skilled in the art;
  ultraviolet radiations with wavelength above 260 nm, which can cause error in replication if left uncorrected;
  radioactive decay, such as 14C in DNA.

Among chemical mutagens, one can cite
  Reactive oxygen species (ROS), such as superoxide, hydroxyl radicals, hydrogen peroxide;
  Deaminating agents, such as nitrous acid which can cause transition mutations by converting cytosine to uracil;
  Polycyclic aromatic hydrocarbon (PAH), which can bind to DNA when activated to diol-epoxides;
  Alkylating agents such as ethylnitrosourea (ENU, CAS number 759-73-9), mustard gas or vinyl chloride;
  Aromatic amines and amides such as 2-Acetylaminofluorene;
  Alkaloid from plants, such as those from *Vinca* species;
  Bromine and some compounds that contain bromine;
  Sodium azide;
  Bleomycin;
  Psoralen combined with ultraviolet radiation;
  Benzene;
  Base analogs, which can substitute for DNA bases during replication and cause transition mutations;
  Intercalating agents, such as ethidium bromide, proflavine, daunorubicin;
  Metals, such as arsenic, cadmium, chromium, nickel and their compounds which may be mutagenic.

In a particular embodiment, one will obtain a population of pluripotent cells in which the cells have random mutations (generally different from cell to cell, thereby leading to a heterogeneous population), in particular in cancer related neo-antigens.

The inventors have shown that it is possible to design culture conditions that make it possible to induce DNA replication errors in pluripotent stem cells without triggering DNA damage-dependent apoptosis.

This is particularly surprising as, as indicated above, pluripotent cells are naturally very stable for there should be as low number as possible mutations introduced during the early stages of embryogenesis. It results from this that the DNA repair machinery is very efficient in these cells, thereby correcting most defects and/or inducing apoptosis in case it is not possible to correct these defects.

In a particular embodiment, pluripotent stem cells of a starting population are expanded and differentiate into a fetal lineage with permissive media in 2D or 3D Organoid culture system (as known in the art) to induce the fetal specific tissue development. In these conditions, one would generally observe a low amount of exome mutations (5-10 mutations per exome).

The pluripotent stem cells are then cultured in vitro with mutagenesis compounds methods to induce and increase genomic instability within the pluripotent stem cells, such as the ones listed above. DNA damage is well confirmed by phosphorylation of γH2AX as a marker for Double-Strand Breaks (DSBs). Both proportion of γH2AX positive cells and frequency of γH2AX foci increased in ESCs or IPSCs as well as higher number of micronuclei as a mark of genomic instability. Mutated pluripotent stem cells are then amplified and differentiated into fetal lineage in 2D or 3D organoid culture system to induce the fetal specific tissue development. During differentiation, a set of somatic mutations are selectively expressed in the fetal cells. These tissue or lineage specific somatic mutation promote a growth and survival advantage and are specific to the lineage.

In one embodiment, the fetal cells obtained after differentiation can be also cultured in vitro with a mutant compound to induce somatic mutations.

Preferred agents are Bleomycin, ENU, alkylating agents, Actinomycin D, ROS-modulating agents, UV, H2O2, ionizing radiations (gamma rays, X rays), which all allow the induction and enhancement of mutation rates in pluripotent stem cells that accumulate during culture.

In a particular embodiment, N-ethyl-N-nitrosourea (ENU) has been shown to create novel mutations and enhance the level of neo-antigens in treated pluripotent stem cells during long term culture at least from 7 to 60 days at a dose of <50 µg/ml. These somatic mutations selectively expressed in fetal stem cells are similar to those reported in cancer. It is thus possible to accumulate a diversity of mutations in response to DNA damage in pluripotent stem cells with a high rate of mutations from a selective advantage upon prolonged culture, while maintaining the pluripotency of the cells, in particular when the cells are cultured with HDACi in the medium. The presence of HDAC is in culture preserves the increase active histones (H3K4me3 and H3K9ac). After differentiation, fetal cells derived from mutated pluripotent stem cells are maintained in permissive culture media and HDACi. The cells expressing a higher level of neo-antigens are compared to fetal cells derived from non-mutated pluripotent stem cells.

In another embodiment, the compositions and methods described herein, mutations are induced in the pluripotent stem cells through genetic modification of the cells with genes that promote high level of genomic instability. In particular, one can delete or reduce activity of genes or signaling pathways involved in DNA repair and replication, using appropriate inhibitors such as NER/BER/DSBR/MMR inhibitors. These methods that induce genomic instability linked to increased DNA damage may be performed by using "vectors" or by "genetic modification" that inactivate or knock down DNA repair related genes or signaling pathways such as DNA polymerase delta complex, mismatch repair (MMR), base excision repair (BER), Nucleotide excision repair (NER), homologous recombination (HR), DSBR or NEJH. Other examples of DNA repair genes are DNApkC, Ku70, Rad 51, Brca1 or Brca2.

In other embodiments, pluripotent stem cells are modified so as to repress apoptosis-associated genes such as p53 by genetic modification or chemical p53 such as Pifithrin-mu, Nutlin-3, or by using compounds that enhance cell survival such as Y-27632, a selective inhibitor of the p160-Rho-associated coiled kinase (ROCK).

In a particular embodiment, the population of pluripotent stem cells were generated from somatic cells, such as cells isolated from a patient that already contained genomic alterations linked
  i) to DNA repair diseases including for example Ataxia telangiectasia, Bloom syndrome, Cockayne's syndrome, Fanconi's anaemia, Werner syndrome, Xeroderma pigmentosum, Nijmegen breakage syndrome;
  ii) to hereditary family cancer syndromes with genomic instability, such Lynch syndrome (hereditary non-polyposis colorectal cancer with mutations in MMR genes including MLH1, MSH2, MSH6, PMS1, and PMS2), Li-Fraumeni with mutation in the TP53 gene or CHEK2, Hereditary Breast and Ovarian Cancer (HBOC) syndrome with deletion or mutation in BRCA1/2 gene, familial adenomatous polyposis (FAP) with mutations in APC gene; renal cell carcinoma with c-Met mutation; medullary thyroid cancer with RET mutations;
  iii) somatic oncogenic induced genomic instability as in CML with a translocation (T 9;22), Jak mutation.

In a particular embodiment, the pluripotent stem cells are derived from somatic cells containing genomic alterations linked to a disease. Typically, genomic alterations could be a translocation (t9:22), a deletion (BRCA1/2) or mutations (BRCA, RET, c-Met). Fetal stem cells derived from these pluripotent stem cells reproduce the genomic alteration at fetal level.

In a particular embodiment, the population of pluripotent stem cells (iPSCs) is generated from cancer cell lines or patient-specific cancer cells. Derived fetal stem cells or organoids reproduce the cancer phenotype and genotype at the fetal level, similar to those reported in primary cancer. In another embodiment, the pluripotent stem cells are genetically modified to over-express multiple non-random cancer stem related neo-antigens by using «vectors». In particular embodiment, the population of pluripotent stem cells, fetal stem cells or organoids are modified genetically to express multiple mutations and cancer stem cell specific neo-antigens (at least 1) by "genome editing" technology. The genetically modified fetal stem cells or organoids reproduce the cancer genotype similar to those reported in primary cancer. The present invention provides compositions and methods providing pluripotent stem cells and fetal cells or organoids by introducing of multiple neo-antigens thereof by RNA-guided multiplex genome editing, modification, inhibition of expression and other RNA-based technologies.

The term "genome editing" used here refers to the RNA mediated genetic manipulation including, in particular, a guide RNA for cas9-mediated genome editing. This guide RNA, (gRNA) is transfected along with an endonuclease cas9. The guide RNA provides the scaffold and a spacer sequence complementary to the target. In another embodiment genetic manipulation sequence can be a siRNA or a microRNA sequence designed for gene silencing according to standard methods in the art by the use of Crispr-Cas 9 systems. Compositions and methods for making and using Crispr-Cas systems are known in the art and described, in particular, in U.S. Pat. No. 8,697,359.

In a particular embodiment, the population of pluripotent stem cells or the derived fetal cells are treated with alkylating agents. As used herein, the term "alkylating agents" refers to a substance which adds one or more alkyl groups from one molecule to another. This treatment creates new mutations in neo-antigens providing superior immune reactions by increasing oligo clonal expansion of TILs and Th1/Th2 cellular immunity. In the present invention, an alkylating agent is selected from the group consisting of nitrogen mustards, nitrosoureas, alkyl sulfonates, triazines, ethylenimines, and combinations thereof. Non-limiting examples of nitrogen mustards include mechlorethamine (Lundbeck), chlorambucil (GlaxoSmithKline), cyclophosphamide (Mead Johnson Co.), bendamustine (Astellas), ifosfamide (Baxter International), melphalan (Ligand), melphalan flufenamide (Oncopeptides), and pharmaceutically acceptable salts thereof. Non-limiting examples of nitrosoureas include streptozocin (Teva), carmustine (Eisai), lomustine (Sanofi), and pharmaceutically acceptable salts thereof. Non-limiting examples of alkyl sulfonates include busulfan (Jazz Pharmaceuticals) and pharmaceutically acceptable salts thereof. Non-limiting examples of triazines include dacarbazine (Bayer), temozolomide (Cancer Research Technology), and pharmaceutically acceptable salts thereof. Non-limiting examples of ethylenimines include thiotepa (Bedford Laboratories), altretamine (MGI Pharma), and pharmaceutically acceptable salts thereof. Other alkylating agents include ProLindac (Access), Ac-225 BC-8 (Actinium Pharmaceuticals), ALF-2111 (Alfact Innovation), trofosfamide (Baxter International), MDX-1203 (Bristol-Myers Squibb), thioureidobutyronitrile (Cell-Ceutix), mitobronitol (Chinoin), mitolactol (Chinoin), nimustine (Daiichi Sankyo), glufosfamide (Eleison Pharmaceuticals), HuMax-TAC and PBD ADC combinations (Genmab), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1G cells and ifosfamide combinations (Nuvilex), estramustine phosphate (Pfizer), prednimustine (Pfizer), lurbinectedin (PharmaMar), trabectedin (PharmaMar), altreatamine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), and pharmaceutically acceptable salts thereof. In another embodiment, the alkylating agent is selected from the group consisting of mechlorethamine (Lundbeck), chlorambucil (GlaxoSmithKline), cyclophosphamide (Mead Johnson Co.), streptozocin (Teva), dacarbazine (Bayer), thiotepa (Bedford Laboratories), altretamine (MGI Pharma), pharmaceutically acceptable salts thereof, and combinations thereof. In another embodiment, the alkylating agent is selected from the group consisting of ProLindac (Access), Ac-225 BC-8 (Actinium Pharmaceuticals), ALF-2111 (Alfact Innovation), bendamustine (Astellas), ifosfamide (Baxter International), trofosfamide (Baxter International), MDX-1203 (Bristol-Myers Squibb), temozolomide (Cancer Research Technology), thioureidobutyronitrile (CellCeutix), mitobronitol (Chinoin), mitolactol (Chinoin), nimustine (Daiichi Sankyo), carmustine (Eisai), glufosfamide (Eleison Pharmaceuticals), HuMax-TAC and PBD ADC combinations (Genmab), busulfan (Jazz Pharmaceuticals), melphalan (Ligand), BP-C1 (Meabco), treosulfan (Medac), nifurtimox (Metronomx), improsulfan tosilate (Mitsubishi tanabe Pharma), ranimustine (Mitsubishi tanabe Pharma), ND-01 (NanoCarrier), HH-1 (Nordic Nanovector), 22P1 G cells and ifosfamide combinations (Nuvilex), melphalan flufenamide (Oncopeptides), estramustine phosphate (Pfizer), prednimustine (Pfizer), lurbinectedin (PharmaMar), trabectedin (PharmaMar), altreatamine (Sanofi), lomustine (Sanofi), SGN-CD33A (Seattle Genetics), fotemustine (Servier), nedaplatin (Shionogi), heptaplatin (Sk Holdings), apaziquone (Spectrum Pharmaceuticals), SG-2000 (Spirogen), TLK-58747 (Telik), laromustine (Vion Pharmaceuticals), procarbazine (Alkem Laboratories Ltd.), pharmaceutically acceptable salts thereof, and combinations thereof.

In a particular embodiment, the population pluripotent stem cells is treated with N-ethyl-N-nitrosourea (ENU, CAS Number 759-73-9). ENU has the following chemical formula $C_3H_7N_3O_2$, is a highly potent mutagen by transferring the ethyl group to nucleobases in nucleic acids.

As indicated above, the purpose of the mutagenic agent is to introduce random mutations in genes of the pluripotent stem cells during expansion (introduction of mutations occurs during the replication and division of the cells). The population of pluripotent stem cells acquires mutations that may provide a growth advantage and are selected for to promote culture adaptation. The population of fetal cells derived from pluripotent stem cells acquires mutations promoting growth and survival of fetal cells in the permissive culture media.

In a particular embodiment, when ENU is used, it may be applied for at least 7 days, more preferably at least 15 days, more preferably at least 20 days, more preferably at least 30 days, more preferably at least 40 days, more preferably at least 50 days or even at least 60 days.

After application of the mutagen, the cells are washed (if the mutagen is a chemical agent) and can be further incubated, in the presence of the agent that favors MHC-I expression, in particular a HDACi. This agent is preferably also present during application of the mutagenic agent.

It can thus be observed and checked that the mutagen will induce mutations (i.e non-synonymous, nonsense, frameshift, StopGain, splice variant, CNVs, SNVs) in some fetal genes expressed in fetal cells and hence, increase the diversity of fetal antigens (new neo-antigens within the whole genome). This will thus increase the possibility of the vaccine composition with enhanced immunogenicity, able to stimulate a broad immune response against aggressive cancers where there are rapid and frequent mutations.

An efficient immune response may indeed be difficult to obtain for some cancer where a clonal evolution occurs with novel somatic mutations in the antigens expressed by the tumor cells during progression. The immune response would thus depend in the mutational load of the cancer and immunogenic neo-antigens. The generation of specific mutations in the fetal cell population by the use of the mutagen would thus lead to increase the diversity of the antigens presented to the immune system upon vaccination.

Consequently, there would already be primed T-cells against mutated fetal antigens that would appear in the cancer cells during division of such cells, which would speed-up and improve the immune response against these cells.

In a particular embodiment, the pluripotent stem cells can be firstly differentiated by the classical methods (e.g. in defining culture conditions using small molecules, morphogenic and growth factors in 2D or 3D culture system) and then there are treated with a mutagen (e.g. ENU) to express fetal neo-antigens.

Modification of Fetal Stem Cells

In a particular embodiment, the population of pluripotent stem cells is modified genetically to over-express compounds which stimulate immune response by using gene integration within the pluripotent cell genome. Typically, in the first step, the population of pluripotent stem cells is isolated and expanded. In the second step, the genes of interest are packaged into integrative viral vectors, such as retroviruses or lentiviruses. In the third step, integrative viral vectors containing the interest gene are transferred to the population of pluripotent stem cells and are differentiated into fetal stem cells.

In a particular embodiment, the population of fetal stem cells or organoids is modified with the genes of proteins which stimulate MHC expressions and/or immune response. These compounds are selected from the group consisting of interferon alpha (IFN-α), an interferon gamma (IFN-γ), an interleukin 2 (IL-2), an interleukin 4 (IL-4), an interleukin 6 (IL-6), an interleukin 12 (IL-12), a tumor necrosis factors (TNFs), and a granulocyte-macrophage colony stimulating factor (GM-CSF), functional fragments thereof, and combinations thereof.

Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognize and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention.

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Amesp (erytropoietin).

In its broadest sense, a "vector" is any vehicle capable of facilitating the transfer of the oligonucleotides to the cells. Preferably, the vector transports the nucleic acid to cells with reduced degradation relative to the extent of degradation that would result in the absence of the vector. In general, the vectors useful in the invention include, but are not limited to, naked plasmids, non-viral delivery systems (electroporation, sonoporation, cationic transfection agents, liposomes, etc. . . . ), phagemids, viruses, other vehicles derived from viral or bacterial sources that have been manipulated by the insertion or incorporation of the nucleic acid sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Typically, in the context of the invention, viral vectors include adenoviruses and adeno-associated (AAV) viruses, which are DNA viruses that have already been approved for human use in gene therapy. Actually 12 different AAV serotypes (AAV1 to 12) are known, each with different tissue tropisms (Wu, Z Mol Ther 2006; 14:316-27). Recombinant AAV are derived from the dependent parvovirus AAV (Choi, VW J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hematopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected through an intraocular way (intravitreal, sub retinal, suprachoroidal . . . ). It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a particular embodiment, the population of fetal stem cells is modified by the introduction of the transgene such as siRNA into the AAVS1 locus of chromosome 19 by homologous recombination.

The term "homologous recombination" as used herein refers to a gene targeting means for artificially modifying a specific gene on a chromosome or a genome. When a genomic fragment having a portion homologous to that of a target sequence on the chromosome is introduced into cells, the term refers to recombination that takes place based on the nucleotide sequence homology between the introduced genomic fragment and the locus corresponding thereto on the chromosome.

Also, the term "genetic modification" refers to, in the locus of a desired gene on the chromosome, the insertion of an exogenous DNA, the substitution of a portion of or the whole of the gene with an exogenous DNA, or the deletion of the gene. More specifically, genetic modification refers to the insertion (that is, "knock-in") of an exogenous DNA fragment while the endogenous DNA sequence is retained in a manner such that the fragment is expressed in conjunction with the expression of a gene at a specific locus or is expressed constitutively, or, the substitution, deletion, or disruption (that is, "knock-out") of a portion of or the whole gene sequence so as to modify the endogenous DNA sequence.

Examples of methods for introducing an artificial chromosome into cells include a calcium phosphate precipitation method (Graham et al., (1973) Virology 52: 456-467, Wigler et al., (1979) Proc. Natl. Acad. Sci. U.S.A. 76 1373-1376 and Current Protocols in Molecular Biology Vol. 1, Wiley Inter-Science, Supplement 14, Unit 9.1.1-9.1.9 (1990)), a fusion method using polyethylene glycol (U.S. Pat. No. 4,684,611), a method using lipid carriers such as lipofection (Teifel et al., (1995) Biotechniques 19: 79-80, Albrecht et al., (1996) Ann. Hematol. 72: 73-79; Holmen et al., (1995) In Vitro Cell Dev. Biol. Anim. 31: 347-351, Remy et al., (1994) Bioconjug. Chem. 5: 647-654, Le Bolc'h et al., (1995) Tetrahedron Lett. 36: 6681-6684, Loeffler et al., (1993) Meth. Enzymol. 217: 599-618 and Strauss (1996) Meth. Mol. Biol. 54: 307-327), electroporation, and methods for fusion with microcells (U.S. Pat. Nos. 5,240,840, 4,806, 476, 5,298,429, and 5,396,767, Fournier (1981) Proc. Natl. Acad. Sci. U.S.A. 78: 6349-6353 and Lambert et al., (1991) Proc. Natl. Acad. Sci. U.S.A. 88: 5907-59).

Population of Fetal Stem Cells

Thus, with the methods as described above, the inventors have obtained a population of fetal stem cells expressing new fetal epitopes within partial or all the fetal genes that will trigger a more efficient antitumor immunity. Accordingly, in a fourth aspect, the invention relates to a population of stem cells obtained according the method as described above. The population of fetal stem cells derived from pluripotent stem cell pre-treated with N-ethyl-N-nitrosourea (ENU) presents an increased number of novel mutations compared to the population of fetal cells derived from non-mutated pluripotent stem (i.e without the pre-treatment by ENU). Theses fetal neo-antigens are associated to primary cancer. Accordingly, this population is also a subject of the invention.

The population as obtained is thus characterized in particular in that the fetal stem cells have lost the genes related to pluripotency with at least 20% the following genes NACC1, BLM, WDR33, DAZAP1, CDK1, CDC45, ZNF165, XRCC5, SMARCAD1, AIMP2, CKS1B, NANOG, ZFP42, U2AF1, CCNB2, DCTPP1, TGIF1, SUPT3H, AURKB, GEMIN7, SRSF1, PNP, SIGLEC12, POU5F1, PSMA3, RMND5B, GDF9, STXBP2, BAG6, GMPS, PCNA, NME1, POP7, RCHY1, SMARCC1, HNRNPK, PTMA, NPM1, SNRPA, MYBBP1A, CDT1, HSPD1, TRIM28, PHF10, GRB7, HSPE1, DAXX, FAM136A, KPNA2, FUS, PNN, RFC3, HPRT1, PA2G4, SNRPE, RBPMS, PRMT5, PIAS2, BYSL, POLD2, LSM5, TDGF1, NOP56, EPPK1, TARBP2, MRE11A, CDC7, SRSF3, TNNI3, NUDT1, DIAPHI, PPID, CDA, GADD45A, MCM6, SNURF, CDC25C, TNFRSF8, STIP1, ACTA1, POLR1D, TUBA3C, RPA1, VAMP8, UNC119, COIL, BIK, PARP1, SP1, CHEK2, NLE1, RPA2, HDAC1, KPNB1, LSM7, TMSB4Y, HMGA1, POLR1C, LSM1, EXO1, MCM5, ITGB3BP, LSM6, UNG, PSMA6, CCNE1, SMNDC1, SET, FKBP3, TK1, CTBP2, POLQ, PLSCR1, GMNN, RND1, NUP153, PHGDH, SNRPB, HSPA14, HSPH1, TCOF1, ANP32A, PELP1, MBD2, HIST1H2BC, TMPO, SPAG5, DNMT3B, LCK, ARMC6, COPS6, MCM3, PPAP2C, LSM4, NME1-NME2, EWSR1, POLG2, BCL2, NFKBIB, SALL4, PXN, EXOSC8, HSPA2, HMGB1, RUVBL1, GOT2, PPM1B, ATIC, DHCR24, APEX1, RFC2, WDYHV1, NTHL1, EXOSC7, SNRPD1, DPPA2, MRPS12, FBL, POLD1, MCM10, EXOSC3, NOP58, TPX2, PAK3, HNRNPAB, ANXA2, BUB1B, SEPHS1, WDR77, LUC7L3, VASP, MCM4, PAKI, PMAIP1, PBX1, NOLC1, PCYT1B, NCL, ORC6, GPRIN2, ORC1, RAD51, HSPA8, ANXA3, NUP50, SNRPC, HAUS1, MATK, BIRC5, MYC, GEMIN6, PSIP1, DSCC1, STRBP, SMN1, EXOSC9, TOE1, GEMIN2, TRIP13, ORC2, MSH3, MNAT1, KIT, RFC5, FOXO4, AATF, RBM14, ZNF281, NPPB, RPA3, APOE, PFDN6, COPS3, CCND1, CXADR, MCM2, ANAPC1, SUMO1, SSB, HSP90AB1, TRAIP, PHC1, LRIF1, LSM3, SNRPN, RPP40, MSH2, FBP1, PFN1, OTX2, STX3, STXBP3, GTF2H2, ELAC2, TCERG1, ERCC5, PASK, ZNF593, PSME3, WRN, ARID3B, ERBB3, POP1, KAT7, PTPN6, SYNCRIP, SIRT1, SLC19A1, ARL4A, CEBPZ, MSH6, AURKA, BAK1, MTHFD1, HSPA9, MYBL2, POP5, RFC4, CHEK1, BCCIP, SOCS1, PHB, PMF1, MPP6, NOC2L, HDAC2, CENPE, RECQL4, CASP6, GNL3, SRSF2, BRIX1, MYB, RNMTL1, DHFR, FEN1, SNRPF, MUTYH, PRNP, MT1G, PSMD11, GAR1, DDX11, FUBP1, CDK7, WRAP73, CASP9, RASL11B, CHAF1A, CCNB1, CKS2, CCNA2, PPAN, WEE1, TP53, HMMR, TDP2, RAD9A or RAD54L.

The absence of expression of lineage specific genes of adult differentiated cells.

The invention thus relates to a composition of cells comprising fetal stem cells, wherein cells in said population present fetal neo-antigens. The somatic mutation rate of fetal neo-antigens is qualified in the fetal stem cell population derived from a master bank of pluripotent stem cell after exposure to the mutagenic agent. The stability of these somatic fetal neo-antigens is qualified before or after further expansion, if such further expansion is performed. Mutation rate in fetal stem cells or organoids is of at least 0.1%, preferably at least 1%, more preferably at least 2%, more preferably at least 5%, more preferably at least 10%, more preferably at least 15%, more preferably at least 20%, more preferably at least 30%, more preferably at least 40%, or even at least 50%, in at least one gene selected from fetal neo-antigens expressed in derived fetal cell cells or organoids. The mutation rate for a given gene is obviously calculated by sequencing the DNA for the gene, and calculating the percentage of copies that contain a mutation with regards to the native sequence (which is the sequence that is essentially and mainly present (as the predominant sequence is the native "wild-type" sequence).

Human derived fetal hematopoietic stem cells (i.e from derived human hematopoietic embryonic body after ex-vivo treatment by mutagen agents) expressed fetal neo-antigens. These fetal neoantigens are characterized in the following group with at least: ARHGEF10L:221656_s_at, TRIM66:213748_at, ARHGEF10L:1570511_at, NKAIN3:1553241_at, ITGA7:216331 at, GGT1:211417_x_at, PDZD7:220555 s_at, MUC4:235055_x_at, GGT1:215603_x_at, MUC2:204673_at, NECAB3:210720_s_at, GGT1:208284_x_at, MNT:204206_at, GGT1:207131_x_at, ITGA7:209663_s_at, BTNL9:230992_at, FNBP1:230086_at, GLTSCR1:219445_at, NECAB3:223954_x_at, COPZ2:219561_at, ZFP36:201531_at, MIB2:241541_at, ABCC12:1553410_a_at, IGFN1:1563098_at, LRRK2:229584_at, MNT:236749_at, RIN3:220439_at, GGT1:233837_at, KIF5C:1557089_at, ANK2:202921_s_at, HDAC7:236326_at, MUC20:1558220_at, SDCCAG3:230058_at, GGT1:209919_x_at, RIN3:1562005_at, DNAI1:233195_at, DNAI1:220125_at, BTNL9:241496_at, ABTB2:232624_at, MC2R:208568_at, DOCK4:244840_x_at, FSD1L:230904_at, HDAC7:217937_s_at, CRP:205753_at, PPP1R3A:206895_at, SLC22A17:221106_at, PITPNM1:203826_s_at, BTBD7:224943_at, MIB2:241377_s_at, A2M:1558450_at, CTDSP2:208735_s_at, IFNA14:208182_x_at, KIF5C:203130_s_at, MUC20:243774 at, THNSL2:239949 at, KIF5C:203129_s_at, GTF3C3:1555439_at, NRXN1:1558708_at, MED26:1559593_a_at, FNBP1:230389_at, TMCO3:230317_x_at, PPP1R3A:211169_s_at, ING1:208415_x_at, ZNF292:1562991_at, RBL1:1555004_a_at, CD109:239719_at, CD109:229900_at, FOXRED2:233250_x_at, PLIN2:209122 at, ZNF85:1554445 at, SESN1:218346_s_at, TMCO3:220240_s_at, MED26:231724_at, CD109:226545_at, CENPE:205046_at, ING1:210350_x_at, TMCO3:226050_at, FOXRED2:220707_s_at, GTF3C3:222604_at, BTBD7:224945_at, CDC27:217881_s_at, STOM:201061_s_at, CDC27:217880_at, ZNF317:

1555337_a_at, TET1:228906 at, LRBA:214109 at, MED4: 217843_s_at, CDC27:217879_at, ZNF317:225296_at, ZNF292:212366_at, MED4:222438_at, BCR:226602_s_at, STOM:201060_x_at, BCR:202315_s_at, ZNF85: 206572_x_at, BCR:217223_s_at, HPRT1:202854_at, LRBA:212692_s_at, GTF3C3:218343_s_at, NASP:201969 at, NASP:201970_s_at, MSH2:209421_at.

In a particular embodiment, the human fetal renal organoid derived from pluripotent stem cells express fetal antigens in renal progenitors that are commonly associated to cancer genes reported in primary adult renal carcinoma. These characterized fetal genes correspond to the following group with at least: TRAPPC4, MX1, ITSN1, DNAJC7, TAF15, TMEM88, CRYM, PRTG, TYRO3 C12ORF60, FJX1, ADM, FAM45A, ASS1, CA2, ZFHX4, CLVS1, NRG1, EZH2, SLC22A23, MSH5, FBN2, GTF2H2, LIX1, HESX1, FZD5, LRP2, RHOQ, NUAK2, ILF2, ACP6, RPL5, NMNAT1, ID1, U2AF2, KLHL14, CDH2, GREB1L, ARRDC4, THBS1, BMP4, LRIG3, SOX5, SF1, LGR4, MGEA5, BCORL1, STOM, GLIS3, ANXA1, KDM4C, SDC2, TMEM130, MAGI2, GLI3, HEY2, TPBG, ID4, MYLIP, ENC1, EGR1, CDH6, NPY1R, SEL1L3, LRAT, CLDN1, CEP97, BHLHE40, ARL5A, ARL4C, ZNF385B, LYPD1, B3GNT7, INSIG2, ARHGAP29, NOTCH2, IFI16.

Exposure of the pluripotent cells to the mutagenic agent will trigger apparition of random mutations in the genome of such cells. The population resulting from such exposure will thus be heterogeneous, as compared to a population of fetal stem cells that is essentially more homogenous and restricted to cancer neo-antigens reported in primary cancer genome.

In a further embodiment, the invention relates to a composition of cells comprising fetal stem cells, wherein cells in said population present a mutational landscape in the population of fetal stem cells comprising one or more of the following features:
1) At least one (or more as seen above) cancer related neo-antigens mutations introduced genetically in fetal stem cells by genomic modification.
2) A combination of mutation types restricted to cancer genome induced by mutagen agents and enriched by a selective advantage in cultured fetal stem cells.

Mutagen process is causing increased levels of novel genomic mutations and genetic mosaicism in the fetal stem cell lines. Analysis of the mutations in the genes is preferably performed by large scale genomic analysis of induced cancer related "mutanome" signature, in fetal stem cells population, by NGS, Exome, RNAseq or Whole-genome sequencing, CGH array, SNP arrays. Whole-exome sequencing in combination with transcriptome profiling enables the description of the expressed protein coding mutanome.

Genomic somatic aberrations and neo-antigens are identified by using at least 2 algorithms for bioinformatics analysis, known in the art. The prevalence of total mutations in the whole genome after application of the mutagen agents will confirm the higher mutation and/or CNV load in output fetal stem cells.

Qualitative and quantitative criteria will allow defining each cell population within genetic mosaicism in fetal stem cells as described:
Qualitative criteria include:
Identification of acquired novel molecular somatic alterations (mutations, CNVs or SNVs) defined regarding their presence in fetal stem cells genome after mutagenesis and their absence in the parental pluripotent stem cells with and without mutagenesis;
Classification of each novel mutations (i.e non-synonymous, nonsense, splice variant, CNVs, SNVs) and validation by their overlapping detection between the primary patient specific cancer or the cancer genome (from data base i.e. TCGA, ICGC, COSMIC) and the fetal stem cells genes, that are absent in normal adult cells or tissue.

Quantitative criteria such include:
The prevalence of these novel somatic mutations (with false discovery rate confidence value FDR≤0.05) and novel CNVs/SNVs (with FDR<10%) in the whole genome is defined for each fetal stem cell population or organoids;
The presence of validated mutation in at least >3 different fetal genes;
The mutation rate of each novel and stable somatic mutations with an allelic frequency from at least from >0.1%, or other percentages as seen above, up to 50% after clonal selection and expansion or regarding the number of passages (from 50× depth to 100× depth and 80-98% of target exome coverage);
The expression of stable fetal stem cells markers and a gene-expression based assay with at least >90% of expression rate compared to input fetal stem cells before mutagenesis or genetic modification;
Expression of MHC I molecules at the cell surfaces (for instance as determined by FACS) being increased of at least 50%, and generally up to 90% as compared to the fetal cell population maintain in the absence of HDACi, in particular VPA.

Vaccine Composition

The population of fetal stem cells as described above can be used in a vaccine composition. Accordingly, in a fifth aspect, the present invention relates to a vaccine composition comprising a population of fetal stem cells, as disclosed above and an agent that stimulates immune response and/or MHC I expression.

In particular, such fetal stem cells are inactivated, and optionally mutated in order to suppress their proliferation ability and optionally obtain cell extracts.

The agent that stimulates immune response may be an adjuvant (immunostimulant) as known in the art. It is preferably a HDACi (used at a dose range comprised between 0.2 mM and 4 mM). When such HDACi is used, another adjuvant may also be used.

The invention also relates to a device (such as a syringe) containing such vaccine composition, that can be used for a simultaneous administration of the HDACi compound and the cell composition.

Such vaccine composition can be used as a therapeutic vaccine against cancer cells (cancer cells of which express immunogenic neo-antigens, driver or passenger mutations, progenitors as epigenetically de-differentiated cells, tumor initiating cells expressing fetal and embryonic genes), for cure of the subject, or as a prophylactic vaccine, to prevent onset of such cancers, in particular in subjects susceptible to these cancers.

Predisposition genes are, for instance (see also Lindor et al, 2008 Journal of the National Cancer Institute Monographs, No. 38, Concise Handbook of Familial Cancer Susceptibility Syndromes, Second Edition):
Breast/ovary: BRCA1, BRCA2, PALB2, RAD51
Lynch syndrome: MLH1, MSH2, MSH6, PMS2, EPCAM
Hereditary Papillary Renal Cell Carcinoma: FH, MET
Cowden disease: PTEN, PIK3CA
Fanconi disease: FANC
Von Hippel-Lindau disease: VHL Malignant melanoma: CDKN2A, MITF, BAP1, CDK4
Endocrine Neoplasia: MEN1, RET, CDKN1B
Neurofibromatosis: NF1, NF2, LZTR1, SMARCB1, SPREDI
Hereditary pheochromocytome paragangliome: SDH, TMEM127, MAX, EPAS1
Familial adenomatous polyposis: APC, MUTYH
Retinoblastoma: RB1
Birt-hogg-dubé syndrome: FLCN
Bloom syndrome: BLM
Carney syndrome: PRKAR1A
Gorlin syndrome: PTCH1
Li-Fraumeni syndrome: TP53, CHEK2
Nijmegen syndrome: NBN
Peutz-Jeghers Syndrome: STKI11
Familial Juvenile Polyposis: BMPR1A, SMAD4
Xeroderma pigmentosum: XP
This list is not limitative.

In certain embodiments, the cancer stem cell vaccine product comprises a mixture of cell lysate after lyophilisation, a mixture of enriched multi-cancer stem neoantigens, purified cancer stem neo-antigens, exosomes derived from fetal stem cells, DNA, RNA, proteins or multiple peptides from engineered fetal stem cells and organoids. These are the immunogenic agent as disclosed above, which are formulated in the presence of HDACi.

In another embodiment, cancer stem cell vaccine product is mixed with supernatant GMP media from engineered irradiated fetal stem cells used as an adjuvant effector.

In a particular embodiment, the derived fetal cells in this composition are inactivated (i.e. cannot proliferate anymore).

The composition of derived fetal stem cells and organoids of the invention is susceptible to be obtained by any of the methods as disclosed above.

It is to be noted that the derived fetal cells in this composition are genetically heterogeneous, carrying specific somatic mutations when the mutagen has been used, and hence, differ from a derived fetal cell composition that has been produced according to methods known in the art, and which is genetically more homogenous.

When it has been cultured in the absence of a mutagen, the population of derived fetal cell differs from a population of derived fetal cells produced with the methods known in the art, as the presence of the agent maintaining expression of fetal genes and increasing MHC I presentation, in the culture medium, will lead to cells that have more of these MHC I molecules on their surface.

As used herein the term "compound selected from a group which activates MHC I expression and/or immune response" refers to compounds which are capable of stimulating immunogenicity. Such compound is called activator of MHC expression and/or immune response. The term "MHC" refers to major histocompatibility complex which is present on the cell surface to recognize foreign molecules, called antigens. MHC binds to antigens and present them to immune molecules such as lymphocytes T and B. The term "immune response" refers to immunological response of immune system to an antigen. By activating the immune response, the population of FoxP3 subpopulation and myeloid-derived suppressor cell (MDSC) are decreased and, in contrary the NK population is increased. In the context of the invention, the immune response against tumors comprises a cytotoxic T cell response against an antigen present in or on a cell of the tumor. In some embodiments, the cytotoxic T cell response is mediated by CD8+ T cells. Typically, in the context of the invention, the antigen which activates the MHC expression and/or immune response corresponds to the molecules present on the population of fetal cells as described above. The compound which activates the MCH expression and/or immune system is a fetal gene or an immunogenic neo-antigen. The term "neo-antigen" or "neo-antigenic" means a class of antigens that arises from at least one mutation which alters the amino acid sequence of genome encoded proteins.

In the context of the invention, compounds are selected from the group consisting of: cytokines, histone deacetylase inhibitors, DNA methyltransferase inhibitors, and histone-lysine N-methyltransferase enzyme inhibitors.

In a particular embodiment, the activator of MHC expression and/or of immune response is a histone deacetylase inhibitor.

As used herein, the term histone "histone deacetylase inhibitor" called also HDACi, refers to a class of compounds that interfere with the function of histone deacetylase. Histone deacetylases (HDACs) play important roles in transcriptional regulation and pathogenesis of cancer. Typically, inhibitors of HDACs modulate transcription and induce cell growth arrest, differentiation and apoptosis. HDACis also enhance the cytotoxic effects of therapeutic agents used in cancer treatment, including radiation and chemotherapeutic drugs.

In a particular embodiment, the histone deacetylase inhibitor is valproic acid (VPA).

The term "valproic acid" refers to acid-2-propylpentanoic ($C_8H_{16}O_2$), which has the following CAS number and formula 99-66-1 in the art:

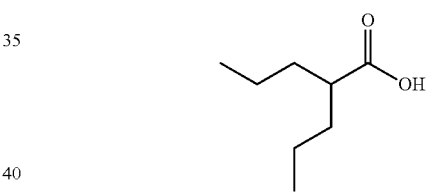

The biological activities of valproic acid are multiple (Chateauvieux et al, J. Biomed. Biotechnol, 2010, pii: 479364. doi: 10.1155/2010/479364). Valproic acid affects the neurotransmitter GABA (Gamma Amino Butyrate) potentiating inhibitory activity. Several mechanisms of action are suggested. Valproic acid is particularly the GABA metabolism: inhibits degradation of GABA, GABA Transaminobutyratre (LAMP), acroissement of GABA synthesis, and modifies its turnover. In addition, valproic acid blocks certain ion channels, reduces arousal mediated by the N-Methyl-D-Aspartate, and blocks the activity of ion channels including Na+ and Ca 2+ (voltage-dependent L-type CACNA1 type C, D, N, and F).

In the context of the invention, valproic acid is used as an immune-stimulant to boost immune response against cancers expressing cancer fetal stem cell neo-antigens shared with fetal stem cells.

More particularly, VPA is used to stimulate and enhance the expression of MHC-I on cancer stem cell compartment, increasing the neo-antigen content in some tumor cells. Higher expression of MHC I on fetal stem cells allow to enhance the presentation of neo-antigens associated with MHC-I to APC/Dendritic cells to induce TH1 immune response. Higher level of chemokines (CXCL9, CXCL10) allows to enhance the recruitment of T cell into the tumor.

The present invention relates to methods to increase the neo-antigen content in derived fetal stem cells in the presence of an HADCi such as VPA and/or 5 Azacytidine and in the tumor cells with expression of fetal antigens through chromatin remodelling, as well as chemokines expression (CXCL9, CXCL1).

In particular, when used for treating a subject in vivo, the present compositions and vaccines makes it possible to modify the tumor microenvironment and promote the recruitment of T cells into the tumor, so as to obtain a long term durable reduction of tumor volume.

This is due to a synergistic effect of the fetal stem cell vaccine and VPA co-administration, that is further improved when the HDACi is further administered to the patient, for a period of time (such as at least 15 days) after vaccine injection.

The examples show that combined treatment by both fetal stem cell vaccine and VPA provide a superior anti-tumor response by increasing TILs with Th1/Th2 cellular immunity, decreasing FoxP3 TReg subpopulation, while reversing the tumor immune suppression and decrease the TReg (in tumor and spleen) and recruiting T CD4+ and CD8+ lymphocytes into the tumor with a less proportion of T CD4 and CD8 expressing PD-1 in the spleen.

VPA may down regulate c-Myc expression level and potentially induce apoptosis and autophagy of cancer cells and tumor initiating cells. VPA may boost the adaptive immune response via autophagosome cross-presentation.

A well other known action of VPA is the decrease of inflammation cytokines such as IL6, IL8, TNFa interleukin (IL)-1beta, IL-17 in the lymph nodes.

In a particular embodiment, the histone deacetylase inhibitor is suberoylanilide hydroxamic acid, also called Vorinostat (N-Hydroxy-N'-phenyloctanediamide) was the first histone deacetylase inhibitor approved by the U.S. Food and Drug Administration (FDA) on 2006 (Marchion D C et al 2004; Valente et al 2014).

In a particular embodiment, the histone deacetylase inhibitor is Panobinostat (LBH-589) has received the FDA approval on 2015 and has the structure as described in Valente et al 2014.

In a particular embodiment, the histone deacetylase inhibitor is Givinostat (ITF2357) has been granted as an orphan drug in the European Union (Leoni et al 2005; Valente et al 2014).

In a particular embodiment, the histone deacetylase inhibitor is Belinostat also called Beleodaq (PXD-101) has received the FDA approval on 2014 (Ja et al 2003; Valente et al 2014).

In a particular embodiment, the histone deacetylase inhibitor is Entinostat (as SNDX-275 or MS-275). This molecule has the following chemical formula ($C_{21}H_2N_4O_3$) and has structure as described in Valente et al 2014.

In a particular embodiment, the histone deacetylase inhibitor is Mocetinostat (MGCD01030) having the following chemical formula ($C_{23}H_{20}N_6O$) (Valente et al 2014).

In a particular embodiment, the histone deacetylase inhibitor is Practinostat (SB939) having the following chemical formula ($C_{20}H_{30}N_4O_2$) and the structure as described in Diermayr et al 2012.

In a particular embodiment, the histone deacetylase inhibitor is Chidamide (CS055/HBI-8000) having the following chemical formula ($C_{22}H_{19}FN_4O_2$).

In a particular embodiment, the histone deacetylase inhibitor is Quisinostat (JNJ-26481585) having the following chemical formula ($C_{21}H_{26}N_6O_2$).

In a particular embodiment, the histone deacetylase inhibitor is Abexinostat (PC124781) having the following chemical formula ($C_{21}H_{23}N_3O_5$) (Valente et al 2014).

In a particular embodiment, the histone deacetylase inhibitor is CHR-3996 having the following chemical formula ($C_{20}H_{19}FN_6O_2$) (Moffat D et al 2010; Banerji et al 2012).

In a particular embodiment, the histone deacetylase inhibitor is AR-42 having the following chemical formula ($C_{18}H_{20}N_2O_3$) (Lin et al 2010).

In a particular embodiment, the activator of MHC expression is DNA methyltransferase inhibitors.

As used herein, the term "DNA methyltransferase inhibitors" refer to compounds which are capable of interacting with DNA methyltransferase (DNMT) and inhibiting their activity. DNMT are the enzymes which catalyze the transfer of a methyl group to DNA. DNA methylation serves a wide variety of biological functions. All the known DNA methyltransferases use S-adenosyl methionine (SAM) as the methyl donor.

In a particular embodiment, the DNA methyltransferase inhibitor is azacytidine, also known as 5-aza-2-deoxycytidine having the following chemical formula ($C_8H_{12}N_4O_5$) and structure in the art (Kaminskas et al 2004; Estey et al 2013).

In a particular embodiment, the DNA methyltransferase inhibitor is decitabine also known as 5-aza-2'-deoxycytidine, having the following formula ($C_8H_{12}N_4O_4$) (Kantarjian et al 2006).

In a particular embodiment, the activator of MHC expression and/or immune response is a histone-lysine N-methyltransferase enzyme inhibitor, or DNA methyltransferase inhibitor. As used herein, the term "histone-lysine N-methyltransferase enzyme inhibitor" refers to compounds which are capable of interacting with histone-lysine N-methyltransferase enzyme encoded by Enhancer of zeste homolog 1 (EZH1) and 2 (EZH2) gene that participates in DNA methylation. EZH2 catalyzes the addition of methyl groups to histone $H_3$ at lysine 27 by using the cofactor S-adenosyl-L-methionine.

In a particular embodiment, the histone-lysine N-methyltransferase enzyme inhibitor is 3-Deazaneplanocin A (DZNep, C-c3Ado). DZNep, C-c3Ado has the following chemical formula $C_{12}H_{14}N_4O_3$ and CAS number 102052-95-9 in the art.

In a particular embodiment, the histone-lysine N-methyltransferase enzyme inhibitor is UNC1999 and an inactive analog compound. UNC1999 has the following chemical formula $C_{33}H_{43}N_7O_2$ and CAS number 1431612-23-5 in the art.

In a particular embodiment, the histone-lysine N-methyltransferase enzyme inhibitor is UNC2400 and an inactive analog compound. UNC2400 has the following chemical formula $C_{35}H_{47}N_7O_2$ and CAS number 1433200-49-7 in the art.

In a particular embodiment, the histone-lysine N-methyltransferase enzyme inhibitor is tazemetostat (EPZ6438, E7438). Tazemetostat has the following chemical formula $C_{34}H_{44}N_4O_4$ and CAS number 1403254-99-8 in the art.

In a particular embodiment, the histone-lysine N-methyltransferase enzyme inhibitor is trifluoroacetate (EPZ011989). Trifluoroacetate has the following chemical formula $CF_3COONa$ and CAS number 2923-18-4 in the art.

In a particular embodiment, the histone-lysine N-methyltransferase enzyme inhibitor is EPZ005687. EPZ005687 has the following chemical formula $C_{32}H_{37}N_5O_3$ and CAS number 1396772-26-1 in the art.

In a particular embodiment, histone-lysine N-methyltransferase enzyme inhibitor is GSK343. GSK343 has the following chemical formula $C_{31}H_{39}N_7O_2$ and CAS number 1346704-33-3 in the art.

In a particular embodiment, histone-lysine N-methyltransferase enzyme inhibitor is GSK126. GSK126 has the following chemical formula $C_{31}H_{38}N_6O_2$ and CAS number 1346574-57-9 in the art.

In a particular embodiment, histone-lysine N-methyltransferase enzyme inhibitor is GSK2816126. GSK2816126 has the following chemical formula $C_{31}H_{38}N_6O_2$ and CAS number 1346574-57-9 in the art.

In a particular embodiment, histone-lysine N-methyltransferase enzyme inhibitor is ZLD1039. ZLD1039 has the following chemical formula $C_{36}H_{48}N_6O_3$ and CAS number 1826865-46-6 in the art.

In a particular embodiment, an HDACi and a DNA methyltransferase inhibitor are both used. Indeed, it has been shown that the combined use of VPA and 5-Azacytidine (an analog of the nucleoside cytidine which can be incorporated into DNA and RNA) leads to a synergetic effect on the re-expression of neo anti-embryonic antigens.

The HDACi is administered in a therapeutically efficient amount. For VPA, it may be from 10 to 15 mg/kg/day, up to 60 mg/kg/day. The plasma level of VPA should preferably be in the usually accepted therapeutic range (50 to 100 μg/mL).

In a further aspect, the method according to the invention is suitable to treat cancers expressing a large number of fetal antigens which share the expression with human fetal stem cells (e.g. NACC1, BLM, WDR33, DAZAP1, CDK1, CDC45, ZNF165, XRCC5, SMARCADI, AIMP2, CKS1B . . . ).

As used herein, the terms "cancers expressing fetal stems cells", are the cancers that are preferably targeted by the methods, vaccines and compositions herein disclosed, refer to cancer stem cells expressing a large number of fetal antigens which share the expression with human fetal stem cells. Typically, the cancer is selected from the group consisting of bladder carcinoma, breast carcinoma, cervical carcinoma, cholangiocarcinoma, colorectal carcinoma, gastric sarcoma, glioma, lung carcinoma, lymphoma, acute and chronic lymphoid and myeloid leukemias, melanoma, multiple myeloma, osteosarcoma, ovarian carcinoma, pancreatic carcinoma, prostate carcinoma, stomach carcinoma, kidney carcinoma, a head and neck tumor, and all solid tumor and hematopoietic malignancies. It is to be noted that the cells in this composition are heterogeneous in nature. More particularly, when the mutagen has been used and hence differs from a pluripotent cell composition that has been cultured according to methods known in the art, and which is homogenous.

As used herein the terms "administering" or "administration" refer to the act of injecting or otherwise physically delivering a substance as it exists outside the body (e.g., combined preparation) into the subject, such as by mucosal, intradermal, intravenous, subcutaneous, intramuscular delivery and/or any other method of physical delivery described herein or known in the art. When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

In particular embodiment, the vaccine composition (fetal stem cells+agent stimulating MHC presentation) is injected subcutaneously. Injection may be simultaneous, sequential, separate, at the same injection point or at different injection points, in the same syringe, or in separate syringes . . . .

In a particular embodiment, the follow-up treatment (administration of the compound that stimulates MHC I and/or immune system, such as an HDACi, in particular VPA) is administered by the oral route.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In a particular embodiment, the method according to the invention comprises further one or more of radiation therapy, targeted therapy, immunotherapy, or chemotherapy. Typically, the physician could choose to administer the subject with i) a population of fetal stem cells and ii) a compound selected from a group which activates MHC expression and/or immune response, as a combined preparation with radiation therapy, targeted therapy, immunotherapy, or chemotherapy.

In some embodiments, the subject is administered with i) a population of fetal stem cells and ii) a compound selected from a group which activates MHC expression and/or immune response, as a combined preparation and a chemotherapeutic agent.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalamycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylamine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and phannaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

In some embodiments, the subject is administered with i) a population of fetal stem cells and ii) a compound selected from a group which activates MHC expression and/or immune response, as a combined preparation and a targeted cancer therapy.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signalling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; ST1571), leflunomide (SU101), vandetanib (Zactima; ZD6474), bevacizumab (avastin), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the subject is administered with i) a population of fetal stem cells and ii) a compound selected from a group which activates MHC expression and/or immune response, as a combined preparation and an immune checkpoint inhibitor.

As used herein, the term "immune checkpoint inhibitor" refers to molecules that totally or partially reduce, inhibit, interfere with or modulate one or more checkpoint proteins. Checkpoint proteins regulate T-cell activation or function. Numerous checkpoint proteins are known, such as CTLA-4 and its ligands CD80 and CD86; and PD1 with its ligands PDL1 and PDL2 (Pardoll, Nature Reviews Cancer 12: 252-264, 2012). These proteins are responsible for co-stimulatory or inhibitory interactions of T-cell responses. Immune checkpoint proteins regulate and maintain self-tolerance and the duration and amplitude of physiological immune responses. Immune checkpoint inhibitors include antibodies or are derived from antibodies. In some embodiments, the immune checkpoint inhibitor is an antibody selected from the group consisting of anti-CTLA4 antibodies (e.g. Ipilimumab), anti-PD1 antibodies (e.g. Nivolumab, Pembrolizumab), anti-PDL1 antibodies, anti-TIM3 antibodies, anti-LAG3 antibodies, anti-B7H3 antibodies, anti-B7H4 antibodies, anti-BTLA antibodies, and anti-B7H6 antibodies. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CTLA-4 antibody is tremelimumab, (ticilimumab, CP-675, 206). In some embodiments, the anti-CTLA-4 antibody is ipilimumab (also known as 10DI, MDX-D010) a fully human monoclonal IgG antibody that binds to CTLA-4. Another immune checkpoint protein is programmed cell death 1 (PD-1). Examples of PD-1 and PD-L1 blockers are described in U.S. Pat. Nos. 7,488,802; 7,943,743; 8,008, 449; 8,168,757; 8,217,149, and PCT Published Patent Application Nos: WO03042402, WO2008156712, WO2010089411, WO2010036959, WO2011066342, WO2011159877, WO2011082400, and WO2011161699. In some embodiments, the PD-1 blockers include anti-PD-L1 antibodies. In certain other embodiments, the PD-1 blockers include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224 is a fusion protein of B7-DC; an antibody Fc portion; BMS-936559 (MDX-1105-01) for PD-L1 (B7-H1) blockade. Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207:2187-94). In some embodiments, the immunotherapeutic treatment consists of an adoptive immunotherapy, as described by Nicholas P. Restifo, Mark E. Dudley and Steven A. Rosenberg ("Adoptive immunotherapy for cancer: harnessing the T cell response, Nature Reviews Immunology, Volume 12, April 2012). In adoptive immunotherapy, the patient's circulating lymphocytes, or tumor-infiltrated lymphocytes, are isolated in vitro, activated by lymphokines such as IL-2 and readministered (Rosenberg et al., 1988; 1989). The activated lymphocytes are most preferably be the patient's own cells that were earlier isolated from a blood sample and activated (or "expanded") in vitro.

In some embodiments, the subject is administered with i) a population of fetal stem cells and ii) a compound selected from a group which activates MHC expression and/or immune response, as a combined preparation and a radiotherapeutic agent.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

Pharmaceutical and Vaccine Compositions

The compounds which activate MHC expression and/or immune response and the population of fetal stem cells as described above may be combined with pharmaceutically acceptable excipients, and optionally sustained-release matrices, such as biodegradable polymers, to form pharmaceutical compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

More particularly, the population of fetal stem cells and the compound which activates MHC expression and/or immune response are formulated on a vaccine composition. Accordingly, the invention relates to a vaccine composition comprising i) a population of fetal stem cells and ii) a compound selected from a group which activates MHC expression and/or immune response.

In a particular embodiment, the vaccine composition according to the invention comprising i) fetal stem cells and ii) acid valproic.

In a particular embodiment, the vaccine composition according to the invention comprising i) fetal stem cells expressing neo-antigens, in particular enhanced by mutagen agents or genetic modification and ii) valproic acid.

The composition may also comprise 5 Azacytidine.

Moreover, the vaccine composition of the present invention can be used in a subject suffering from a cancer as described above.

The vaccine composition according to the invention can be formulated with the physiological excipients set forth above in the same manner as in the immunogenic compositions. For instance, the pharmaceutically acceptable vehicles include, but are not limited to, phosphate buffered saline solutions, distilled water, emulsions such as an oil/water emulsions, various types of wetting agents sterile solutions and the like. Adjuvants such as muramyl peptides such as MDP, IL-12, aluminium phosphate, aluminium hydroxide, Alum and/or Montanide® can be used in the vaccines.

The vaccine composition according to the invention can be administered subcutaneous (s.c), intradermal (i.d.), intramuscular (i.m.) or intravenous (i.v.) injection, oral administration and intranasal administration or inhalation. The administration of the vaccine is usually in a single dose. Alternatively, the administration of the vaccine of the invention is made a first time (initial vaccination), followed by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 recalls (subsequent administration), with the same population of stem cells, the compound which stimulates the immune system or a combination of thereof and/or with a further one or more of radiation therapy, targeted therapy, immunotherapy, or chemotherapy.

The vaccine composition is also provided in a kit. The kit comprises the vaccine composition and an information leaflet providing instructions for immunization. The kit comprises also the all materials for the administration of the products.

The invention will be further illustrated by the following figures and examples. However, these examples and figures should not be interpreted in any way as limiting the scope of the present invention.

FIGURES

Figure 2:
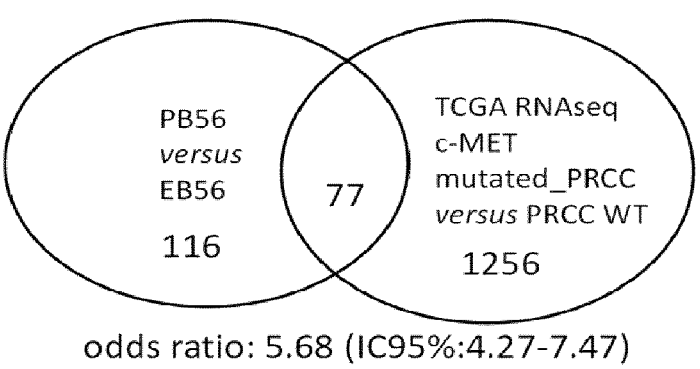
Figure 3:
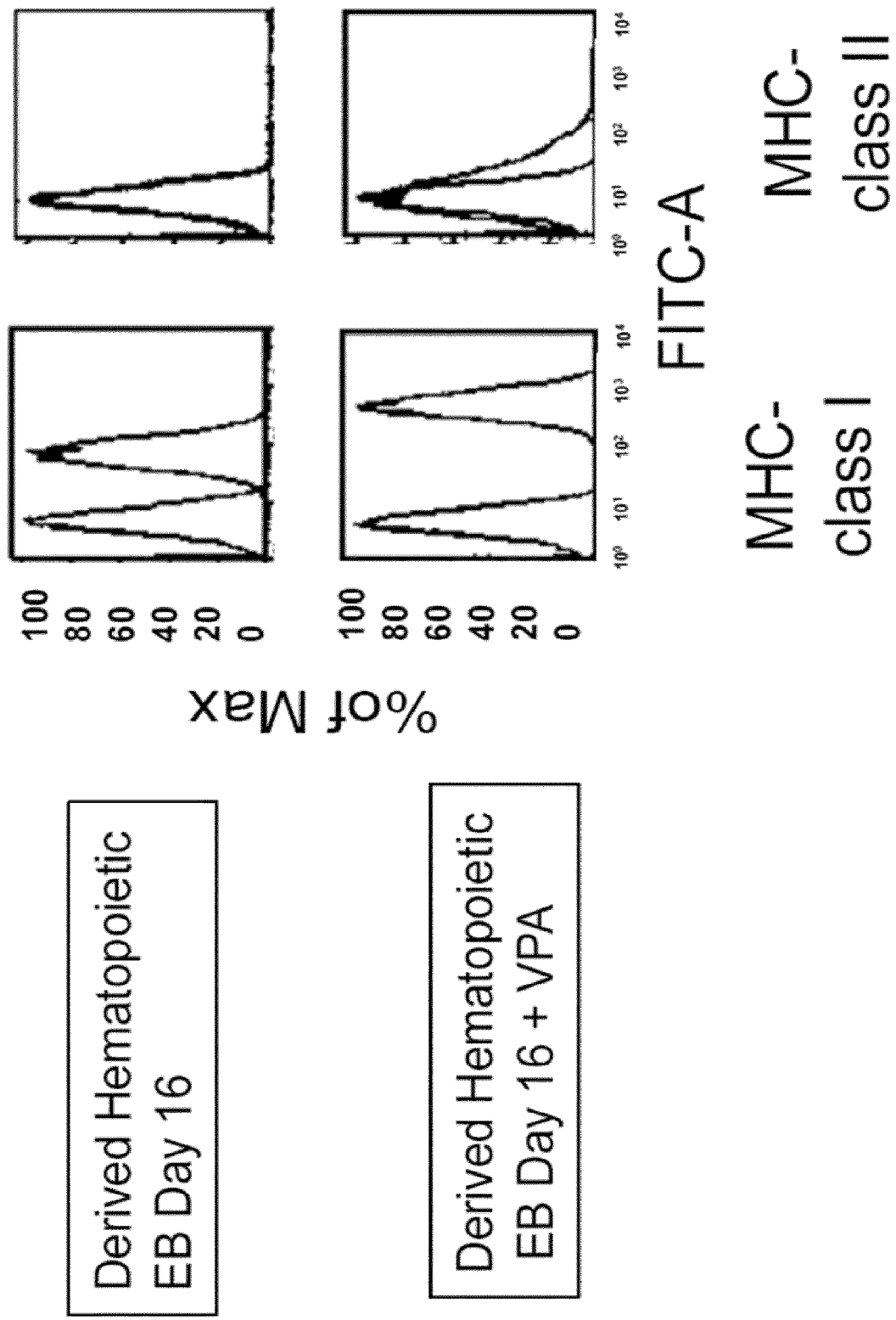

FIG. 1: Transcriptome identified during renal organoid specification of c-MET-mutated IPSCs. Expression heatmap (Euclidean distances) of differentially expressed genes between PB56 (c-MET mutated IPSCs) and EB56 (Embryonic body derived fetal renal organoid from the parental c-Met IPSCs);

FIG. 2: Venn diagram of the meta-analysis between the transcriptome of cMET-IPSCs and that of primary papillary renal carcinoma (PRCC) samples. p-value of the Embryonic body fetal renal organoid transcriptomic signature in PRCC expression profile was calculated by hypergeometric test of Fisher;

FIG. 3: Expression of CMH Class I and II in presence and absence of HADCi (VPA) in cultured human hematopoietic fetal stem cells (EBs) obtain after differentiation of IPSCs.

Figure 4:
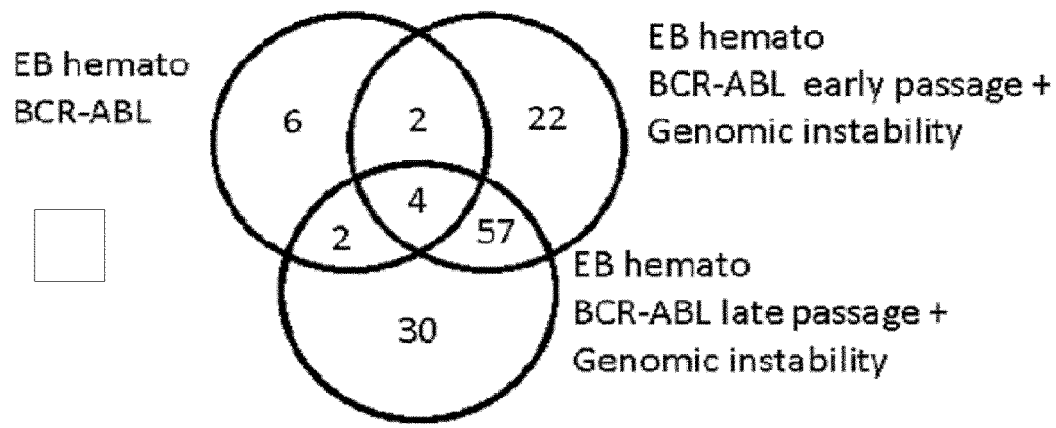

FIG. 4: Genomic variants in human derived hematopoietic fetal stem cells induced by mutagen agents in BCR-ABL positive IPSCs. Venn diagram of genes found to be affected by genomic variants by exome sequencing as compared to the parental BCR-ABL positive IPSCs, 3 different experimental conditions were tested: derived hematopoietic EBs without genomic instability (blue), derived fetal hematopoietic EBs in early passage with genomic instability induced by ENU (green), derived fetal hematopoietic EBs in late passage with genomic instability induced by ENU (red).

Figure 5:
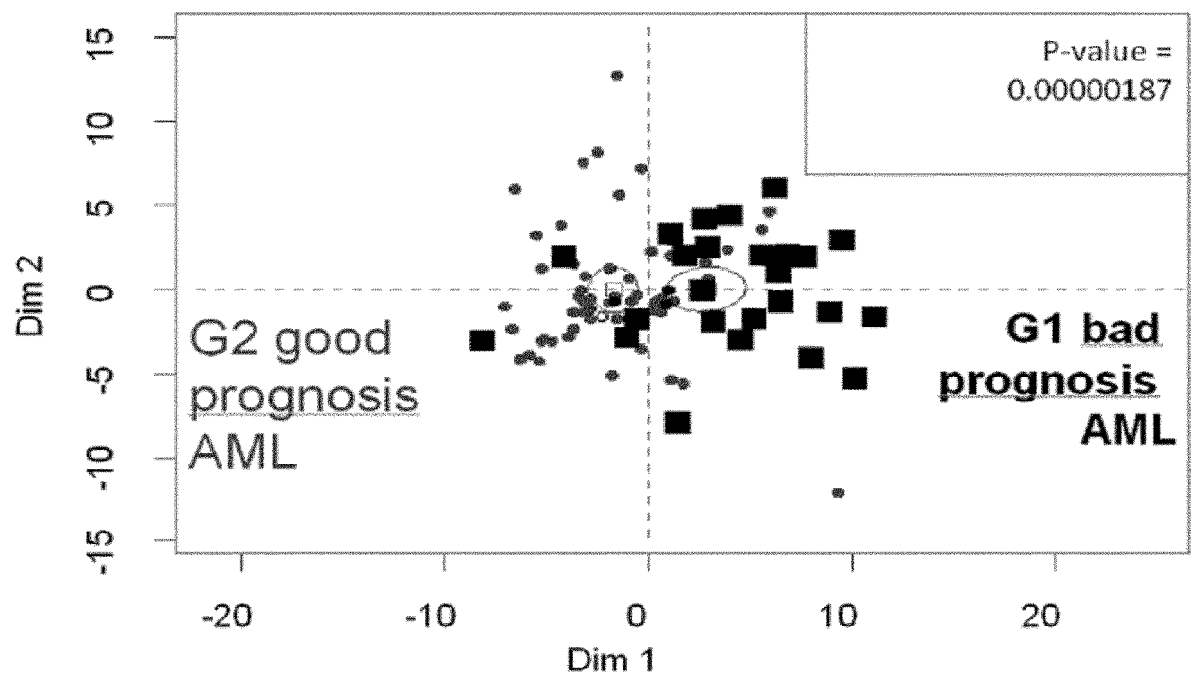

FIG. 5: Unsupervised principal component analysis performed on 123 genes in transcriptome experiments of IPSCS BCR-ABL treated by ENU as compared to AML transcriptome (GSE10358).

The affected 123 genes in the "blast crisis in dish" model integrated in AML patient blast transcriptome analysis predict a prognosis discrimination (log rank p value=1E-4).

Small grey spots: G2 good prognosis AML. Large black spots: G1 bad prognosis AML.

Abscissa: first dimension, as expressed in arbitrary units of factorial analysis (principal component analysis); Ordinate: second dimension, as expressed in arbitrary units of factorial analysis (principal component analysis).

Figure 6:
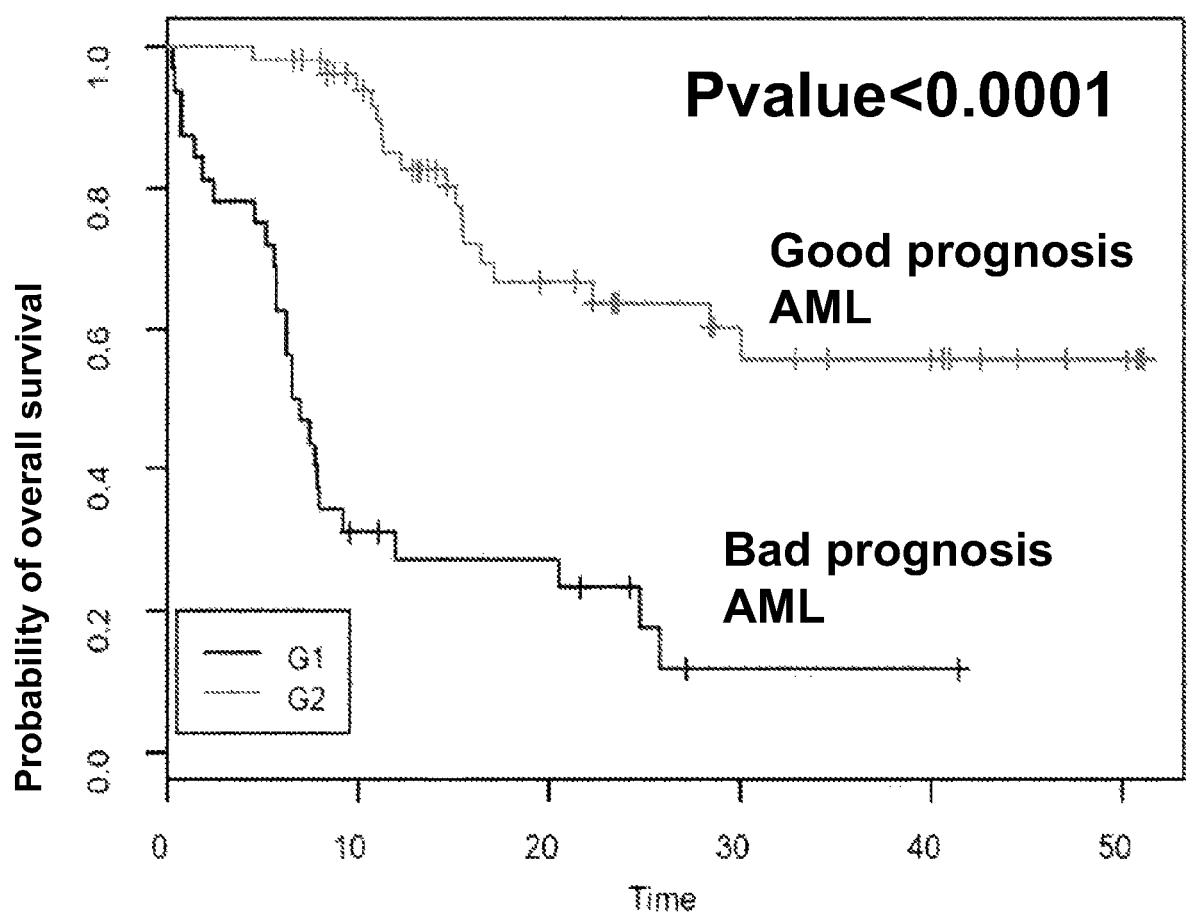

FIG. 6: Overall survival of AML patients with good and bad prognosis signature.

Upper curve: Good prognosis AML (G2). Lower curve: Bad prognosis AML (G1).

Abscissa: Probability of overall survival; Ordinate: time, as expressed in months.

Figures 7, 8:
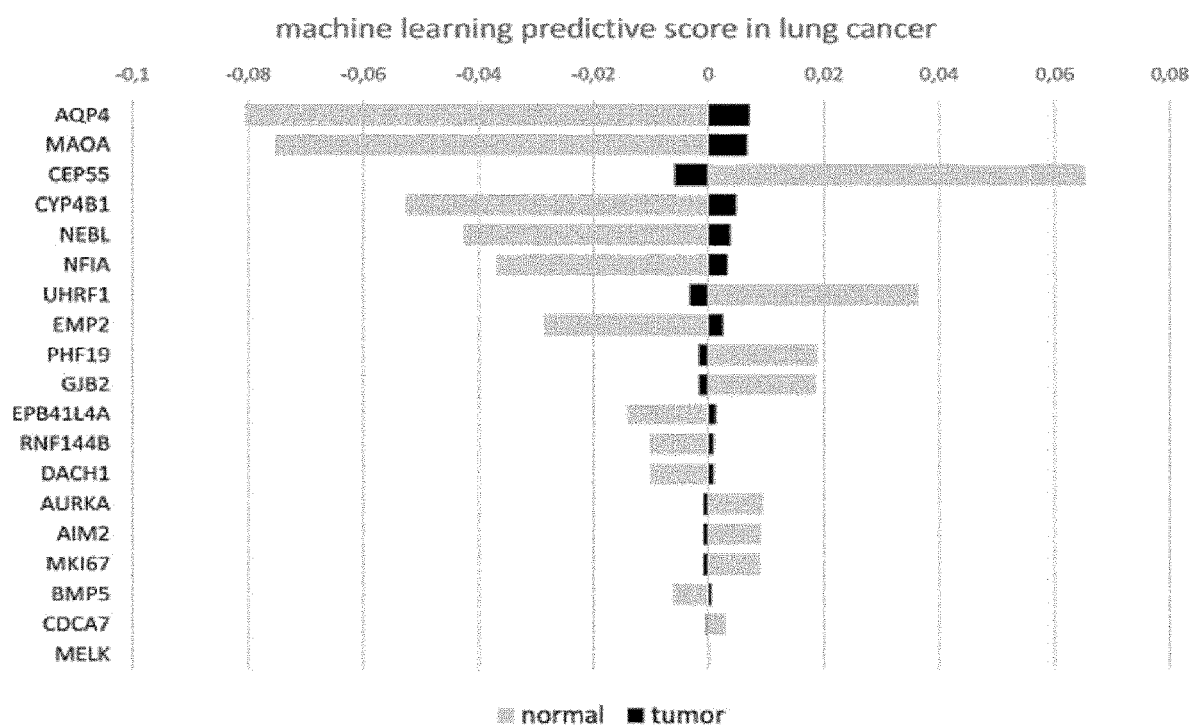

FIG. 7: Signature between lung organoid obtained from iPSC and lung cancer showing 19 common genes FIG. 8: Concentration of HDACi used to evaluate the expression of MHC1 HLA-ABC.

Figure 9:
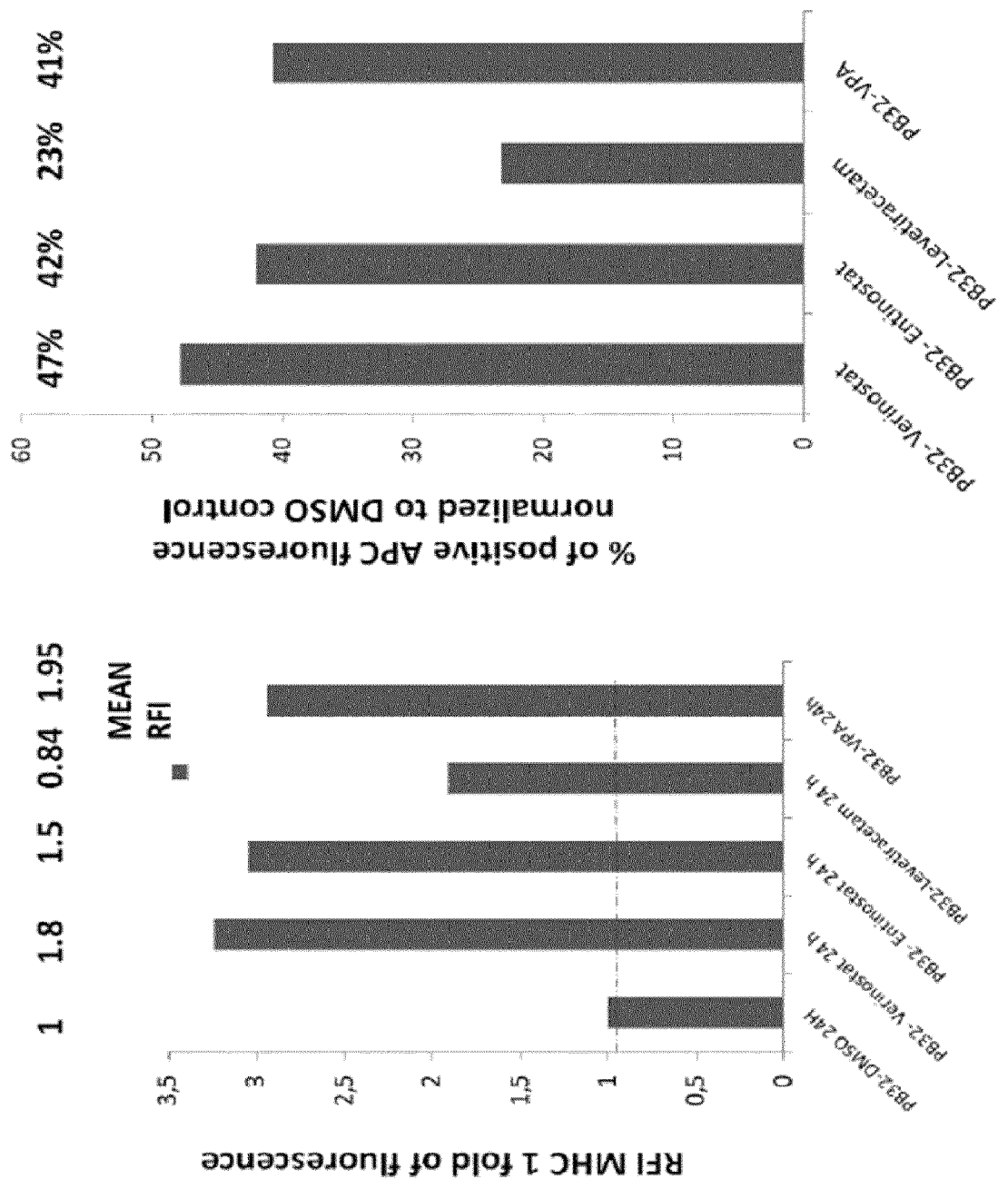

FIG. 9: Expression of MHC1 HLA ABC in presence and absence of HADCi on CML-derived IPSC (PB32).

Left panel: Normalization of the RFI MEAN to the DMSO control of iPSC (PB32) treated with 4 different HDACi using a MHC I HLA-ABC monoclonal antibody coupled with APC. Ordinate: RF/MHC1 fold of fluorescence.

Right panel: % of MHC1 expression normalized to the DMSO control of a CML-derived IPSCs (PB32) exposed to 4 different HDACi. Ordinate: % of positive APC fluorescence normalized to DMSO control.

Figure 10:
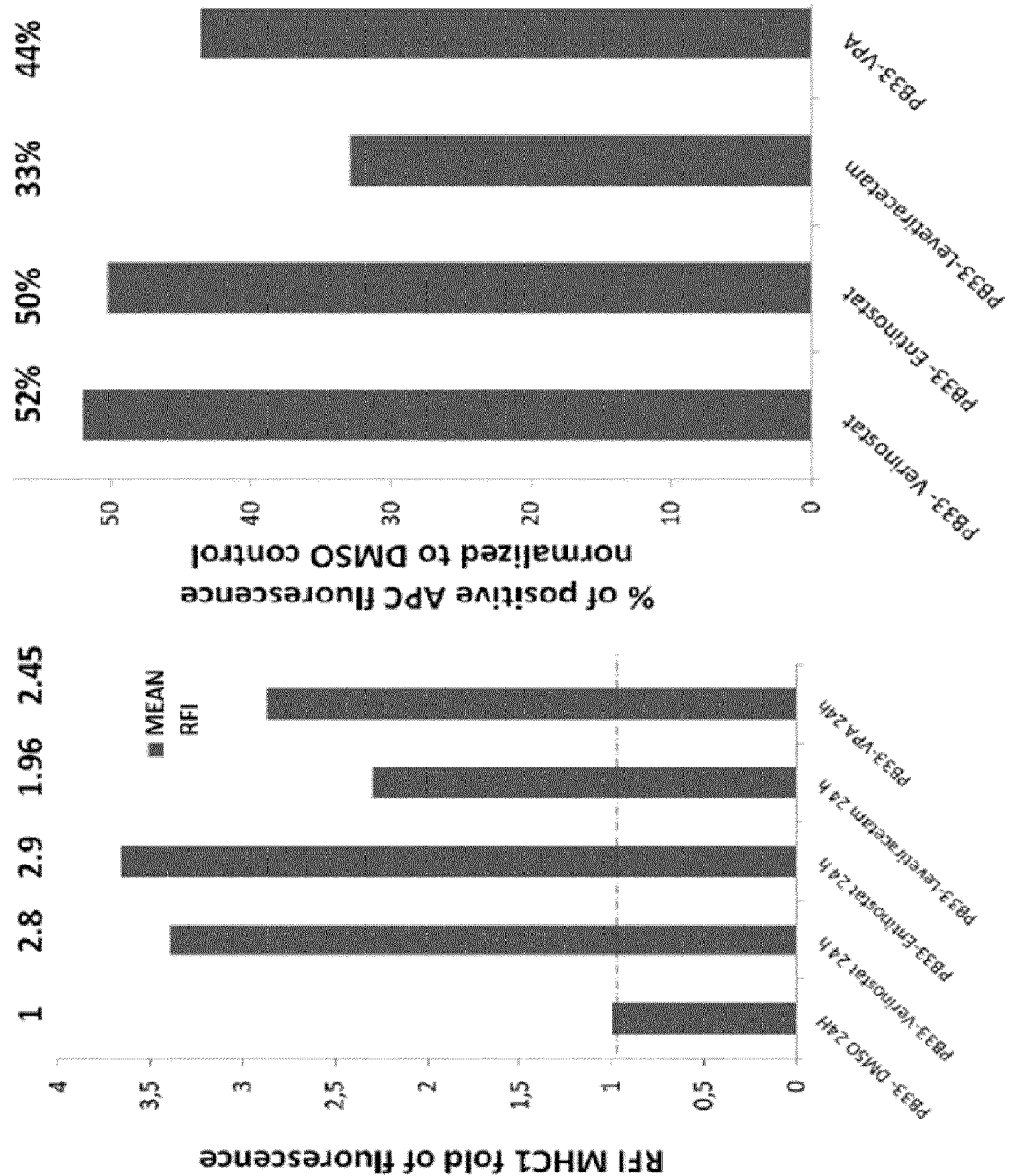

FIG. 10: Expression of MHC1 HLA ABC in presence and absence of HADCi on IPSC with no genomic alteration (PB33).

Left panel: Normalization of the RFI MEAN to the DMSO control of IPSC (PB33) treated with 4 different HDACi using a MHC I HLA-ABC monoclonal antibody coupled with APC. Ordinate: RF/MHC1 fold of fluorescence.

Right panel: % of MHC1 expression normalized to the DMSO control of a IPSCs (PB33) exposed to 4 different HDACi. Ordinate: % of positive APC fluorescence normalized to DMSO control.

Figure 11:
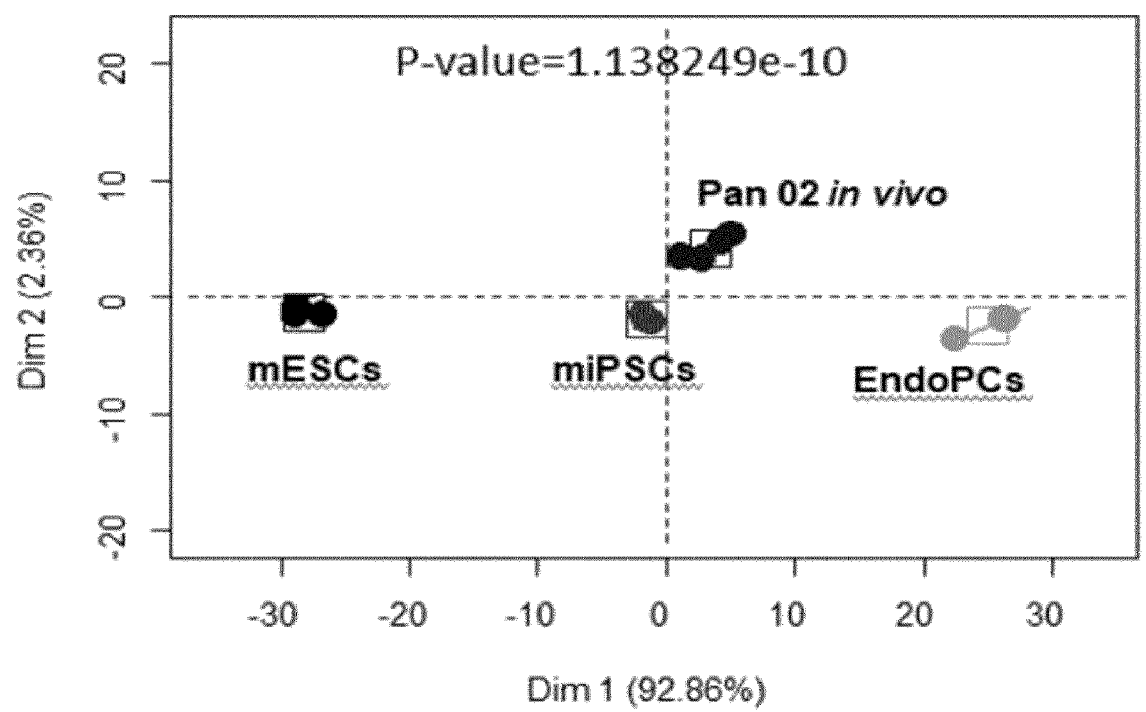

FIG. 11: Unsupervised principal component analysis performed on 392 genes in transcriptome experiments of murine IPSCS, murine ESCs, engraft Pan02 and murine Endodermic progenitors cells (EndoPCs).

Abscissa: first dimension, as expressed in arbitrary units of factorial analysis (principal component analysis); Ordinate: second dimension, as expressed in arbitrary units of factorial analysis (principal component analysis).

Figure 12:
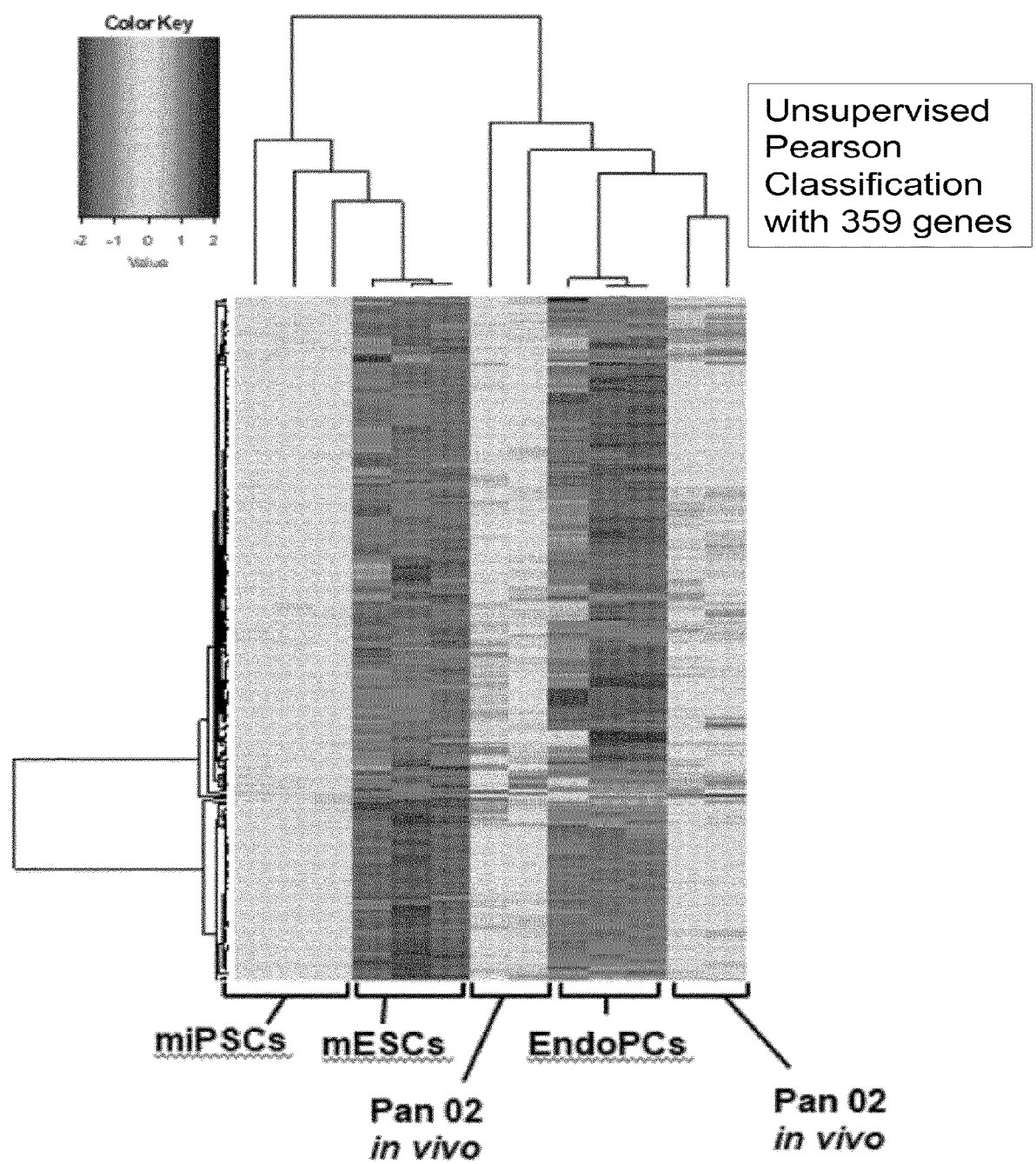

FIG. 12: Gene expression heatmap and unsupervised classification performed with the 359 genes between murine IPSCS, murine ESCs, engraft Pan02 and murine Endodermic progenitors cells (EndoPCs)

Figure 13:
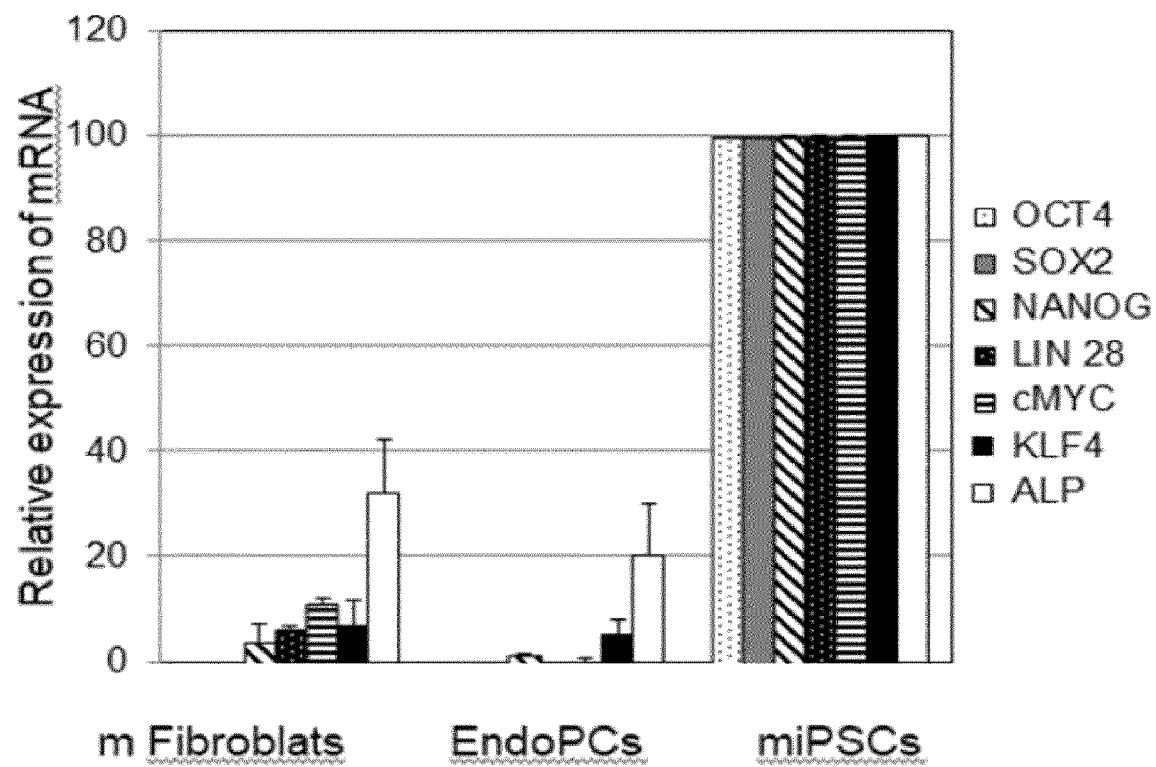

FIG. 13: Expression of pluripotent genes by RT PCR on murine fibroblasts, iPSC, and EndoPCs.

Expression of iPSC-enriched genes by quantitative RT-PCR in EndoPCs in comparison to murine iPSCs and to primary murine C57BL/6 fibroblasts. Seven different factors including OCT4, SOX2, NANOG, LIN28, CMYC, KLF4 and Alkaline phosphatase (ALP) were quantified and subsequently normalized to the mRNA level found in miPSCs (value of 100). Ordinate: relative expression of mRNA, as expressed in arbitrary units. Abscissa, groups of bars from left to right: (i) m Fibroblasts; (ii) EndoPCs; (iii) miPSCs. For each group of bars, from left to right: (i) OCT4, (ii) SOX2, (iii) NANOG, (iv) LIN 28, (v) cMYC, (vi) KLF4, (vii) ALP.

Figure 14:
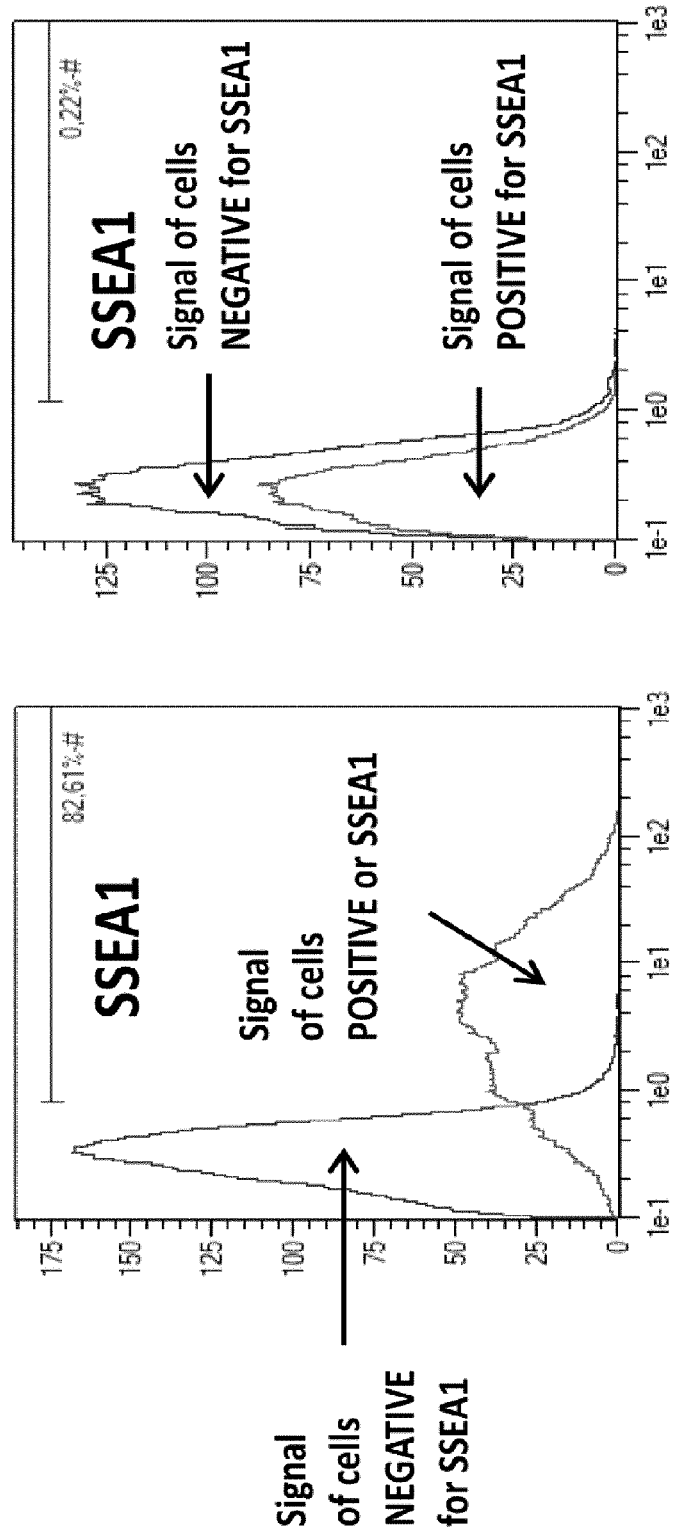

FIG. 14: Expression of the mESCs marker SSEA-1 in EndoPCs by flow cytometry analysis compared to ESCs.

Left panel: mESC (CK35); Right panel: EndoPCs. Ordinate: fluorescence signal intensity (log), as expressed in arbitrary units. Abscissa: amplitude of the signal.

Figure 15:
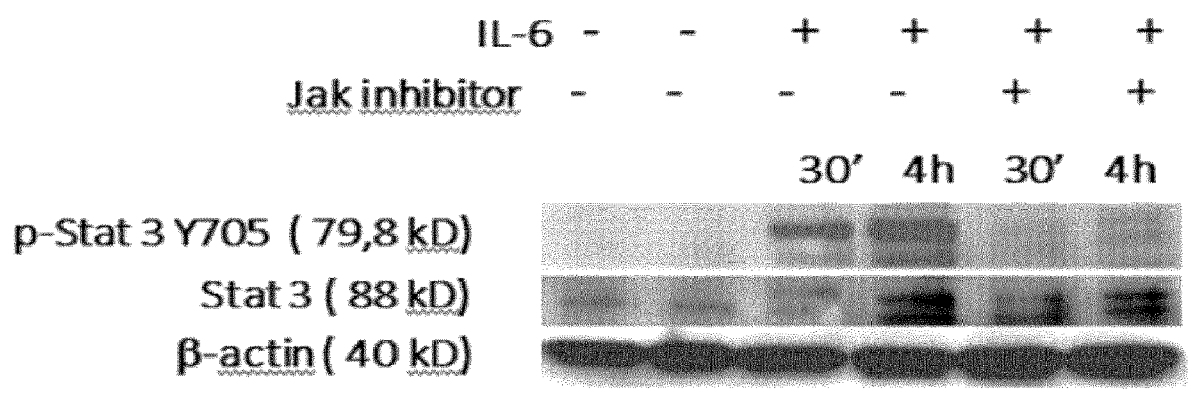

FIG. 15: Western blot analysis for STAT3, pSTAT3 (Y705) and R actine on Pan 02 expanded with or without 100 ng/ml of IL6 performed after 0.5 and 4 hours.

Pan02 cells were incubated with (raws from left to right): (i) no IL-6, no Jak inhibitor, (ii) no IL-6, no Jak inhibitor, (iii) IL-6, no Jak inhibitor, (iv) IL-6, no Jak inhibitor, (v) IL-6, Jak inhibitor, (vi) IL-6, Jak inhibitor. Lines, from top to bottom: (i) p-Stat 3 Y705, (ii) Stat 3, (iii) β-actin.

Figure 16:
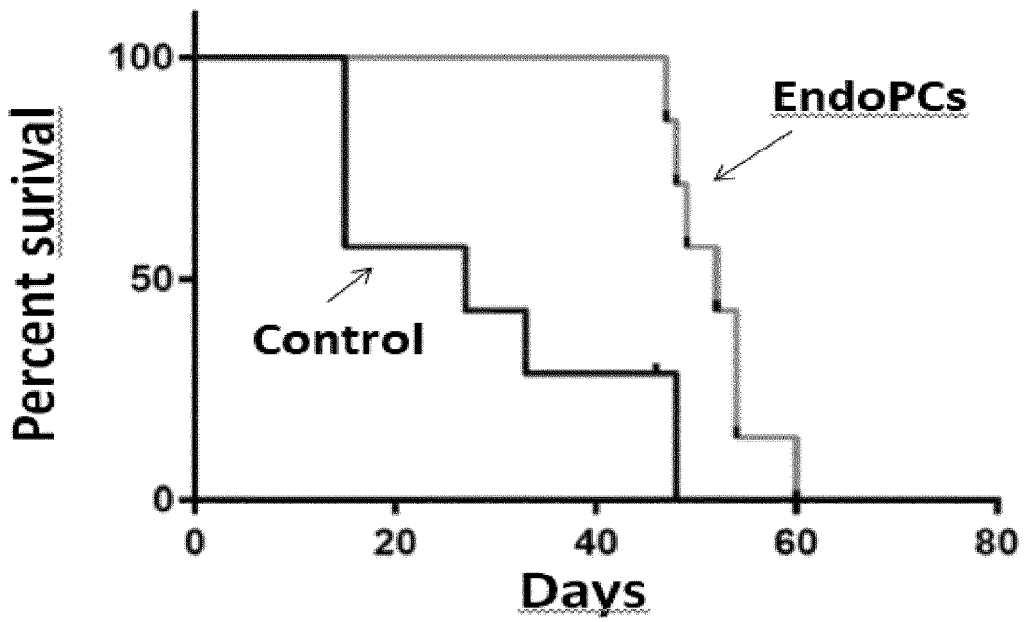

FIG. 16: Overall survival of mice vaccinated with 2 boosts of EndoPCs compared to the untreated mice (n=8).

Ordinate: percent survival; Abscissa: time, as expressed in days.

Figure 17:
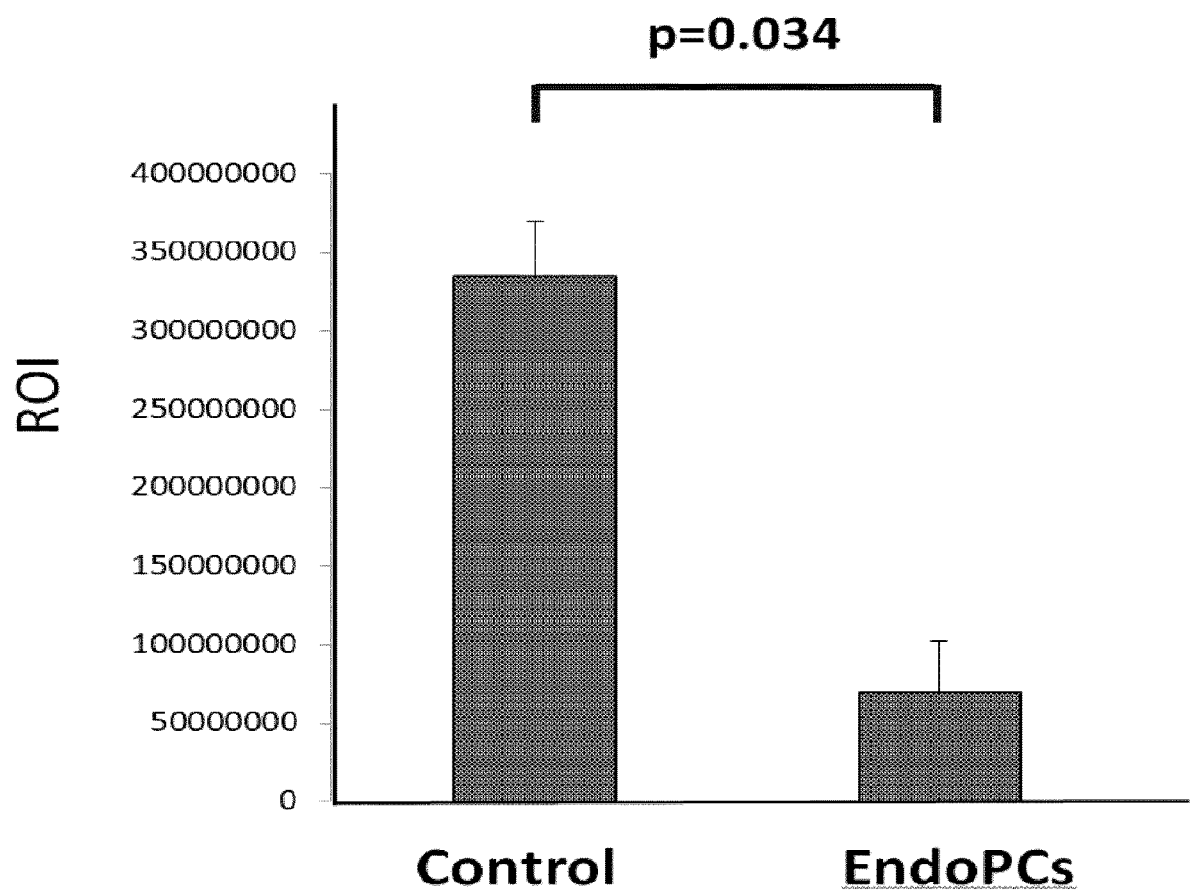

FIG. 17: Quantification of The Region of Interest (ROI) by bio luminescence measuring the surface intensities on the pancreas of treated mice compared to the control mice.

Ordinate: Region Of Interest (ROI) surface intensity, as expressed in arbitrary units.

Figure 18:
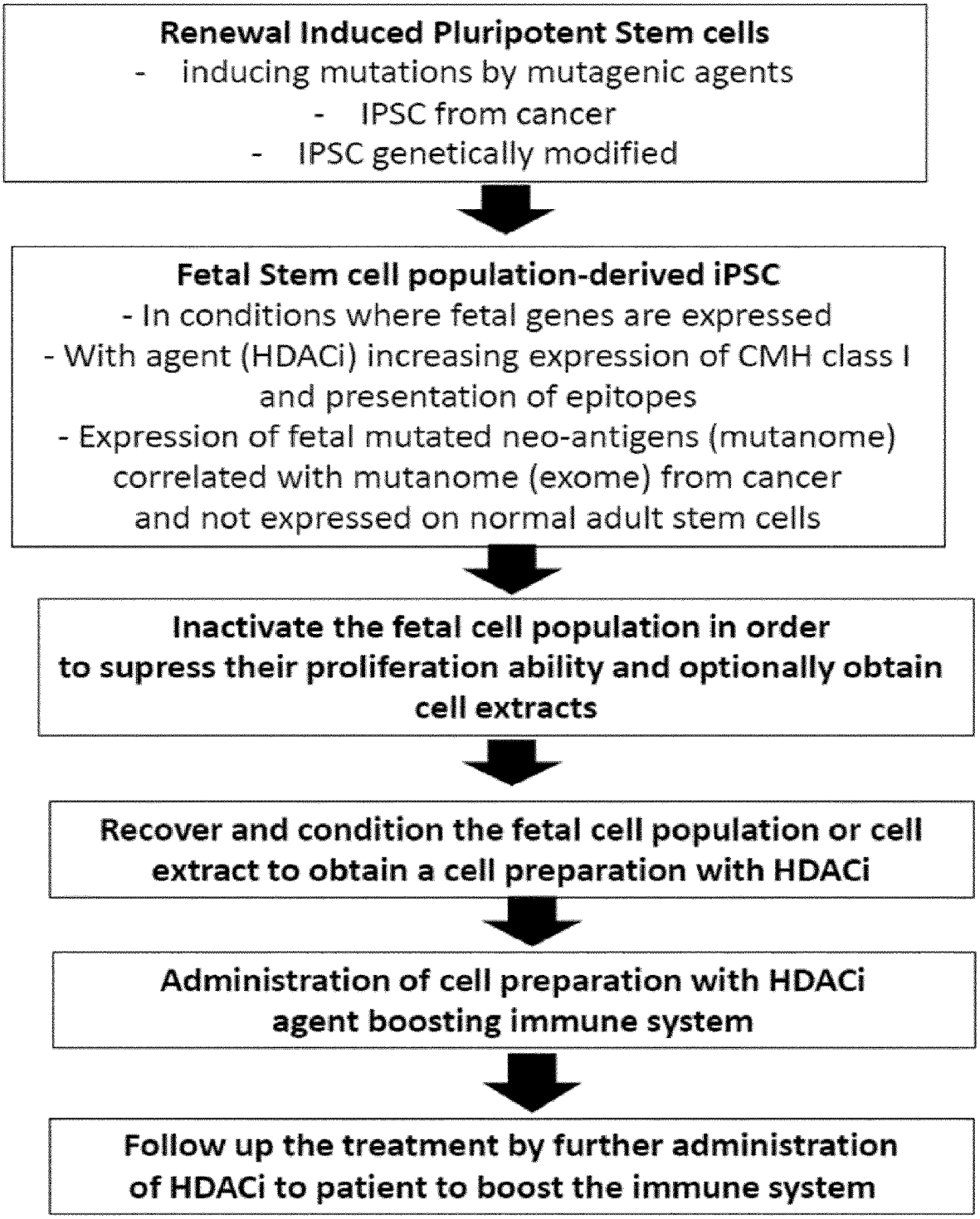

FIG. 18: This figure represents different steps to obtain fetal stem cells derived from the pluripotent stem cells.

EXAMPLES

Example 1

Characterization of Fetal Antigens from Derived Renal Oragnoids Carrying c-MET Mutation.

We have generated an iPSC line with hereditary c-MET mutation by reprogramming blood cells from a donor with type 1 papillary renal carcinoma (PRCC) using Sendai virus-mediated pluripotent gene transfer. We designed a 3D-culture system to induce the differentiation of c-MET iPSC into renal organoids, thus composed of fetal cells. We demonstrated that iPSC-derived renal organoids expressed markers of renal progenitors with glomerular and tubular structures. Transmission electron microscopy analyses confirmed the presence of tight junctions in tubular structures. Gene-array analysis was performed in renal organoids (EB56) and parental pluripotent stem cells (PB56). Supervised analysis by ranking products algorithm between the iPSC with c-met mutation (PB56) and derived fetal renal organoids containing committed nephron progenitors allowed to identify 196 differential expressed gene probes: 148 were found down regulated in EB56, as compared to IPSCs PB56 and a minority of them, 48 were found up regulated in EB56 as compared to IPSCs PB56 (FIG. 1). This confirm that fetal renal organoids have lost the pluripotency genes form iPSC and acquired fetal genes related to the committed renal tissue.

Machine learning supervised by c-MET status performed on PRCC RNAseq samples allowed to characterize 1333 predictive genes with a minimum error of misclassification. Meta-analysis between c-MET-mutated IPSCs signature and PRCC signature revealed a significant enrichment of IPSCs profile as predictive of c-MET mutated PRCC tumor status (Fold of enrichment: 5.68; p-value<2.2E-16, (FIG. 2). The characterized fetal genes from renal progenitors commonly associated to reported cancer genes present in primary adult renal carcinoma are at least in the following group: TRAPPC4, MX1, ITSN1, DNAJC7, TAF15, TMEM88, CRYM, PRTG, TYRO3 C12ORF60, FJX1, ADM, FAM45A, ASS1, CA2, ZFHX4, CLVS1, NRG1, EZH2, SLC22A23, MSH5, FBN2, GTF2H2, LIX1, HESX1, FZD5, LRP2, RHOQ, NUAK2, ILF2, ACP6, RPL5, NMNAT1, ID1, U2AF2, KLHL14, CDH2, GREBIL, ARRDC4, THBS1, BMP4, LRIG3, SOX5, SF1, LGR4, MGEA5, BCORL1, STOM, GLIS3, ANXA1, KDM4C, SDC2, TMEM130, MAGI2, GLI3, HEY2, TPBG, ID4, MYLIP, ENC1, EGR1, CDH6, NPY1R, SEL1L3, LRAT, CLDN1, CEP97, BHLHE40, ARL5A, ARL4C, ZNF385B, LYPD1, B3GNT7, INSIG2, ARHGAP29, NOTCH2, IF116.

These results confirm that fetal renal organoids derived from a c-MET-mutated IPSCs are relevant fetal cells to model papillary renal cell carcinoma expressing at least 77 common cancer associated fetal neo-antigens allowing to prepare cancer cell vaccine product or cell extract for renal carcinoma associated with c-met mutation.

Example 2

Common Mutanome in Derived Fetal Hematopoietic Stem Cells with Acute Myeloid Leukemia (AML).

We developed an induced pluripotent cell (IPSCs) model of chronic myeloid leukemia to model progression of the disease. BCR-ABL fusion protein expression increases during chronic myeloid leukemia progression and this phenomenon is well known to induce genomic instability and promote apparition of secondary genomic events compatible with blast transformation leading to acute myeloid leukemia.

Human pluripotent stem cells carrying the Bcr-Abl oncogene were cultured and expanded with mutagen agents (ENU) to induce genomic instability and enhance somatic mutations during the successive divisions. Committed hematopoietic progenitor fetal cells were produced by using the technology of embryonic bodies (EB) in the presence of growth and morphogens. Embryonic bodies (EBs) at day 2-3, corresponding to hemangioblast stage, blastic colonies, and EBs at Day 4-20 were analyzed. Hematopoietic EBs were characterized for their hematopoietic markers CD34, C43, CD45, by FACS analysis. Hematopoietic potential was confirmed by the colony forming assays by counting the number of CFC and analyzing the type of CFC. We show that ENU can induce genomic instability and allowed to reproduce a blast crisis in the dish, with a renewal blast hematopoietic myeloid progenitors in culture. The presence of VPA in cultured hematopoietic EBs allowed to enhance the amount of CMH Class I and with a lower efficiency for the CMH Class II as described by FACS analysis (FIG. 3).

Gene array, exome and CGH array was performed on derived fetal hematopoietic EBs progenitors at Day 16, obtained from IPSC at early passage (>20 Passages) and IPSC at late passages (>100 Passage) after exposing to ENU. Whole exome analysis was performed on DNA of parental IPSCs as compared to differentiated Embryonic Bodies with or without genomic instability, and EBs from IPSC cultured at early and late passages. Next generation sequencing was performed on Illumina Technologies by pair end sequencing and using CASAVA pipeline aligned on HG19 genome version. Genomic variants were selected with a frequency less than 0.01 for the general human population in EXAC database.

We compared genomic variations in hematopoietic EBs to the parental IPSCs with a difference of allele frequence more 0.10. As shown in FIG. 4 and Table 1, a few genomic variations were identified in hematopoietic EBs generated from BCR-ABL positive IPSC: 14 genes were found affected by 9 missense single nucleotide variations and by 5 frameshift.

On the other hand, after exposition to ENU, IPSC (<20 passages and >100 passages) were differentiated into hematopoietic fetal stem cells (EBs) and mutanome signature was compared with derived EBs from parental IPSC without ENU. ENU has been shown to induce genomic instability in hematopoietic EBs a high number of genomic variations and somatic mutations. Importantly, we found similar mutations in derived hematopoietic EBs from IPSC at early passages and late passages, indicating a stable mutanome during scalable expansion of iPSC (FIG. 4 and Table 1).

A total of 123 genomic variations were found in EBs from IPSCs treated by ENU comprising coding missense and stop gained and frameshift. These genomic variations are commonly expressed and reported in primary acute leukemia with at least: ARHGEF10L:221656_s_at, TRIM66:213748 at, ARHGEF10L:1570511 at, NKAIN3:1553241_at, ITGA7:216331_at, GGT1:211417_x_at, PDZD7:220555_s_at, MUC4:235055_x_at, GGT1:215603_x_at, MUC2:204673_at, NECAB3:210720_s_at, GGT1:208284_x_at, MNT:204206_at, GGT1:207131_x_at, ITGA7:209663_s_at, BTNL9:230992_at, FNBP1:230086_at, GLTSCR1:219445 at, NECAB3:223954_x_at, COPZ2:219561_at, ZFP36:201531_at, MIB2:241541_at, ABCC12:1553410_a_at, IGFN1:1563098_at, LRRK2:229584_at, MNT:236749_at, RIN3:220439_at, GGT1:233837 at, KIF5C:1557089_at, ANK2:202921 s_at, HDAC7:236326 at, MUC20:1558220_at, SDCCAG3:230058 at, GGT1:209919_x_at, RIN3:1562005 at, DNAI1:233195_at, DNAI1:220125_at, BTNL9:241496_at, ABTB2:232624_at, MC2R:208568_at, DOCK4:244840_x_at, FSD1L:230904_at, HDAC7:217937_s_at, CRP:205753_at, PPP1R3A:206895_at, SLC22A17:221106_at, PITPNM1:203826_s_at, BTBD7:224943_at, MIB2:241377_s_at, A2M:1558450 at, CTDSP2:208735 s_at, IFNA14:208182_x_at, KIF5C:203130_s_at, MUC20:243774_at, THNSL2:239949_at, KIF5C:203129_s_at, GTF3C3:1555439_at, NRXN1:1558708_at, MED26:1559593_a_at, FNBP1:230389_at, TMCO3:230317_x_at, PPP1R3A:211169_s_at, ING1:208415_x_at, ZNF292:

1562991_at, RBL1:1555004a_at, CD109:239719 at, CD109:229900 at, FOXRED2:233250_x_at, PLIN2: 209122_at, ZNF85:1554445_at, SESN1:218346_s_at, TMCO3:220240_s_at, MED26:231724_at, CD109: 226545_at, CENPE:205046_at, ING1:210350_x_at, TMCO3:226050_at, FOXRED2:220707_s_at, GTF3C3: 222604_at, BTBD7:224945_at, CDC27:217881_s_at, STOM:201061_s_at, CDC27:217880 at, ZNF317: 1555337_a_at, TET1:228906_at, LRBA:214109_at, MED4: 217843_s_at, CDC27:217879_at, ZNF317:225296_at, ZNF292:212366_at, MED4:222438_at, BCR:226602_s_at, STOM:201060_x_at, BCR:202315_s_at, ZNF85: 206572_x_at, BCR:217223 s_at, HPRT1:202854_at, LRBA:212692_s_at, GTF3C3:218343_s_at, NASP: 201969_at, NASP:201970_s_at, MSH2:209421_at.

These affected 123 genes in the "blast crisis in dish" model integrated in AML patient blast transcriptome analysis predict a prognosis discrimination (p-value=0.00000187, FIG. 5) on overall survival (log rank p-value=1E-4, FIG. 6).

These results confirm that neo-antigens affected by genomic variations in IPSCs-derived hematopoietic EBs reproduce similar fetal neo-antigens expressed in AML. Vaccine products such as irradiated cells or cell extract (AND, ARN, Proteins), or neo-epitope and peptides preparation can thus be produced from this modified engineered fetal hematopoietic cells. This relevant fetal hematopoietic cell can thus be used to stimulate the immune response against acute leukemia by the vaccination treatment strategy.

| IPSCs BCR-ABL | EB in Hematopoietic differentiation | EB in Hematopoietic differentiation early passage with genetic instability | EB in Hematopoietic differentiation late passage with genetic instability |
|---|---|---|---|
| stop gained | 0 | 4 | 3 |
| missense | 9 | 77 | 88 |
| frameshift | 5 | 5 | 5 |
| SUM of alterations | 14 | 86 | 96 |
| number of genes affected total affected genes n = 123 | 14 | 84 | 92 |

Table 1: Summary of genomic modifications detected by exome sequencing as compared to the parental BCR-ABL Positive IPSCs: by row numbers of different types of genomics variations were described for each process samples (hematopoietic EB:embyonic bodies) as compared to the genome of the parental IPSCs from which they were derived.

Example 3

Common Gene Expression in Derived Fetal Lung Organoid with Lung Cancer

We investigated a transcriptome analysis of lung organoid derived from IPSCs (and thus composed of fetal cells) in order to predict lung cancer signature: LIMMA algorithm after multi-testing correction by False discovery rate (FDR) identified 8372 variables genes between sorted cells and cell culture from passages 0 to 5. Conjointly SAM algorithm found 5619 differential expressed genes between lung tumors and normal lung tissue (FDR<0.05, n=246 samples). Nested analysis on intersection between alveolar organoid and lung cancer signature was tuned with machine learning leave one out algorithm from Stanford identified. A common signature of 19 predictive genes was found with a minimum of misclassification error less than 9% (FIG. 7).

Example 4

HDAC Inhibitors Increase the Immunogenicity of the Vaccine

Higher expression of MHC I in cells used as a vaccine will allow to enhance the presentation of neo-antigens associated with MHC-I to APC/Dendritic cells to induce TH1 immune response. For this purpose we tested four different HDACi to check their capacity to increase the expression of MHC 1 on two independent iPSCs. One iPSCs having no genetic alterations (PB33) and one iPSCS caring a fusion product of BCR-ABL that was produced from a patient with a CML disease (PB32).

Four HDACi were tested including verinostat, Entinestat, Leviteracetam and Valproic acid at a dose of 1 to 1.5 µM (FIG. 8). The expression of MHC1 HLA ABC was quantified by flow cytometry analysis after 24 h of culture showing that MHC1 have been increased by 23 to 52% (FIGS. 9 and 10, right panels) for both IPSCs. For each cell lines the normalization of the relative fluorescence intensity (RFI) mean to the DMSO control shows an increase of the MHC1 of 0.84 to 2.45 fold (FIGS. 9 and 10 left panel).

Example 5

Vaccination with Autologous Endodermal Progenitor Cells in Combination with Valproic Acid (VPA) Generates an Anti-Tumoral Response Against Ductal Pancreatic Adenocarcinoma (PDAC).

We have produced endodermal progenitor cells (EndoPCs) from murine tail fibroblasts-derived iPSCs and from murine differentiated hepatocytes by using viral vector expressing Oct4/Sox2/cMyc/Kfl4 transcriptional factors. These progenitors are fetal cells. In order to highlight pancreatic tumor expression profile of EndoPCs, its transcriptome was associated with a Pan02 cells that were engrafted into syngeneic C57BL/6 mice as compared to stem cell expression profile of iIPSCs derived from tail murine fibroblast associated to murine embryonic stem cell (D3). On combined and cross batch normalized transcriptome matrix, a supervised ANOVA between the 4 sample groups was performed with a p-value threshold less than $10^{-4}$ and implementation of 500 permutations between groups. A list of 3230 gene identifiers was found significantly variable between the 4 experimental conditions (data not shown). In a second time, on these variable expression profile SAM supervised algorithm was employed to found significant differential expressed genes between following groups: (EndoPCs+Pan02 in vivo) versus (D3-ES+murine_iPSCs) with a FDR less than 1 percent. With these analyses, a pancreatic tumor gene expression profile of EndoPCs was found comprising 359 gene identifiers which allowed to significantly individualized experimental groups (P-value=1.138249e-10) by unsupervised principal component analysis (FIG. 11), but also by unsupervised clustering performed on gene expression heatmap of this profile (Pearson distance, complete method, FIG. 12). These results suggest pancreatic tumoral expression profile could be highlight in the EndoPCs.

We also demonstrated that EndoPCs processing a unique molecular signature were dissimilar to murine iPSCs and were found to be negative by quantitative RT-PCR for gene implicated in the pluripotent maintenance such as OCT4, SOX2, NANOG, LIN28, CMYC, KLF4 and Alkaline phosphatase (ALP) (FIG. 13). These latter results were confirmed by flow cytometry analysis showing the absence of stage-specific embryonic antigen (SSEA)-1 expression (FIG. 14). In addition, EndoPCs shared several genes with Pan02 including PDX1, HNF4A, HNF1B, HNF1A, FOXA2, FOXA3 (data not shown) and are dependent to the IL-6/JAK/STAT3 signaling pathway for their proliferation and self-renewing capacities. To assess the IL-6/JAK/STAT3 axis both Pan02 and EndoPCs we treated with 100 ng/ml of IL-6 and with IL-6 in the presence of a JAK inhibitor.

The activation of this pathway in both cell lines was correlated with a phosphorylation of STAT3 on tyrosine 705 in response to IL-6 (FIG. 15 showing the result for only the Pan02 cells). The detection of the Tyr-705-phospho-STAT3 form by western blot analysis was strongly inhibited after the adjunction of a JAK Inhibitor after 30 minutes and 4 hours of exposition. In addition the activation of the IL-6/JAK/STAT3 axis was associated with an upregulation of 3 catenine and TCF4 mRNA (data not shown).

We then investigated whether vaccination with irradiated EndoPCs in combination with VPA was effective against pancreas cancer in a syngeneic PDAC mice model. The vaccination consisted in injecting by sub cutaneous route two suspensions of $2 \times 10^6$ EndoPCS that were irradiated with a dose of 80 greys.

The cells were injected 7 and 14 days before the orthotropic injection into the tail part of the pancreas of $2 \times 10^6$ Pan02Luc cells expressing the luciferase gene. The mice (n=8) receiving the 2 boosts of vaccine received the day of challenge VPA at the dose of 0.40 mM in drinking water. At the same time, unvaccinated mice received the same number of cancer Pan02Luc cells without VPA. We discovered that in contrast to the none-vaccinated mice, a significant improvement of survival rate following the beforehand injection of mice's with irradiated EndoPCs (FIG. 16). We also found that Pan02 tumors grew progressively in the PBS-control group whereas, strikingly, immunization with EndoPCs resulted in a retardation of tumor growth, with statistically significant differences in the average tumor size in the treated group compared with the control group. The Region of Interest (ROI) measuring the surface intensities by bioluminescence were systematically quantified showing a drastic inhibition of the tumors from the vaccine-treated group from day 4 post-tumor challenge (FIG. 17).

Throughout this application, various references describe the state of the art to which this invention pertains. The disclosures of these references are hereby incorporated by reference into the present disclosure.

REFERENCES

Patent References

EP 2 599 860
PCT/JP2006/324881, PCT/JP02/05350
US 2005/0176707
U.S. Pat. Nos. 5,843,780; 6,200,806; 7,029,913; 5,453,357; 5,690,926; 6,642,048; 6,800,480; 5,166,065; 6,090,622; 6,562,619; 6,921,632; 5,914,268; 9,499,797; 9,637,732; 8,158,766; 8,129,187; 8,058,065; 8,278,104; 8,697,359; 4,684,611; 5,240,840; 4,806,476; 5,298,429; 5,396,767; 5,811,097; 5,811,097; 5,855,887; 6,051,227; 6,207,157; 6,682,736; 6,984,720; 7,605,238; 7,488,802; 7,943,743; 8,008,449; 8,168,757; 8,217,149
WO 2012/122629, WO 2016/065330, WO 2017/027757, WO 2017/202949, WO 2001/085917, WO 2012/060473, WO 03/042402, WO 2008/156712, WO 2010/089411, WO 2010/036959, WO 2011/066342, WO 2011/159877, WO 2011/082400, and WO 2011/161699

Non Patent References

Albrecht T, Schwab R, Peschel C, Engels H J, Fischer T, Huber C, Aulitzky W E. Cationic lipid mediated transfer of c-abl and bcr antisense oligonucleotides to immature normal myeloid cells: uptake, biological effects and modulation of gene expression. Ann Hematol. 1996 February; 72(2):73-9.

Banerji U, van Doorn L, Papadatos-Pastos D, Kristeleit R, Debnam P, Tall M, Stewart A, Raynaud F, Garrett M D, Toal M, Hooftman L, De Bono J S, Verweij J, Eskens F A. A phase I pharmacokinetic and pharmacodynamic study of CHR-3996, an oral class I selective histone deacetylase inhibitor in refractory solid tumors. Clin Cancer Res. 2012 May 1; 18(9):2687-94.

Bartlett D L, Liu Z, Sathaiah M, Ravindranathan R, Guo Z, He Y, Guo Z S. Oncolytic viruses as therapeutic cancer vaccines. Mol Cancer. 2013 Sep. 11; 12(1):103.

Bear A S, Cruz C R, Foster A E. T cells as vehicles for cancer vaccination. J Biomed Biotechnol. 2011; 2011:417403.

Bridle B W, Chen L, Lemay C G, Diallo J S, Pol J, Nguyen A, Capretta A, He R, Bramson J L, Bell J C, Lichty B D, Wan Y. HDAC inhibition suppresses primary immune responses, enhances secondary immune responses, and abrogates autoimmunity during tumor immunotherapy. Mol Ther. 2013 April; 21(4):887-94.

Brignone C, Grygar C, Marcu M, Schakel K, Triebel F. A soluble form of lymphocyte activation gene-3 (IMP321) induces activation of a large range of human effector cytotoxic cells. J Immunol. 2007 Sep. 15; 179(6):4202-11.

Chateauvieux S, Morceau F, Dicato M, Diederich M. Molecular and therapeutic potential and toxicity of valproic acid. J Biomed Biotechnol. 2010; 2010. pii: 479364.

Choi V W, Samulski R J, McCarty D M. Effects of adeno-associated virus DNA hairpin structure on recombination. J Virol. 2005 June; 79(11):6801-7.

Chung Y, Klimanskaya I, Becker S, Li T, Maserati M, Lu S J, Zdravkovic T, Ilic D, Genbacev O, Fisher S, Krtolica A, Lanza R. Human embryonic stem cell lines generated without embryo destruction. Cell Stem Cell. 2008 Feb. 7; 2(2):113-7.

Eggermont L J, Paulis L E, Tel J, Figdor C G. Towards efficient cancer immunotherapy: advances in developing artificial antigen-presenting cells. Trends Biotechnol. 2014 September; 32(9):456-65.

Fatehullah A, Tan S H, Barker N. Organoids as an in vitro model of human development and disease. Nat Cell Biol. 2016 March; 18(3):246-54.

Fourcade J, Sun Z, Benallaoua M, Guillaume P, Luescher I F, Sander C, Kirkwood J M, Kuchroo V, Zarour H M. Upregulation of Tim-3 and PD-1 expression is associated with tumor antigen-specific CD8+ T cell dysfunction in melanoma patients. J Exp Med. 2010 Sep. 27; 207(10): 2175-86.

Fournier R E. A general high-efficiency procedure for production of microcell hybrids. Proc Natl Acad Sci USA. 1981 October; 78(10): 6349-6353.

Gore A, Li Z, Fung H L, Young J E, Agarwal S, Antosiewicz-Bourget J, Canto I, Giorgetti A, Israel M A, Kiskinis E, Lee J H, Loh Y H, Manos P D, Montserrat N, Panopoulos A D, Ruiz S, Wilbert M L, Yu J, Kirkness E F, Izpisua Belmonte J C, Rossi D J, Thomson J A, Eggan K, Daley G Q, Goldstein L S, Zhang K. Somatic coding mutations in human induced pluripotent stem cells. Nature. 2011 Mar. 3; 471(7336):63-7.

Graham F L, van der Eb A J. A new technique for the assay of infectivity of human adenovirus 5 DNA. Virology. 1973 April; 52(2):456-67.

Holmen S L, Vanbrocklin M W, Eversole R R, Stapleton S R, Ginsberg L C. Efficient lipid-mediated transfection of DNA into primary rat hepatocytes. In Vitro Cell Dev Biol Anim. 1995 May; 31(5):347-51.

Hussein S. M., Batada N. N., Vuoristo S., Ching R. W., Autio R., Narva E. Copy number variation and selection during reprogramming to pluripotency. Nature. 2011; 471(7336): 58-62.

Hussein S M, Elbaz J, Nagy A A. Genome damage in induced pluripotent stem cells: assessing the mechanisms and their consequences. BioEssays: news and reviews in molecular, cellular and developmental biology. 2013; 35:152-162.

Lambert C, Schultz R A, Smith M, Wagner-McPherson C, McDaniel L D, Donlon T, Stanbridge E J, Friedberg E C. Functional complementation of ataxia-telangiectasia group D (AT-D) cells by microcell-mediated chromosome transfer and mapping of the AT-D locus to the region 11q22-23. Proc Natl Acad Sci USA Jul. 1, 1991 88 (13) 5907-5911

Le Bolc'h G, Le Bris N, Yaouanc J J, Climent J C, des Abbayes H, Audrézet MP, Férec C. Cationic phosphonolipids as non viral vectors for DNA transfection. Tetrahedron Lett. 1995, September 11; 36: 6681-6684.

Leoni F, Fossati G, Lewis E C, Lee J K, Porro G, Pagani P, Modena D, Moras M L, Pozzi P, Reznikov L L, Siegmund B, Fantuzzi G, Dinarello C A, Mascagni P. The histone deacetylase inhibitor ITF2357 reduces production of pro-inflammatory cytokines in vitro and systemic inflammation in vivo. Mol Med. 2005 January-December; 11(1-12):1-15.

Lin T Y, Fenger J, Murahari S, Bear M D, Kulp S K, Wang D, Chen C S, Kisseberth W C, London C A. AR-42, a novel HDAC inhibitor, exhibits biologic activity against malignant mast cell lines via down-regulation of constitutively activated Kit. Blood. 2010; 115:4217-4225.

Lindor N M, McMaster M L, Lindor C J, Greene M H; National Cancer Institute, Division of Cancer Prevention, Community Oncology and Prevention Trials Research Group. Concise handbook of familial cancer susceptibility syndromes—second edition. J Natl Cancer Inst Monogr. 2008; (38):1-93.

Loeffler J P, Behr J P. Gene transfer into primary and established mammalian cell lines with lipopolyamine-coated DNA. Meth. Enzymol, 1993; 217: 599-618

Loo D, Alderson R F, Chen F Z, Huang L, Zhang W, Gorlatov S, Burke S, Ciccarone V, Li H, Yang Y, Son T, Chen Y, Easton A N, Li J C, Rillema J R, Licea M, Fieger C, Liang T W, Mather J P, Koenig S, Stewart S J, Johnson S, Bonvini E, Moore P A. Development of an Fc-enhanced anti-B7-H3 monoclonal antibody with potent anti-tumor activity. Clin Cancer Res. 2012 Jul. 15; 18(14): 3834-45.

Marchion D C, Bicaku E, Daud A I, Richon V, Sullivan D M, Munster P N. Sequence-specific potentiation of topoisomerase II inhibitors by the histone deacetylase inhibitor suberoylanilide hydroxamic acid. J Cell Biochem. 2004; 92:223-237.

Melief C J, van Hall T, Arens R, Ossendorp F, van der Burg S H. Therapeutic cancer vaccines. J Clin Invest. 2015 September; 125(9):3401-12.

Moffat D, Patel S, Day F, Belfield A, Donald A, Rowlands M, Wibawa J, Brotherton D, Stimson L, Clark V, Owen J, Bawden L, Box G, Bone E, Mortenson P, Hardcastle A, van Meurs S, Eccles S, Raynaud F, Aherne W. Discovery of 2-(6-{[(6-fluoroquinolin-2-yl)methyl]amino}bicyclo [3.1.0]hex-3-yl)-N-hydroxypyrimidine-5-carboxamide (CHR-3996), a class I selective orally active histone deacetylase inhibitor. J Med Chem. 2010 Dec. 23; 53(24): 8663-78.

Nicolaou K C, Li T, Nakada M, Hummel C W, Hiatt A, Wrasidlo W. Calicheamicin θ1: A Rationally Designed Molecule with Extremely Potent and Selective DNA Cleaving Properties and Apoptosis Inducing Activity. Agnew Chem Intl. Ed. Engl. 1994 February, 1; 33(2): 183-186.

V Novotny-Diermayr, S Hart, K C Goh, A Cheong, L-C Ong, H Hentze, M K Pasha, R Jayaraman, K Ethirajulu, J M Wood. The oral HDAC inhibitor pracinostat (SB939) is efficacious and synergistic with the JAK2 inhibitor pacritinib (SB1518) in preclinical models of AML. Blood Cancer J. 2012 May; 2(5): e69.

Pardoll D M. The blockade of immune checkpoints in cancer immunotherapy. Nat Rev Cancer. 2012 Mar. 22; 12(4): 252-64.

Remy J S, Sirlin C, Vierling P, Behr J P. Gene Transfer with a Series of Lipophilic DNA-Binding Molecules. Bioconjugate Chem., 1994, 5 (6), pp 647-654.

Restifo N P, Dudley M E, Rosenberg S A. Adoptive immunotherapy for cancer: harnessing the T cell response. Nat Rev Immunol. 2012 Mar. 22; 12(4):269-81.

Rosenberg S A, Packard B S, Aebersold P M, Solomon D, Topalian S L, Toy S T, Simon P, Lotze M T, Yang J C, Seipp C A, et al. Use of tumor-infiltrating lymphocytes and interleukin-2 in the immunotherapy of patients with metastatic melanoma. A preliminary report. N Engl J Med. 1988 Dec. 22; 319(25):1676-80.

Sakuishi K, Apetoh L, Sullivan J M, Blazar B R, Kuchroo V K, Anderson A C. Targeting Tim-3 and PD-1 pathways to reverse T cell exhaustion and restore anti-tumor immunity. J Exp Med. 2010 Sep. 27; 207(10):2187-94.

Sasaki N, Clevers H. Studying cellular heterogeneity and drug sensitivity in colorectal cancer using organoid technology. Curr Opin Genet Dev. 2018 Sep. 24; 52:117-122.

Strauss W M. Transfection of Mammalian Cells via Lipofection. In: Markie D. (eds) YAC Protocols. Methods in Molecular Biology™, vol 54. Humana Press; 307-327.

Teifel M, Friedl P. New lipid mixture for efficient lipid-mediated transfection of BHK cells. Biotechniques 1995, July 1; 19(1): 79-80.

Ting C C, Lavrin D H, Shiu G, Herberman R B. Expression of Fetal Antigens in Tumor Cells. Proc Natl Acad Sci USA. 1972 July; 69(7): 1664-1668.

Valente S, Mai A. Small-molecule inhibitors of histone deacetylase for the treatment of cancer and non-cancer diseases: a patent review (2011-2013). Expert Opin Ther Pat. 2014 April; 24(4):401-15.

Wigler M, Pellicer A, Silverstein S, Axel R, Urlaub G, Chasin L. DNA-mediated transfer of the adenine phosphoribosyltransferase locus into mammalian cells. Proc Natl Acad Sci USA. 1979 March; 76(3):1373-6.

Wu Z, Asokan A, Samulski R J. Adeno-associated virus serotypes: vector toolkit for human gene therapy. Mol Ther. 2006 September; 14(3):316-27.

Wu D, Wang J, Cai Y, Ren M, Zhang Y, Shi F, Zhao F, He X, Pan M, Yan C, Dou J. Effect of targeted ovarian cancer immunotherapy using ovarian cancer stem cell vaccine. J Ovarian Res. 2015 Oct. 24; 8:68.

Wu J, Izpisua Belmonte J C. Stem Cells: A Renaissance in Human Biology Research. Cell. 2016 Jun. 16; 165(7): 1572-1585.

Zheng Q, Zheng Y, Chen J, You J, Zhu Y, Liu Y, Jiang J J. A hepatic stem cell vaccine is superior to an embryonic stem cell vaccine in the prophylaxis and treatment of murine hepatocarcinoma. Oncol Rep. 2017 March; 37(3): 1716-1724.

The invention claimed is:

1. A method for producing a vaccine composition comprising a population of inactivated cells, comprising:
   (a) expanding pluripotent stem cells, optionally in the presence of a mutagenic agent;
   (b) differentiating the expanded pluripotent stem cells along an ectodermal, endodermal, or mesodermal lineage pathway;
   (c) culturing the differentiated cells in a two-dimensional (2D) culture system or a three-dimensional (3D) organoid culture system while optionally exposing the differentiated cells to a mutagenic agent to further induce genetic changes;
   (d) verifying that at least 70% of the differentiated cells express fetal cell markers, wherein:
   the fetal cell markers expressed by the cells differentiated along the endoderm pathway are selected from SOX17, CXCR4, FOXA1, FOXA2, FOXA3, HHEX, GATA4, GATA6, HNF1B, HNF4A, TF, ALB, TBX3, AFP, TTR, CER1, MIXL1, LHX1, GSC, PAX9, NEPN, SHH, PYY, MNX1, KITL, CLDN4, CLDN8, GFPT2, KRT19, SORCS2, EPPK1, NEDD9, PLAT, VTN, PDX1, TMPRSS4, CLIC6, RIPK4, CLDN8, and ST1A;
   the fetal cell markers expressed by the cells differentiated along the ectoderm pathway are selected from PCGF4, PAX6, PAX7, CXCR4, SOX1, SOX2, SOX10, ITGB1, FABP7, NES, FUT4, PROM1, MELK, MS11, MAP2, DCX, NCAM1, TUBB3, SLC1A3, CD44, S100B, VIM, GFAP, CNP, OLIG2, CA2, CSPG4, TAZ, MSX1, SPARC, ID2, NES, NKX2.2, NKX6-1, FOXP2, FOXD3, and ZIC1; and
   the fetal cell markers expressed by the cells differentiated along the mesoderm pathway are selected from Brachury (T), MIXL1, SNA11, SNA12, HLX, EOMES, MESP1, MESP2, TBX6, MEST, NKX2-5, and KDR;
   (e) optionally, verifying that the differentiated cells express at least one tumor associated antigen (TAA) or neo-antigen that is present in cancer cells; and
   (f) inactivating the differentiated cells by irradiation so they lose their ability to divide, thereby obtaining a population of inactivated cells, wherein no more than 10% of the population of inactivated cells express the following makers characteristic of pluripotency: NANOG, POU5F1 (Oct4), SSEA4, Tra-1-81, and Tra-1-60; and
   (g) formulating the inactivated cells into an effective vaccine composition.

2. The method of claim 1, wherein the mutagenic agent in (a) is a chemical mutagenic agent or a radiation mutagenic agent; and the mutagenic agent in (c) is a chemical mutagenic agent or a radiation mutagenic agent.

3. The method of claim 1, wherein the mutagenic agent in (a) is N-ethyl-N-nitrosourea (ENU), a reactive oxygen species, a deaminating agent, a polycyclic aromatic hydrocarbon, an aromatic amines, or sodium azide; and the mutagenic agent in (c) is N-ethyl-N-nitrosourea (ENU), a reactive oxygen species, a deaminating agent, a polycyclic aromatic hydrocarbon, an aromatic amines, or sodium azide.

4. The method of claim 3, wherein the mutagenic agent in (a) and (c) is ENU.

5. The method of claim 1, wherein an agent is added during culture (c) that improves presentation of antigens through the Major Histocompatibility Complex I (MHC I) pathway.

6. The method of claim 5, wherein the agent that improves presentation of antigens through the MHC I pathway is a histone deacetylase inhibitor (HDACi).

7. The method of claim 6, wherein the HDACi is valproic acid.

8. The method of claim 1, wherein the pluripotent stem cells are induced pluripotent stem cells (iPSCs).

9. The method of claim 1, wherein the differentiated cells are cultured in (c) to form an organoid.

10. The method of claim 9, wherein the 3D structure of the organoid is disrupted before inactivating the cells.

11. The method of claim 1, further comprising freezing or lyophilizing the inactivated cells.

12. The method of claim 1, wherein the pluripotent cells are induced Pluripotent Stem Cells (iPSCs).

13. The method of claim 12, wherein the iPSCs are human iPSCs.

14. The method of claim 2, wherein the iPSCs have been obtained from a human with a cancer.

15. The method of claim 14, comprising verification that the differentiated cells express at least one tumor associated antigen (TAA) present in the human cancer cells.

* * * * *